(12) United States Patent
Stiegler et al.

(10) Patent No.: US 6,204,010 B1
(45) Date of Patent: Mar. 20, 2001

(54) FLEA PROTEASE PROTEINS, NUCLEIC ACID MOLECULES, AND USES THEREOF

(75) Inventors: Gary L. Stiegler; Patrick J. Gaines, both of Ft. Collins, CO (US)

(73) Assignee: Heska Corporation, Ft. Collins, CO (US)

( * ) Notice: Subject to any disclaimer, the term of this patent is extended or adjusted under 35 U.S.C. 154(b) by 0 days.

(21) Appl. No.: 09/032,215

(22) Filed: Feb. 27, 1998

Related U.S. Application Data

(63) Continuation-in-part of application No. 08/970,995, filed on Nov. 14, 1997, and a continuation-in-part of application No. PCT/US97/06121, filed on Apr. 24, 1997, and a continuation-in-part of application No. 08/749,699, filed on Nov. 15, 1996, and a continuation-in-part of application No. 08/639,075, filed on Apr. 24, 1996, and a continuation-in-part of application No. 08/817,795, filed on Aug. 1, 1997, and a continuation-in-part of application No. PCT/US95/14442, filed on Oct. 18, 1995, and a continuation-in-part of application No. 08/484,211, filed on Jun. 7, 1995, now Pat. No. 5,972,645.

(51) Int. Cl.$^7$ ............................. C12N 15/12; C12N 15/52
(52) U.S. Cl. ...................... 435/69.1; 536/23.1; 536/23.2; 435/325; 435/320.1; 435/252.33; 424/93.2
(58) Field of Search .............................. 514/44; 424/93.2; 536/23.1, 23.2; 435/69.1, 320.1, 325, 252.33

(56) References Cited

U.S. PATENT DOCUMENTS

| | | |
|---|---|---|
| 3,826,232 | 7/1974 | Duffey et al. . |
| 4,800,159 | 1/1989 | Mullis et al. . |
| 4,973,555 | 11/1990 | Weissman et al. . |
| 4,973,589 | 11/1990 | Barnett et al. . |
| 5,057,527 | 10/1991 | Alig et al. . |
| 5,288,612 | 2/1994 | Griffin et al. . |
| 5,304,482 | 4/1994 | Sambrook et al. . |
| 5,356,622 | 10/1994 | Health et al. . |
| 5,371,239 | 12/1994 | Doscher . |
| 5,712,143 | * 1/1998 | Grieve et al. . |

FOREIGN PATENT DOCUMENTS

| | | |
|---|---|---|
| 0571911 | 12/1993 | (EP) . |
| WO 90/03433 | 9/1990 | (WO) . |
| 9312141 | 7/1993 | (WO) . |
| WO 93/23542 | 11/1993 | (WO) . |
| WO 96/11706 | * 4/1996 | (WO) . |
| WO 97/40058 | * 10/1997 | (WO) . |

OTHER PUBLICATIONS

Gaines, P.J. et al., *Insect Molecular Biology*, 8(1):11–22, 1999.*
Sequence alignment from database, Bernstein et al., 1983, *Immunogenetics*, 18:387–397.
Eakin et al., 1990, *Molecular and Biochemical Parasitology*, 39:1–8.
Sequence alignment from database, Roberts et al., 1990, *Science*, 248:358.
Sakanari et al., 1989, *Proc. Nat'l Acad. Sci. USA*, 86:4863–4867.
Azad et al., 1987, *Am. J. Trop. Med. Hyg.*, 37:629–635.
Billingsley, 1990 *Annu. Rev. Entomol.*, 35:219–248.
Borovsky et al., 1990 *FASEB J.*, 4:3015–3020.
Borovsky, 1988 *Arch. Insect Biochem. Physiol.*, 7:187–210.
Casu et al, 1994 *Insect. Mol. Biol.*, 3(4):201–211.
Casu et al., 1994 *Insect Mol. Biol.*, 3(3):159–170.
Chaikau, 1982 *Entomol. Obozor* 61(4):746–754.
Cherney et al., 1939 *Am J. Trop. Med.*, 19:327–332.
Chinzel et al., 1987 *Med. Vet. Entomol.*, 1:409–416.
Cuypers, et al., 1982, *J. Biol. Chem.*, 257(12):7077–7085.
Eldridge et al., 1993 *Seminars in Hemotology*, 30(4)(Supp.4):16–25.
Elvin et al., 1993 *Mol. Gen. Genet.*, 240:132–139.
Halliwell, 1973 *J. Immunol.*, 110:422–430.
Halliwell, et al., 1978 *J. Allerg. Clin. Immunol.*, 62:236–242.
Halliwell et al., 1985 *Vet. Immunol. Immunopathol.*, 8:215–223.
Hatfield, 1988 *Med. Vet. Entomol.*, 2:331–338.
Hatfield, 1988 *Med. Vet. Entomol.*, 2:339–345.
Houk et al., 1986 *Archives of Insect Biochemistry and Physiology*, 3:135–146.
Jany et al., 1983, *Biochem. & Biophys. Res. Comm.*, 110(1):1–7.
Johnson et al., 1986 *Int. J. Parasitol.*, 16(1):27–34.
Kolhok et al., 1993 *Insect Mol. Biol.*, 2(2):71–79.
Kay et al., 1994 *Am J. Trop. Med. Hyg.*, 50(6) Suppl.:87–96.
Kemp et al., 1986 *Internat. J. Parasitol.*, 16, 155–120.
Kwochka, 1987 *Vet. Clin. North Am.*, 17:1235–1262.
Law et al., 1992 *Annu. Rev. Biochem.*, 61:87–111.
Matshushima, et al., 1991, *Biochem. & Biophys. Res. Comm.*, 178(3):1459–1464.
McFarlane, 1985 *Fundamentals of Insect Physiology*, 59–89.
Muller et al., 1993 *EMBO J.*, 12(7):2891–2900.
Nesbitt et al., 1978 *J. Am. Vet. Med. Assoc.*, 173:282–288.
Opdebeeck et al., 1988 *Immunol.*, 63:363–367.
Opdebeeck et al., 1988 *Parasite Immunol.*, 10:405–410.

(List continued on next page.)

Primary Examiner—Marianne P. Allen
(74) Attorney, Agent, or Firm—Sheridan Ross P.C.

(57) ABSTRACT

The present invention relates to flea serine protease proteins; to flea serine protease nucleic acid molecules, including those that encode such proteins; to antibodies raised against such proteins; and to compounds that inhibit flea serine protease activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

14 Claims, No Drawings

OTHER PUBLICATIONS

Opdebeeck et al., 1989 *Immunol.*, 67:388.
Otieno et al., 1984 *Insect Sci. Applic.*, 5(4):297–302.
Ramos et al., 1993 *Insect Mol. Biol.*, 1(3):149–163.
Rand et al., 1989 *Proc. Natl. Acad. Sci. (USA)*, 86:9657–9661.
Reeves et al. 1993 *Insect Biochem. & Mol. Biol.* 23(7):809–14.
Ribiero, 1987 *Ann. Rev. Entomol.*, 32:463–478.
Roitt et al., 1985, *Immunology*, pp. 5.4–5.5.
Sandeman et al., 1990 *Int. J. Parasitol.*, 20(8):1019–1023.
Sarkar et al., 1990, *Genomics*, 6(1):133–143.
Schedrin et al. 1978 *Med. Parazitol. Parazit Bolezni* 47(1):89–91.
Schlein et al., 1976 *Physiolog. Entomol.*, 1:55–59.
Soulsby, 1982, *Helminths, Arthopods and Protozoa of Domesticated Animals*, 7th ed., 378–384.
Vaughn et al., 1988 *J. Med. Entomol.*, 25:472–474.
Wade et al., 1988, *J. Med Entomol.*, 25(3):186–190.
Wikel, 1984 *Vet. Parasitol.*, 14:321–339.
Wikel, 1988 *Vet. Parasitol.*, 29:235–264.
Willadsen et al., 1989 *J. Immunol.*, 143:1346–1351.
Wong et al., 1989 *Immunol.*, 66:149–155.
Young et al., 1963 *Exp. Parasitol*, 13:155–166.
Zwilling et al., 1975, *Febs Letters*, 60(2):247–249.

* cited by examiner

FLEA PROTEASE PROTEINS, NUCLEIC ACID MOLECULES, AND USES THEREOF

CROSS-REFERENCE TO RELATED APPLICATIONS

The present invention is a continuation-in-part of pending U.S. patent application Ser. No. 08/970,995, filed on Nov. 14, 1997. The present invention is a continuation-in-part of pending PCT Application No. PCT/US97/06121, filed on Apr. 24, 1997 and designating the United States. The present invention is a continuation-in-part of pending U.S. patent application Ser. No. 08/749,699, filed on Nov. 15, 1996. The present invention is a continuation-in-part of pending U.S. patent application Ser. No. 08/639,075, filed on Apr. 24, 1996. The present invention is a continuation-in-part of pending U.S. patent application Ser. No. 08/817,795, filed Aug. 1, 1997 which is a continuation-in-part of PCT Application No. PCT/US95/14442, filed on Oct. 18, 1995. The present invention is a continuation-in-part of pending U.S. patent application Ser. No. 08/484,211, filed on June 7, 1995 now U.S. Pat. No. 5,972,645. Each of the applications referred to in this section is incorporated herein by reference in its entirety.

FIELD OF THE INVENTION

The present invention relates to novel flea protease proteins and their use to reduce flea infestation of animals. The present invention also relates to the use of anti-flea protease antibodies and other compounds that reduce flea protease activity to reduce flea infestation of animals.

BACKGROUND OF THE INVENTION

Fleas, which belong to the insect order Siphonaptera, are obligate ectoparasites for a wide variety of animals, including birds and mammals. Flea infestation of animals is of health and economic concern because fleas are known to cause and/or transmit a variety of diseases. Fleas cause and/or carry infectious agents that cause, for example, flea allergy dermatitis, anemia, murine typhus, plague and tapeworm. In addition, fleas are a problem for animals maintained as pets because the infestation becomes a source of annoyance for the pet owner who may find his or her home generally contaminated with fleas which feed on the pets. As such, fleas are a problem not only when they are on an animal but also when they are in the general environment of the animal.

The medical and veterinary importance of flea infestation has prompted the development of reagents capable of controlling flea infestation. Commonly encountered methods to control flea infestation are generally focused on use of insecticides in formulations such as sprays, shampoos, dusts, dips, or foams, or in pet collars. While some of these products are efficacious, most, at best, offer protection of a very limited duration. Furthermore, many of the methods are often not successful in reducing flea populations on the pet for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Additional anti-flea products include non-toxic reagents such as insect growth regulators (IGRs), including methoprene, which mimics flea hormones and affect flea larval development.

An alternative method for controlling flea infestation is the use of flea vaccines to be administered to animals prior to or during flea infestation. However, despite considerable interest in developing anti-flea reagents, no flea vaccine presently exists.

SUMMARY OF THE INVENTION

The present invention relates to flea serine protease proteins; to flea serine protease nucleic acid molecules, including those that encode such proteins; to antibodies raised against such proteins; and to compounds that inhibit flea serine proteases. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

One embodiment of the present invention is an isolated nucleic acid molecule that hybridizes under stringent hybridization conditions with a gene including a serine protease gene comprising a nucleic acid sequence including a nucleic acid molecule including SEQ ID NO:7, SEQ ID NO:23, SEQ ID NO:28, SEQ ID NO:33, SEQ ID NO:38, SEQ ID NO:43, and/or SEQ ID NO:48.

The present invention also includes a nucleic acid molecule that hybridizes under stringent hybridization conditions with a nucleic acid sequence encoding a protein comprising an amino acid sequence including, SEQ ID NO:8, SEQ ID NO:22, SEQ ID NO:27, SEQ ID NO:32, SEQ ID NO:37, SEQ ID NO:42 and/or SEQ ID NO:47 or with a nucleic acid sequence that is a complement of any of the nucleic acid sequences. A preferred nucleic acid sequence of the present invention includes a nucleic acid molecule comprising a nucleic acid sequence including SEQ ID NO:6, SEQ ID NO:7, SEQ ID NO:9, SEQ ID NO:10, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID) NO:48, SEQ ID NO:49 and SEQ ID NO:50; and a nucleic acid molecule comprising an allelic variant of a nucleic acid molecule having any of said nucleic acid sequences.

The present invention also includes an isolated protein encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Yet another embodiment of the present invention is a therapeutic composition that is capable of reducing hematophagous ectoparasite infestation. Such a therapeutic composition includes a protective compound including: an isolated protein or mimetope thereof encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ Iolated nucleic acid molecule that hybridizes under stringent hybridization conditions with a gene comprising a nucleic acid sequence including SEQ ID NO:7, SEQ ID NO:23, SEQ ID NO:28, SEQ ID NO:33, SEQ ID NO:38, SEQ ID NO:43 and/or SEQ ID NO:48; an isolated antibody that selectively binds to a protein encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47; an inhibitor of protease activity identified by its ability to inhibit the activity of a protein encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47; and a mixture thereof. Also included in the present invention is a method to reduce flea infestation, comprising the step of administering to the animal a therapeutic composition of the present invention.

Another embodiment of the present invention is a method to identify a compound capable of inhibiting flea protease activity, the method comprising: (a) contacting an isolated flea protease protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47 with a putative inhibitory compound under conditions in which, in the absence of said compound, the protein has proteolytic activity; and (b) determining if the putative inhibitory compound inhibits the activity. The present invention also includes a kit to identify a compound capable of inhibiting flea protease activity.

DETAILED DESCRIPTION OF THE INVENTION

The present invention includes the use of compounds that inhibit flea protease activity to protect a host animal from flea infestation. The inventors have discovered that proteases are significant components of the flea midgut and are good targets for immunotherapeutic and/or chemotherapeutic intervention to reduce flea burden both on the host animal and in the immediate (i.e., surrounding) environment of the animal. The inventors have shown, for example, that the viability and/or fecundity of fleas consuming a blood meal is reduced when the blood meal contains compounds that reduce flea protease activity, probably because the compounds interfere with flea digestion and other functions. Compounds that reduce the amount and/or activity of flea proteases without substantially harming the host animal are included in, the present invention. Such compounds include flea protease vaccines, anti-flea protease antibodies, flea protease inhibitors, and/or compounds that suppress protease synthesis; such compounds are discussed in more detail below.

One embodiment of the present invention is a method to protect a host animal from flea infestation by treating the animal with a composition that includes a compound that reduces the protease activity of fleas feeding (includes fleas in the process of feeding as well as fleas having fed) from the treated animal thereby reducing the flea burden on the animal and in the environment of the animal. It is to be noted that the term "a" or "an" entity refers to one or more of that entity; for example, a compound refers to one or more compounds. As such, the terms "a" (or "an"), "one or more" and "at least one" can be used interchangeably herein. Thus, a composition of the present invention can include one or more compounds that target (reduced the activity of) one or more proteases in the flea.

As used herein, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment surrounding the animal (i.e., in the environment of the animal). Such an environment can include not only adult fleas, but also flea eggs and/or flea larvae. The environment can be of any size such that fleas in the environment are able to jump onto and off of a host animal. As such, it is desirable not only to reduce the flea burden on an animal per se, but also to reduce the flea burden in the environment surrounding the animal.

In accordance with the present invention, a host animal is treated by administering to the animal a compound of the present invention in such a manner that the compound itself (e.g., a protease inhibitor, protease synthesis suppressor or anti-flea protease antibody) or a product generated by the animal in response to administration of the compound (e.g., antibodies produced in response to a flea protease vaccine, or conversion of an inactive inhibitor "prodrug" to an active protease inhibitor) ultimately enters the flea midgut. An animal is preferably treated in such a way that the compound or product thereof enters the blood stream of the animal. Fleas are then exposed to the compound when they feed from the animal. For example, flea protease inhibitors administered to an animal are administered in such a way that the inhibitors enter the blood stream of the animal, where they can be taken up by feeding fleas. In another embodiment, when a host animal is administered a flea protease vaccine, the treated animal mounts an immune response resulting in the production of antibodies against the protease (anti-flea protease antibodies) which circulate in the animal's blood stream and are taken up by fleas upon feeding. Blood taken up by fleas enters the flea midgut where compounds of the present invention, or products thereof, such as anti-flea protease antibodies, flea protease inhibitors, and/or protease synthesis suppressors, interact with, and reduce proteolytic activity in the flea midgut. The present invention also includes the ability to reduce larval flea infestation in that when fleas feed from a host animal that has been administered a therapeutic composition of the present invention, at least a portion of compounds of the present invention, or products thereof, in the blood taken up by the flea are excreted by the flea in feces, which is subsequently ingested by flea larvae. It is of note that flea larvae obtain most, if not all, of their nutrition from flea feces.

In accordance with the present invention, reducing proteolytic activity in flea midguts can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

One embodiment of the present invention is a composition that includes one or more compounds that reduce the activity of one or more flea proteases directly (e.g., an anti-flea protease antibody or a flea protease inhibitor) and/or indirectly (e.g., a flea protease vaccine). Suitable flea proteases to target include flea aminopeptidases, flea carboxypeptidases and/or flea endopeptidases. Such proteases can include cytosolic and/or membrane-bound forms of a protease. Preferred flea proteases to target include, but are not limited to, serine proteases, metalloproteases, aspartic acid proteases and/or cysteine proteases. It is to be noted that these preferred groups of proteases include aminopeptidases, carboxypeptidases and/or endopeptidases. Preferred flea proteases to target include, but are not limited to, proteases that degrade hemoglobin, proteases involved in blood coagulation and/or lytic (anti-coagulation) pathways, proteases involved in the maturation of peptide hormones, proteases that inhibit complement or other host immune response elements (e.g., antibodies) and/or proteases involved in vitellogenesis. A number of proteases are known to those skilled in the art, including, but not limited to, aminopeptidases, such as leucine aminopeptidase and aminopeptidases B and M; astacin-like metalloproteases; calpains; carboxypeptidases, such as carboxypeptidases A, P and Y; cathepsins, such as cathepsins B, D, E, G, H, and L; chymotrypsins; cruzipains; meprins; papains; pepsins; renins; thermolysins and trypsins. A particularly preferred protease to target is a protease having a proteolytic activity that, when targeted with a composition of the present invention, reduces flea burden without substantially harming the host animal. Such a protease can be identified using, for example, methods as disclosed herein.

One aspect of the present invention is the discovery that a substantial amount of the proteolytic activity found in flea midguts is serine protease activity. Both in vitro and in vivo studies using a number of protease inhibitors substantiate this discovery, details of which are disclosed in the Examples. As such a particularly preferred protease to target is a serine protease. Examples of serine proteases, include, but are not limited to, acrosins, bromelains, cathepsin G, chymotrypsins, collagenases, elastases, factor Xa, ficins, kallikreins, papains, plasmins, Staphylococcal V8 proteases, thrombins and trypsins. In one embodiment, a preferred flea serine protease to target includes a protease having trypsin-like or chymotrypsin-like activity. It is appreciated by those skilled in the art that an enzyme having "like" proteolytic activity has similar activity to the referenced protease, although the exact structure of the preferred substrate cleaved may differ. "Like" proteases usually have similar tertiary structures as their referenced counterparts.

Protease inhibitor studies disclosed in the Examples section also indicate that additional preferred proteases to target include aminopeptidases and/or metalloproteases. Examples of such proteases include exo- and endo-metalloproteases, digestive enzymes, and enzymes involved in peptide hormone maturation. One example of an aminopeptidase that is also a metalloprotease is leucine aminopeptidase.

Suitable compounds to include in compositions of the present invention include, but are not limited to, a vaccine comprising a flea protease (a flea protease vaccine), an antibody that selectively binds to a flea protease (an anti-flea protease antibody), a flea protease inhibitor (a compound other than a vaccine or an antibody that inhibits a flea protease), and a mixture of such compounds. As used herein, a mixture thereof refers to a combination of one or more of the cited entities. Compositions of the present invention can also include compounds to suppress protease synthesis or maturation, such as, but not limited to, protease modulating peptides.

A preferred embodiment of the present invention is a flea protease vaccine and its use to reduce the flea population on and around an animal. A flea protease vaccine can include one or more proteins capable of eliciting an immune response against a flea protease and can also include other components. Preferred flea protease vaccines include a flea serine protease, a flea metalloprotease, a flea aspartic acid protease and/or a flea cysteine protease, with flea serine protease, flea metalloprotease and/or flea aminopeptidase vaccines being more preferred. Examples of flea protease vaccines include one or more isolated proteins of the present invention.

One embodiment of the present invention is an isolated protein that includes an amino acid sequence encoded by a nucleic acid molecule capable of hybridizing under stringent conditions (i.e., that hybridize under stringent hybridization conditions) with a nucleic acid molecule that encodes a protease present (i.e., the nucleic acid molecules hybridize with the nucleic acid strand that is complementary to the coding strand) in (i.e., can be found in) a flea midgut, such as a midgut from a blood-fed female flea, a midgut from a blood-fed male flea, a midgut from an unfed female flea or a midgut from an unfed male flea. A preferred midgut protease is present in the lumen of the midgut.

An isolated protein of the present invention, also referred to herein as an isolated protease protein, preferably is capable of eliciting an immune response against a flea midgut protease and/or has proteolytic activity. According to the present invention, an isolated, or biologically pure, protein, is a protein that has been removed from its natural milieu. As such, "isolated" and "biologically pure" do not necessarily reflect the extent to which the protein has been purified. An isolated protease protein can be obtained from its natural source. Such an isolated protein can also be produced using recombinant DNA technology or chemical synthesis.

As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue comprises a protein having an amino acid sequence that is sufficiently similar to a natural flea midgut protease that a nucleic acid sequence encoding the homologue is capable of hybridizing under stringent conditions to (i.e., with) the complement of a nucleic acid sequence encoding the corresponding natural flea midgut protease amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Protease protein homologues of the present invention preferably have protease activity and/or are capable of eliciting an immune response against a flea midgut protease.

A protease protein homologue of the present invention can be the result of allelic variation of a natural gene encoding a flea protease. A natural gene refers to the form of the gene found most often in nature. Protease protein homologues can be produced using techniques known in the art including, but not limited to, direct modifications to a gene encoding a protein using, for example, classic or recombinant DNA techniques to effect random or targeted mutagenesis. Isolated protease proteins of the present invention, including homologues, can be identified in a straightforward manner by the proteins' ability to effect proteolytic activity and/or to elicit an immune response against a flea midgut protease. Such techniques are known to those skilled in the art.

A preferred protease protein of the present invention is a flea serine protease, a flea metalloprotease, a flea aspartic acid protease, a flea cysteine protease, or a homologue of any of these proteases. A more preferred protease protein is a flea serine protease, a flea metalloprotease or a homologue of either. Also preferred is a flea aminopeptidase or a homologue thereof. Also preferred is a flea cysteine protease or a homologue thereof. Particularly preferred is a flea serine protease or a homologue thereof.

One preferred embodiment of the present invention is an isolated flea protease protein that includes an amino acid sequence encoded by a nucleic acid molecule that hybridizes under stringent hybridization conditions with a flea serine protease gene. As used herein, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself.

The inventors have discovered an extensive family of serine proteases, encoded by a family of serine protease genes. Such a gene family may be due to allelic variants (i.e., genes having similar, but different, sequences at a given locus in a population of fleas) and/or to, the existence of serine protease genes at more than one locus in the flea genome. As such, the present invention includes flea serine protease genes comprising not only the nucleic acid sequences disclosed herein (e.g., genes including nucleic acid sequences SEQ ID NO:6, SEQ ID NO:7, SEQ ID NO:9, SEQ ID NO:10, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:48, SEQ ID NO:49 and/or SEQ ID NO:50), and/or nucleic acid sequences encoding proteins having amino acid sequences as disclosed herein (e.g., SEQ ID NO:8, SEQ ID NO:22, SEQ ID NO:27, SEQ ID NO:32, SEQ ID NO:37, SEQ ID NO:42 and/or SEQ ID NO:47), but also allelic variants of any of those nucleic acid sequences. (It should be noted that since nucleic acid sequencing technology is not entirely error-free, all sequences represented herein are at best apparent (i.e., deduced) nucleic acid or amino acid sequences.)

A preferred flea serine protease protein of the present invention is encoded by a nucleic acid molecule that hybridizes under stringent hybridization conditions with a nfSP33$_{1373}$, nfSP33$_{1161}$, nfSP8$_{1303}$, nfSP8$_{1152}$, nfSP2$_{945}$, nfSP2$_{769}$, nfSP6$_{932}$, nfSP6$_{768}$, nfSP20$_{841}$, nfSP20$_{744}$, nfSP329$_{33}$, nfSP32$_{804}$, nfSP40$_{841}$ and/or nfSP40$_{726}$ nucleic acid molecule. The production of such nucleic acid molecules is disclosed in the Examples. An even more preferred serine protease protein comprises an amino acid sequence including SEQ ID NO:8, SEQ ID NO:22, SEQ ID NO:27, SEQ ID NO:32, SEQ ID NO:37, SEQ ID NO:42 and SEQ ID NO:47. Additional preferred serine protease proteins are encoded by allelic variants of nucleic acid molecules encoding proteins that include the cited amino acid sequences. Also preferred are flea serine protease proteins including regions that have at least about 50%, preferably at least about 60%, more preferably at least about 70%, more preferably at least about 75%, more preferably at least about 80%, more preferably at least about 85% and more preferably at least about 90% identity with flea serine protease proteins having amino acid sequences as cited herein.

Methods to determine percent identities between amino acid sequences and between nucleic acid sequences are known to those skilled in the art. Preferred methods to determine percent identities between sequences include computer programs such as GCV program (available from Genetics Computer Group, Madison, Wisc.), the MacVectors program (available from the Eastman Kodak Company, New Haven, Conn.), or the DNAsis™ program (available from Hitachi Software, San Bruno, Calif.).

One embodiment of the present invention is an isolated protein having proteolytic activity that is substantially inhibited by a serine protease inhibitor. Such inhibition can be measured by techniques known to those skilled in the art. To be substantially inhibited means, for example, for a serine protease, that at least half of the proteolytic activity of the protease protein is inhibited by a serine protease inhibitor. Preferably at least about 70 percent and even mores preferably at least about 90 percent of the proteolytic activity of the protease protein is inhibited by a serine protease inhibitor.

An isolated protein of the present invention can be produced in a variety of ways, including recovering such a protein from a flea midgut and producing such a protein recombinantly. In one embodiment, a flea midgut protease can be recovered by methods heretofore disclosed for obtaining a soluble flea midgut preparation. A flea midgut protease protein can be further purified from a disrupted flea midgut by a number of techniques known to those skilled in the art, including, but not limited to, affinity chromatography, ion exchange chromatography, filtration, electrophoresis (e.g., standard, capillary and flow-through electrophoresis), hydrophobic interaction chromatography, gel filtration chromatography, reverse phase chromatography, concanavalin A chromatography, chromatofocusing and differential solubilization. In one embodiment, a flea midgut protease is purified using protease inhibitor affinity chromatography, an example of which is disclosed in the Examples section.

Another embodiment of the present invention is a method to produce an isolated protein of the present invention using recombinant DNA technology. Such a method includes the steps of (a) culturing a recombinant cell comprising a nucleic acid molecule encoding a protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques, as heretofore disclosed.

Isolated proteins of the present invention are preferably retrieved in "substantially pure" form. As used herein, "substantially pure" refers to a purity that allows for the effective use of the protein as a vaccine. A vaccine for animals, for example, should exhibit no substantial toxicity and should be capable of stimulating the production of antibodies in a vaccinated animal.

Another embodiment of the present invention is an isolated nucleic acid molecule capable of hybridizing under stringent conditions with a gene encoding a flea protease present in a flea midgut. Such a nucleic acid molecule is also referred to herein as a flea protease nucleic acid molecule. Particularly preferred is an isolated nucleic acid molecule that hybridizes under stringent conditions with a flea serine protease gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself. A nucleic acid molecule of the present invention can be an isolated natural flea protease nucleic acid molecule or a homologue thereof. A nucleic acid molecule of the present invention can include one or more regulatory regions, full-length or partial coding regions, or combinations thereof. The minimal size of a flea protease nucleic acid molecule of the present invention is the minimal size capable of forming a stable hybrid under stringent hybridization conditions with a corresponding natural gene. Flea protease nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated flea protease nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a flea protease protein of the present invention or to form stable hybrids under stringent conditions with natural nucleic acid molecule isolates.

A flea protease nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against a flea protease and/or to have proteolytic activity) and/or by hybridization with isolated flea protease nucleic acids under stringent conditions.

An isolated flea protease nucleic acid molecule of the present invention can include a nucleic acid sequence that encodes at least one flea protease protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an flea protease protein.

One embodiment of the present invention is a flea protease nucleic acid molecule of the present invention that is capable of hybridizing under stringent conditions to a nucleic acid strand that encodes at least a portion of a flea protease or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present i invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Preferred is a flea protease nucleic acid molecule that includes a nucleic acid sequence having at least about 65 percent, preferably at least about 70 percent, more preferably at least about 75 percent, more preferably at least about 80 percent, more preferably at least about 85 percent, more preferably at least about 90 percent and even more preferably at least about 95 percent homology with the corresponding region(s) of the nucleic acid sequence encoding at least a portion of a flea protease protein. Particularly preferred is a flea protease nucleic acid molecule capable of encoding at least a portion of a flea protease that naturally is present in flea midguts and preferably is included in a soluble flea midgut preparation of the present invention. Examples of nucleic acid molecules of the present invention are disclosed in the Examples section.

A preferred flea serine protease nucleic acid molecule of the present invention is a nucleic acid molecule that hybridizes under stringent hybridization conditions with nfSP33, nfSP8, nfSP2, nfSP6, nfSP20, nfSP32, and/or nfSP40 nucleic acid molecules. More preferred is a nucleic acid molecule that hybridizes under stringent hybridization conditions with nfSP33$_{1373}$, nfSP33$_{1161}$, nfSP8$_{1303}$, nfSP8$_{1152}$, nfSP2$_{945}$, nfSP2$_{768}$, nfSP6$_{932}$, nfSP6$_{768}$, nfSP20$_{841}$, nfSP20$_{744}$, nfSP32$_{933}$, nfSP32$_{804}$, nfSP40$_{841}$ and nfSP40$_{726}$ as well as other specific nucleic acid molecules disclosed in the Examples section. Even more preferred is nucleic acid molecule nfSP33$_{1373}$, nfSP33$_{1161}$, nfSP8$_{1303}$, nfSP8$_{1152}$, nfSP2$_{945}$, nfSP2$_{768}$, nfSP6$_{932}$, nfSP6$_{768}$, nfSP20$_{841}$, nfSP20$_{744}$, nfSP32$_{933}$, nfSP32$_{804}$, nfSP40$_{841}$ and nfSP40$_{726}$, as well as other specific nucleic acid molecules disclosed in the Examples section.

Particularly preferred flea serine protease nucleic acid molecules include at least one of the following sequences: SEQ ID NO:6, SEQ ID NO:7, SEQ ID NO:9, SEQ ID NO:10, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:48, SEQ ID NO:49 and/or SEQ ID NO:50. Also preferred are allelic variants of such nucleic acid molecules.

Knowing a nucleic acid molecule of a flea protease protein of the present invention allows one skilled in the art to make copies of that nucleic acid molecule as well as to obtain a nucleic acid molecule including additional portions of flea protease protein-encoding genes (e.g., nucleic acid molecules that include the translation start site and/or transcription and/or translation control regions), and/or flea protease nucleic acid molecule homologues. Knowing a portion of an amino acid sequence of a flea protease protein of the present invention allows one skilled in the art to clone nucleic acid sequences encoding such a flea protease protein. In addition, a desired flea protease nucleic acid molecule can be obtained in a variety of ways including screening appropriate expression libraries with antibodies which bind to flea protease proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea protease nucleic acid molecules, preferred cDNA libraries include cDNA libraries made from unfed whole fleas, fed whole fleas, fed flea midguts, unfed flea midguts, and flea salivary glands. Techniques to clone and amplify genes are disclosed, for example, in Sambrook et al., ibid. The Examples section includes examples of the isolation of cDNA sequences encoding flea protease proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea protease protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit flea protease production. Such therapeutic applications include the use of such oligonucleotides in, for example, antisense-, triplex formation-, ribozyme- and/or RNA drug-based technologies. The present invention, therefore, includes such oligonucleotides and methods to interfere with the production of flea protease proteins by use of one or more of such technologies.

The present invention also includes a recombinant vector, which includes a flea protease nucleic acid molecule of the present invention inserted into any vector capable of delivering the nucleic acid molecule into a host cell. Such a vector contains heterologous nucleic acid sequences, that is nucleic acid sequences that are not naturally found adjacent to flea protease nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of flea protease nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a flea protease protein of the present invention by culturing a cell capable of expressing the protein under conditions effective to produce the protein, and recovering the protein. A preferred cell to culture is a recombinant cell that is capable of expressing the flea protease protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced flea protease protein. Such cells are, therefore, capable of producing flea protease proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to the art. Preferred transcription control sequences include those which function in bacterial, yeast, helminth, insect and mammalian cells, such as, but not limited to, tac, lac, tzp, trc, oxy-pro, omp/lpp, rrnB, bacteriophage lambda ($\lambda$) (such as $\lambda.p_L$ and $\lambda.p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, Heliothis zea insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a flea protease protein.

Expression vectors of the present invention may also contain secretory signals (i.e., signal segment nucleic acid sequences) to enable an expressed flea protease protein to be secreted from the cell that produces the protein. Suitable signal segments include a flea protease protein signal segment or any heterologous signal segment capable of directing the secretion of a flea protease protein, including fusion proteins, of the present invention. Preferred signal segments include, but are not limited to, flea protease, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a flea protease nucleic acid molecule of the present invention can enhance the stability during production, storage and/or use of the protein encoded by the nucleic acid molecule. Furthermore, a fusion segment can function as a tool to simplify purification of a flea protease protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a flea protease protein. Linkages between fusion segments and flea protease proteins can be constructed to be susceptible to cleavage to enable straightforward recovery of the flea protease proteins. Fusion proteins are preferably produced by culturing a recombinant cell transformed with a fusion nucleic acid sequence that encodes a protein including the fusion segment attached to either the carboxyl and/or amino terminal end of a flea protease protein.

A recombinant molecule of the present invention is a molecule that can include at least one of any nucleic acid molecule heretofore described operatively linked to at least: one of any transcription control sequence capable of effectively regulating expression of the nucleic acid molecules) in the cell to be transformed. A preferred recombinant molecule includes one or more nucleic acid molecules of the present invention, with those that encode one or more flea protease proteins, and particularly one or more flea serine protease proteins being more preferred. A preferred recombinant molecule of the present invention includes pTrc-nfSP33$_{1175}$, the production of which is described in the Examples section. Similarly a preferred recombinant cell includes one or more nucleic acid molecules of the present invention, with those that encode one or more flea protease proteins, and particularly one or more flea serine protease proteins being more preferred. A preferred recombinant cell of the present invention includes *E. coli:* pTrc-nfSP33$_{1175}$, the production of which is disclosed in the Examples section.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce flea protease proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a flea protease protein. Such a medium is typically an aqueous medium comprising assimilable carbohydrate, nitrogen and phosphate sources, as well as appropriate salts, minerals, metals and other nutrients, such as vitamins. The medium may comprise complex, nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant flea protease proteins may either remain within the recombinant cell; be secreted into the fermentation medium; be secreted into a space between two cellular membranes, such as the periplasmic space in *E. coli;* or be retained on the outer surface of a cell or viral membrane. Methods to purify such proteins are heretofore disclosed.

The present invention also includes isolated anti-flea protease antibodies and their use to reduce flea infestation on a host animal as well as in the environment of the animal. An anti-flea protease antibody is an antibody capable of selectively binding to a protease present in a flea midgut, including female and male fed midguts as well as female and male unfed midguts. An anti-flea protease antibody preferably binds to the protease in such a way as to reduce the proteolytic activity of that protease.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protease against which the antibody was raised (i.e., to be able to distinguish that protease from unrelated components in a mixture.). Binding affinities typically range from about $10^3$ M$^{-1}$ to about $10^{12}$ M$^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a flea protease nucleic acid molecule of the present invention.

Anti-flea antibodies of the present invention include antibodies raised in an animal administered a flea protease vaccine of the present invention that exert their effect when fleas feed from the vaccinated animal's blood containing such antibodies. Anti-flea antibodies of the present invention also include antibodies raised in an animal against one or more flea protease proteins, or soluble flea midgut preparations, of the present invention that are then recovered from the animal using techniques known to those skilled in the art. Yet additional antibodies of the present invention are produced recombinantly using techniques as heretofore disclosed for flea protease proteins of the present invention. Antibodies produced against defined proteins can be advantageous because such antibodies are not substantially contaminated with antibodies against other substances that: might otherwise cause interference in a diagnostic assay or side effects if used in a therapeutic composition.

Anti-flea protease antibodies of the present invention have a variety of uses that are within the scope of thus present invention. For example, such antibodies can be used in a composition of the present invention to passively immunize an animal in order to protect the animal from flea infestation. Anti-flea antibodies can also be used as tools to screen expression libraries and/or to recover desired proteins of the present invention from a mixture of proteins and other contaminants. Furthermore, antibodies of the present invention can be used to target cytotoxic agents to fleas in order to kill fleas. Targeting can be accomplished by conjugating (i.e., stably joining) such antibodies to the cytotoxic agents using techniques known to those skilled in the art.

A preferred anti-flea protease antibody of the present invention can selectively bind to, and preferentially reduce the proteolytic activity of, a flea serine protease, a flea metalloprotease, a flea aspartic acid protease and/or a flea cysteine protease. More preferred anti-flea protease antibodies include anti-flea serine protease antibodies. Particularly preferred are anti-flea serine protease antibodies including those raised against flea serine protease proteins of the present invention.

The present invention also includes the use of protease inhibitors that reduce proteolytic activity of flea proteases to reduce flea infestation of animals and the surrounding environment. As used herein, protease inhibitors are compounds that interact directly with a protease thereby inhibiting that protease's activity, usually by binding to or otherwise interacting with the protease's active site. Protease inhibitors are usually relatively small compounds and as such differ from anti-protease antibodies that interact with the active site of a protease.

Protease inhibitors can be used directly as compounds in compositions of the present invention to treat animals as long as such compounds are not harmful to the animals being treated. Protease inhibitors can also be used to identify preferred types of flea proteases to target using compositions of the present invention. For example, the inventors have shown herein the predominance of serine proteases in flea midguts, particularly in soluble flea midgut preparations, using protease inhibitors. Such knowledge suggests that effective reduction of flea infestation of an animal can be achieved using serine protease vaccines, anti-flea serine protease antibodies and other inhibitors of serine protease synthesis and activity that can be tolerated by the animal. That other proteases are also present in flea midguts according to the present invention also suggests targeting such proteases. Methods to use protease inhibitors are known to those skilled in the art; examples of such methods are disclosed herein.

In one embodiment, a protease inhibitor that can be used in a composition of the present invention to treat an animal is identified by a method including the following steps: (a) identifying candidate (i.e., putative, possible) inhibitor compounds by testing the efficacy of one or more protease inhibitors (i) in vitro for their ability to inhibit flea protease activity and/or (ii) in a flea feeding assay for their ability to reduce the survival and/or fecundity of fleas by adding the inhibitors to the blood meal of a flea being maintained, for example, in a feeding system, such as that described by Wade et al., 1988, *J. Med Entomol.* 25, 186–190; and (b) testing the efficacy of the candidate inhibitor compounds in animals infested with fleas. Although one does not need both in vitro assay data and flea feeding assay data to determine which candidate compounds to administer to animals, evaluation of both sets of data is preferred since data from neither of the assays necessarily predicts data to be obtained from the other assay. For example, candidate compounds identified using the in vitro assay may work "in the test tube" but may not work in vivo for a number of reasons, including the presence of interfering components in the blood meal that inhibit the activity of such compounds; e.g., although aprotinin can inhibit at least some flea serine proteases in vitro, aprotinin does not work well in the presence of serum proteins, such as are found in the blood. Furthermore, candidate inhibitor compounds identified by the flea feeding assays can include not only desired compounds but also compounds that reduce the viability and/or fecundity of fleas due to general toxicity (e.g., affecting the mitochondria of fleas).

In a preferred embodiment, an inhibitor of a flea protease of the present invention is identified by a method comprising: (a) contacting an isolated flea protease protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47 with a putative inhibitory compound under conditions in which, in the absence of the compound, the protein has proteolytic activity; and (b) determining if the putative inhibitory compound inhibits the activity. A test kit can be used to perform such method. A preferred test kit comprises an isolated flea protease protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47, and a means for determining the extent of inhibition of the activity in the presence of a putative inhibitory comp In another embodiment, protease inhibitors are used in the purification of corresponding proteases by, for example, affinity chromatography, in which, a protease inhibitor is incubated with a mixture containing a desired protease under conditions that the inhibitor forms a complex with the protease. The protease can then be recovered from the complex. The protease inhibitor can be attached to a solid support and/or be labeled with, for example, a radioactive, fluorescent, or enzymatic tag that can be used to detect and/or recover the complex.

Suitable protease inhibitors to use in accordance with the present invention include serine protease inhibitors (including IgGase inhibitors), metalloprotease inhibitors, aspartic acid protease inhibitors, cysteine protease inhibitors and aminopeptidase inhibitors. Preferred protease inhibitors include serine protease inhibitors, metalloprotease inhibitors, aminopeptidase inhibitors and cysteine protease inhibitors, particularly those that are broad spectrum inhibitors. More preferred are broad spectrum serine protease inhibitors.

There is a wide variety of protease inhibitors, as is known to one skilled in the art. Examples include, but are not limited to, AEBSF, aprotinin, bestatin, chloromethyl ketones TLCK (Na-p-tosyl-L-lysine chloromethyl ketone) and TPCK (N-tosyl-L-phenylalanine chloromethyl ketone), chymostatin, cystatin, 3'4-dichloroisocoumarin, E-64 (trans-epoxysuccinyl-L-leucylamido-(4-guanidino)butane), EDTA (ethylenediaminetetraacetic acid), leupeptin, methyl ketones having a variety of leaving groups, oxidized L-leucinethiol, pepstatin, 1,10-orthophenanthroline, phosphoramidon, soybean trypsin/chymotrypsin inhibitor and soybean trypsin inhibitor. Preferred protease inhibitors for use in the present invention include AEBSF, bestatin, E-64 leupeptin, pepstatin, 1,10-orthophenanthroline, phosphoramidon, TLCK and TPCK, with AEBSF (a broad spectrum serine protease inhibitor), bestatin (an inhibitor of leucine aminopeptidase) and 1,10-orthophenanthroline (a broad spectrum metalloprotease inhibitor) being particularly preferred.

Another preferred inhibitor of the present invention includes an inhibitor of an immunoglobulin protease of the present invention. Suitable inhibitors of immunoglobulin protease activity are compounds that interact directly with an immunoglobulin protease protein's active site, thereby inhibiting that immunoglobulin protease's activity, usually by binding to or otherwise interacting with or otherwise modifying the immunoglobulin protease's active site. Immunoglobulin protease inhibitors can also interact with other regions of the immunoglobulin protease protein to inhibit immunoglobulin protease activity, for example, by allosteric interaction. Inhibitors of immunoglobulin proteases are usually relatively small compounds and as such differ from anti-immunoglobulin protease antibodies. Preferably, an immunoglobulin protease inhibitor of the present invention is identified by its ability to bind to, or otherwise interact with, a flea immunoglobulin protease protein, thereby inhibiting the activity of the flea immunoglobulin protease.

Preferred immunoglobulin protease inhibitors of the present invention include, but are not limited to, flea immunoglobulin protease substrate analogs, and other molecules that bind to a flea immunoglobulin protease (e.g., to an allosteric site) in such a manner that protease activity of the flea immunoglobulin protease is inhibited. An immunoglobulin protease substrate analog refers to a compound that interacts with (e.g., binds to, associates with, modifies) the active site of an immunoglobulin protease protein. A preferred immunoglobulin protease substrate analog inhibits immunoglobulin protease activity. Immunoglobulin protease substrate analogs can be of any inorganic or organic composition, and, as such, can be, but are not limited to, peptides, nucleic acids, and peptidomimetic compounds. Immunoglobulin protease substrate analogs can be, but need not be, structurally similar to an immunoglobulin protease's natural substrate as long as they can interact with the active site of that protease protein. Immunoglobulin protease substrate analogs can be designed using computer-generated structures of immunoglobulin protease proteins of the present invention or computer structures of immunoglobulin proteases' natural substrates. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea immunoglobulin protease).

Protease inhibitors can be produced using methods known to those skilled in the art. Protein- or peptide-based protease inhibitors, such as cystatin or small peptides comprising a protease substrate, can be produced recombinantly and modified as necessary.

The present invention also includes the use of proteolytically active flea protease proteins of the present invention to identify additional protease inhibitors, and preferably protease inhibitor compounds that can be included in a composition of the present invention to be administered to animals. A method to identify a flea protease inhibitor includes the steps of (a) contacting (e.g., combining, mixing) an isolated flea protease protein with a putative (i.e., candidate) inhibitory compound under conditions in which, in the absence of the compound, the protein has proteolytic activity, and (b) determining if the putative inhibitory compound inhibits the proteolytic activity of the protein. Putative inhibitory compounds to screen include organic molecules, antibodies (including functional equivalents thereof) and substrate analogs. Methods to determine protease activity are known to those skilled in the art, as heretofore disclosed. Particularly preferred for use in identifying inhibitors are flea serine protease proteins of the present invention.

The present invention also includes a test kit to identify a compound capable of inhibiting flea protease activity. Such a test kit includes an isolated flea protease protein having proteolytic activity and a means for determining the extent of inhibition of proteolytic activity in the presence of (i.e., effected by) a putative inhibitory compound.

The present invention also includes inhibitors isolated by such a method, and/or test kit, and their use to inhibit any flea protease that is susceptible to such an inhibitor.

It is to be appreciated that the present invention also includes mimetopes of compounds of the present invention that can be used in accordance with methods as disclosed for compounds of the present invention. As used herein, a mimetope of a proteinaceous compound of the present invention (e.g., a flea protease protein, an anti-flea protease antibody, a proteinaceous inhibitor of protease activity or synthesis) refers to any compound that is able to mimic the activity of that proteinaceous compound, often because the mimetope has a structure that mimics the proteinaceous compound. For example, a mimetope of a flea protease protein is a compound that has an activity similar to that of an isolated flea protease protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

The present invention includes therapeutic compositions, also referred to herein as compositions, that include a (i.e., at least one) compound of the present invention. Preferred compounds to include in a composition of the present invention include flea protease vaccines, anti-flea protease antibodies and/or protease inhibitors as disclosed herein. Such a therapeutic composition can protect an animal from flea infestation by reducing flea protease activity, thereby reducing flea burden on the animal and in the environment of the animal.

Particularly preferred therapeutic compositions of the present invention include at least one of the following compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein and an inhibitor of flea serine protease activity identified by its ability to inhibit flea serine protease activity.

Another embodiment of the present invention is a therapeutic composition that includes a first compound that reduces flea protease activity and a second compound that reduces flea burden by a method other than by reducing flea protease activity. The present invention also includes a method to protect an animal from flea infestation by administering to the animal such a composition. The first compound of such a composition by effectively reducing flea protease activity in the midgut, enhances the activity of the second compound. While not being bound by theory, it is believed that a number of anti-flea treatments, particularly those that are proteinaceous, are not very effective because they are degraded in the flea midgut. The present invention permits the effective use of such anti-flea treatments by reducing proteolytic degradation of such treatments by the flea midgut.

Preferred first compounds to include in such a composition include flea protease vaccines, anti-flea protease antibodies and/or protease inhibitors as disclosed herein.

A preferred therapeutic composition of the present invention comprises an excipient and a protective compound including: an isolated protein or mimetope thereof encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47; an isolated nucleic acid molecule that hybridizes under stringent hybridization conditions with a gene comprising a nucleic acid sequence including SEQ ID NO:7, SEQ ID NO:23, SEQ ID NO:28, SEQ ID NO:33, SEQ ID NO:38, SEQ ID NO:43, and/or SEQ ID NO:48, an isolated antibody that selectively binds to a protein encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47; an inhibitor of protease activity identified by its ability to inhibit the activity of a protein encoded by a nucleic acid molecule that hybridizes under stringent hybridization conditions with a nucleic acid molecule having a nucleic acid sequence encoding a protein comprising an amino acid sequence including SEQ ID NO:8, SEQ ID NO:22, SEQ ID NO:27, SEQ ID NO:32, SEQ ID NO:37, SEQ ID NO:42 and/or SEQ ID NO:47; and a mixture thereof.

Suitable second compounds include any anti-flea agent(s), including, but not limited to, proteinaceous compounds, insecticides and flea collars. Preferred second compounds are proteinaceous compounds that effect active immunization (e.g., antigen vaccines), passive immunization (e.g., antibodies), or that otherwise inhibit a flea activity that when inhibited can reduce flea burden on and around an animal. Examples of second compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system and/or a compound that inhibits flea feeding.

Compositions of the present invention can also include other components such as a pharmaceutically acceptable excipient, an adjuvant, and/or a carrier. For example, compositions of the present invention can be formulated in an excipient that the animal to be treated can tolerate.

Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (available from Vaxcell, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release: formulations, biodegradable implants, liposomes, bacteria, viruses, oils, esters, and glycols.

One embodiment of the present invention is a controlled release formulation that is capable of slowly releasing a composition of the present invention into an animal. As used herein a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to reduce protease activity in fleas feeding from the animal over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from flea infestation, a therapeutic composition of the present invention is administered to the animal in an effective manner such that the protease activity of fleas feeding from the blood stream of animals treated with the composition is reduced. As such, a treated animal is an animal that is competent to reduce the flea burden by reducing flea protease activity, or by reducing flea protease activity and at least one other flea activity. Preferably, the protease activity is reduced by at least about 50 percent, more preferably by at least about 70 percent and even more preferably by at least about 90 percent. Methods to administer compositions to the animal in order to render the animal competent depend on the nature of the composition and administration regime. Animals administered a protease vaccine with at least one booster shot usually become competent at about the same time as would be expected for any vaccine treatment. For example, animals administered a booster dose about 4 to 6 weeks after a primary dose usually become competent within another about 3 to 4 weeks. Animals administered a composition including an anti-flea protease antibody or protease inhibitor become competent as soon as appropriate serum levels of the compound are achieved, usually with one to three days.

In a preferred embodiment, a composition of the present invention when administered to a host animal is able to reduce flea viability by at least about 50 percent within at least about 21 days after the fleas begin feeding from the treated animal. (Note that fleas usually live about 40 days to about 50 days on one or more animals.) A more preferred composition when administered to a host animal is able to reduce flea viability by at least about 65 percent within at least about 14 days after the fleas begin feeding from the treated animal. An even more preferred composition when administered to an animal is able to reduce flea viability by at least about 90 percent within at least about 7 days after the fleas begin feeding from the treated animal.

In another preferred embodiment, a composition of the present invention when administered to a host animal is able to reduce flea fecundity (i.e., egg laying ability) by at least about 50 percent, more preferably by at least about 70 percent, and even more preferably by at least about 90 percent, within at least about 30 days after the fleas begin feeding from the treated animal. (Note that fleas usually do not begin laying eggs until about 7 days after taking a blood meal.)

In accordance with the present invention, compositions are administered to an animal in a manner such that the animal becomes competent to reduce flea protease activity in a flea in that feeds from the competent; i.e., the animal becomes a treated animal. For example, a flea protease vaccine of the present invention, when administered to an animal in an effective manner, is able to elicit (i.e., stimulate) an immune response that produces an antibody titer in the blood stream of the animal sufficient to reduce flea protease activity. Similarly, an anti-flea protease antibody of the present invention, when administered to an animal in an effective manner, is administered in an amount so as to be present in the animal's blood stream at a titer that is sufficient to reduce flea protease activity. A protease inhibitor compound of the present invention, when administered to an animal in an effective manner, is administered in a manner so as to be present in the animal's blood stream at a concentration that is sufficient to reduce flea protease activity. Oligonucleotide nucleic acid molecules of the present invention can also be administered in an effective manner, thereby reducing expression of flea proteases.

Compositions of the present invention can be administered to animals prior to or during flea infestation. It is to be noted that when vaccines of the present invention are administered to an animal, a time period is required for the animal to elicit an immune response before the animal is competent to inhibit protease activity of fleas feeding from that animal. Methods to obtain an immune response in an animal are known to those skilled in the art.

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from flea infestation when administered one or more times over a suitable time period. For example, a preferred single dose of a protease vaccine or a mimetope thereof ranges from about 1 microgram ($\mu$g, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from flea infestation. A preferred administration schedule is one in which from about 10 $\mu$g to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-flea protease antibody composition or a mimetope thereof ranges from about 1 $\mu$g to about 10 mg of the composition per kilogram body weight of the animal. Anti-flea antibodies can be re-administered from about 1 hour to about biweekly for several weeks following the original administration. Booster treatments preferably are administered when the titer of antibodies of the animal becomes insufficient to protect the animal from flea infestation. A preferred administration schedule is one in which from about 10 $\mu$g to about 1 mg of an anti-flea protease antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein (e.g., flea protease vaccine, anti-flea protease antibody, or proteinaceous protease inhibitor) or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, Science 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. A preferred single dose of a recombinant virus particle vaccine of the present invention is from about $1\times10^4$ to about $1\times10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, E. coli, Mycobacterium, S. frugiperda, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

Compositions of the present invention can be administered to any animal susceptible to flea infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

The present invention includes compositions to treat flea infestation by any flea. As such, compositions of the present invention can be derived from any flea species. Preferred fleas to target include fleas of the following genera: Ctenocephalides, Cyopsyllus, Diamanus (Oropsylla), Echidnophaga, Nosopsyllus, Pulex, Tunga, and Xenopsylla, with those of the species Ctenocephalides canis, Ctenocephalides felis, Diamanus montanus, Echidnophaga gallinacea, Nosopsyllus faciatus, Pulex irritans, Pulex simulans, Tunga penetrans and Xenopsylla cheopis being more preferred. Particularly preferred fleas from which to protect animals include fleas of the species Ctenocephalides felis, Ctenocephalides canis, and Pulex species (e.g., Pulex irritans and Pulex simulans). It is also within the scope of the present invention to administer compositions of the present invention directly to fleas.

The present invention also includes the use of compositions of the present invention to reduce infestation by other ectoparasites as well as the use of compositions including protease vaccines, anti-protease antibodies and compounds that inhibit protease synthesis and/or activity derived from any ectoparasite to reduce ectoparasite infestation, particularly controlled release formulations containing such compositions. Preferred ectoparasites to target include arachnids, insects and leeches. More preferred ectoparasites to target include fleas; ticks, including both hard ticks of the family Ixodidae (e.g., Ixodes and Amblyomma) and soft ticks of the family Argasidae (e.g., Ornithodoros, such as O. parkeri and O. turicata); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred Uni-ZAPIXR vector (available from Stratagene Cloning Systems) using Stratagene's ZAP-cDNA Synthesis Kit® protocol. About 6.34 µg of mixed instar poly A+RNA were used to produce the mixed instar library and about 6.72 µg of wandering larvae poly A+RNA were used to produce the wandering larvae library. The resultant mixed instar library was amplified to a titer of about $2.17\times10^{10}$ pfu/ml with about 97% recombinants. The resultant wandering larvae library was amplified to a titer of about $3.5\times10^{10}$ pfu/ml with about 97% recombinants.

Example 2

This example provides additional nucleic acid and deduced amino acid sequences of nucleic acid molecules encoding serine protease proteins of the present invention which are described herein and in the Examples section of related PCT Publication Nos. WO 96/11706 and WO 97/40058.

A. Clone 33

Additional sequence of flea serine protease nucleic molecule clone 33 was determined using primers designed from nfSP33$_{778}$ to isolate DNA using polymerase chain reaction amplification (PCR) from the flea mixed instar larvae cDNA library described in Example 8 of PCT Publication No. WO 97/40058. Sense primer Flea 33F having the nucleotide sequence 5' CAG GGC GCT CTG CAG AAC GCA AC 3' (denoted SEQ ID NO:1) was used in combination with the M13 universal primer in a first PCR reaction. Anti-sense primer Flea 33R having the nucleotide sequence 5' ATT CCT CGT GGT TCA GTC GCT C $_3$' (denoted SEQ ID NO:2) was used in combination with the M13 reverse primer in a second PCR reaction. The resulting PCR products were each gel purified and cloned into the TA Vector® System, and subjected to standard DNA sequencing techniques. A composite nucleic acid sequence representing a flea serine protease coding region, referred to herein as nfSP33$_{1894}$, was deduced and is denoted herein as SEQ ID NO:3.

A DNA probe was generated by PCR amplifying nfSP33$_{1894}$ (SEQ ID NO:3) using the forward primer 33FE, (denoted SEQ ID NO:4), having the nucleotide sequence 5' CAA AGG ATC CCA TGC CAA CCC TCG TGG AGT TGA TGT GTC 3' and the reverse primer Stubble R, (denoted SEQ ID NO:5), having the nucleotide sequence 5' ATT CCT CGT GGT TCA GTC GCT C 3'. The resulting PCR fragment was approximately 678 bp in length, and corresponded to nucleotides 334–1012 of SEQ ID NO:3 and is referred to herein as nfSP33$_{678}$.

Nucleic acid molecule nfSP33$_{679}$ was labeled with $^{32}$p and used to screen the flea mixed instar larval cDNA library described above in Example 1 using standard hybridization techniques. A clone was isolated having about a 1373 nucleotide insert, referred to herein as nfSP33$_{1373}$, having a nucleic acid sequence denoted herein as SEQ ID NO:6, and a complementary strand denoted herein as SEQ ID NO:7. Portions of sequence of SEQ ID NO:6 are contained in SEQ ID NO:3 ectoparasites to target include fleas, mosquitos, midges, sandflies, blackflies, ticks and Rhodnius.

The following examples are provided for the purposes of illustration and are not intended to limit the scope of the present invention.

EXAMPLES

Example 1

A flea mixed instar cDNA library was produced using unfed 1st instar, bovine blood-fed 1st instar, bovine blood-fed $2^{nd}$ nd instar and bovine blood-fed $3^{rd}$ instar flea larvae (this combination of tissues is referred to herein as mixed instar larval tissues for purposes of this example). A flea wandering larvae cDNA library was produced using wandering flea larvae. For each library, total RNA was extracted from mixed instar or wandering larvae tissue, respectfully, using an acid-guanidinium-phenol-chloroform method similar to that described by Chomczynski et al., 1987, *Anal. Biochem.* 162, p. 156–159. Approximately 5,164 mixed instar larvae or 3,653 wandering larvae were used in each RNA preparation. Poly A+ selected RNA was separated from each total RNA preparation by oligo-dT cellulose chromatography using Poly(A)Quick® mRNA isolation kits (available from Stratagene Cloning Systems, La Jolla, Calif.), according to the method recommended by the manufacturer.

A mixed instar cDNA expression library and a wandering larvae cDNA expression library were constructed in lambda (λ.)

Translation of SEQ ID NO:6 suggests that nucleic acid molecule nfSP33$_{1373}$ encodes a full-length protein of about 387 amino acids, referred to herein as PfSP33$_{387}$, having an amino acid sequence represented by SEQ ID NO:8, assuming the initiation codon spans from nucleotide 199 through nucleotide 201 of SEQ ID NO: 6 and the termination codon spans from nucleotide 1360 through nucleotide 1362 of SEQ ID NO:6. The coding region encoding PfSP33$_{387}$ is represented by nucleic acid molecule nfSP33$_{1161}$, having a coding strand with the nucleic acid sequence represented by SEQ ID NO:9 and a complimentary strand with nucleic acid sequence SEQ ID NO:10. Comparison of nucleic acid sequence SEQ ID NO:6 with nucleic acid sequences reported in GenBank indicates that SEQ ID NO:6 showed the most homology, i.e., about 38% identity between SEQ ID NO:6 and a serine protease stubble from Drosophila melanogaster.

A PCR fragment was generated from nucleic acid molecule nfSP33$_{1373}$ using the forward primer 33FE, (SEQ ID NO:4) and the reverse primer 33RE, denoted SEQ ID NO:11, having the nucleotide sequence 5' CCG GAA TTC TTA TCC CAT TAC TTT GTC GAT CC 3'. The resulting PCR fragment, referred to herein as nfSP33$_{1175}$, was gel purified, digested with the restriction endonucleases BamHI and EcoRI, and ligated into the plasmid pTrcHisB, which had been digested with the same endonucleases, to produce a recombinant molecule referred to herein as pTrc-nfSP33$_{1175}$. Standard DNA sequencing was performed. The coding sequence is denoted herein by SEQ ID NO:12 and the complementary strand is represented herein by SEQ ID NO:14. Translation of SEQ ID NO:12 indicates that the nucleic acid molecule nfSP33$_{1175}$ encodes a full -length serine protease protein of about 382 amino acids, referred to herein as PfSP$^{33}$382, having amino acid sequence SEQ ID NO:13, assuming the initiation codon spans from nucleotide 1 through nucleotide 3 of SEQ ID NO:12 and the termination codon spans from nucleotide 1162 through nucleotide 1164 of SEQ ID NO:12. The coding region encoding PfSP33$_{382}$, is represented by nucleic acid molecule nfSP33$_{1161}$, having a coding strand with the nucleic acid sequence represented by SEQ ID NO:15 and a complementary strand having nucleic acid sequence represented by SEQ ID NO:16. The amino acid sequence of PfSP33$_{382}$ predicts that PfSP33$_{382}$ has an estimated molecular weight of about 46.3 kDa, and a pI of about 6.73. Comparison of amino acid sequence SEQ ID NO:13 with amino acid sequences reported in GenBank indicates that SEQ ID NO:13 showed the most homology, i.e., about 29% identity, with a serine protease stubble protein from Drosophila melanogaster. Comparison of nucleic acid sequence SEQ ID NO:12 with nucleic acid sequences reported in GenBank indicates that SEQ ID NO:12 showed the most homology, i.e., about 44% identity, with a serine protease stubble gene from *Drosophila melanogaster.*

The recombinant molecule pTrc-nfSP33$_{1175}$ was transformed into *E. coli* BL-21 competent cells to form recombinant cells *E. coli*:pTrc-nfSP33$_{1175}$. The recombinant cells were cultured and induced 0.25 mM IPTG. Recombinant protein production was determined by collecting about 1 ml of culture prior to induction, and about 1 ml of culture about 60 minutes following induction. These samples were then lysed in sodium dodecyl sulfate polyacrylamide gel electrophoresis (SDS-PAGE) loading buffer and resolved on a 14% Tris-glycine acrylamide gel. Immunoblot analysis of the proteins using a T7 (tag) antibody (available from Novagen) showed expression of an about 55 kD protein in the induced sample but not in the uninduced sample.

P B. Clone 8

A flea serine protease cDNA nucleic acid molecule was isolated in a manner similar to that described in Example 8 of related PCT Publication No. WO 96/11706, using two nucleic acid molecules as probes to screen a bovine blood-fed flea cDNA expression library (produced as described in Example 8 of related PCT Publication No. WO 96/11706), cat-try #1 (SEQ ID NO:17) and cat-try #2 (SEQ ID NO:18). A clone that hybridized strongly to the probes was isolated and subjected to nucleic acid sequencing using standard sequencing techniques. The nucleic acid sequence of a flea serine protease nucleic acid molecule correlating to flea clone 8, namely nfSP8$_{436}$, is represented herein as SEQ ID NO:19.

Nucleic acid molecule nfSP8$_{436}$ was further sequenced using standard sequencing methods as follows. Reverse primer Snake (denoted SEQ ID NO:20 and having a sequence 5' AAC TAT CTG TGT CGA ACT CGT C 3', that corresponds to nucleotides 47–68 of SEQ ID NO:19) was used in combination with forward vector primer M13 rev (denoted SEQ ID NO:21, having a sequence 51 GGA AAC AGC TAT GAC CAT G 3') to produce a PCR product, using standard PCR methods, of about 1100 nucleotides from the mixed instar larvae library and the wandering larval library described above in Example 1. The resulting PCR products from each library were combined, purified and ligated into the TA vector pCR II (available from Invitrogen, La Jolla, Calif.). One clone, referred to herein as nfSP8$_{1100}$, was sequenced using standard methods.

The nucleic acid sequences of nfSP8$_{1100}$ and nfSP8$_{436}$ were aligned and a contiguous nucleic acid sequence was derived and is denoted herein as nfSP8$_{1303}$. The resulting contiguous sequence of nfSP8$_{1303}$ is denoted herein as SEQ ID NO:21 and the complement is denoted herein as SEQ ID NO:23. Translation of SEQ ID NO:21 suggests that the nucleic acid molecule nfSP8$_{1303}$ encodes a full-length flea serine protease protein of 384 amino acids, referred to herein as PfSP8$_{384}$, having amino acid sequence represented by SEQ ID NO:22, assuming the initiation codon spans from nucleotide 149 through nucleotide 151 of SEQ ID NO:21 and the termination codon spans from nucleotide 1301 through nucleotide 1303 of SEQ ID NO:21. The coding region encoding PfSP8$_{384}$, is represented by nucleic acid molecule nfSP8$_{1152}$, having a coding strand with the nucleic acid sequence represented by SEQ ID NO:24 and a complementary strand having nucleic acid sequence represented by SEQ ID NO:25. The amino acid sequence of PfSP8$_{384}$ predicts that PfSP8$_{384}$ has an estimated molecular weight of about 42.2 kDa, and a pI of about 5.0. Comparison of amino acid sequence SEQ ID NO:22 with amino acid sequences reported in GenBank indicates that SEQ ID NO:22 showed the most homology, i.e., about 39% identity, with a serine protease snake protein from *Drosophila melanogaster.* Comparison of nucleic acid sequence SEQ ID NO:21 with nucleic acid sequences reported in GenBank indicates that SEQ ID NO:21 showed the most homology, i.e., about 35% identity, with a serine protease snake gene from *Drosophila melanogaster.*

C. Clone 2

Flea serine protease nucleic acid molecule nfSP2$_{945}$ was produced as described in Example 18 of PCT Publication No. WO 96/11706. Nucleic acid molecule nfSP2$_{945}$ was re-sequenced, the nucleic acid sequence of which is denoted herein as SEQ ID NO:26 and the complement of which is denoted SEQ ID NO:28. Translation of SEQ ID NO:26 suggests that nfSP2$_{945}$ encodes a non-full-length serine protease protein referred to herein as PfSP2$_{256}$, the amino acid sequence of which is denoted herein as SEQ ID NO:27, assuming an open reading frame in which the first codon spans from nucleotide 1 through nucleotide 3 of SEQ ID NO:26 and the termination codon spans from nucleotide 769 through nucleotide 771 of SEQ ID NO:26. The coding region encoding PfSP2$_{256}$, is represented by nucleic acid molecule nfSP2$_{768}$, having a coding strand with the nucleic acid sequence represented by SEQ ID NO:29 and a complementary strand with nucleic acid sequence SEQ ID NO:30. Comparison of amino acid sequence SEQ ID NO:27 with amino acid sequences reported in GenBank indicates that SEQ ID NO:27 showed the most homology, i.e., about 42% identity, with a *Bombix mori* vitellin-degrading enzyme. Comparison of nucleic acid sequence SEQ ID NO:26 with nucleic acid sequences reported in GenBank indicates that SEQ ID NO:26 showed the most homology, i.e., about 45% identity, with a *Bombix mori* vitellin-degrading enzyme gene.

D. Clone 6

Flea serine protease nucleic acid molecule nfSP6$_{932}$, was produced as described in Example 18 of PCT Publication No. WO 96/11706. Nucleic acid molecule nfSP6$_{932}$ was re-sequenced, the nucleic acid sequence of which is denoted herein as SEQ ID NO:31 and the complement of which is denoted SEQ ID NO:33. Translation of SEQ ID NO:31 suggests that nfSP6$_{932}$ encodes a non-full-length serine protease protein referred to herein as PfSP6$_{256}$, the amino acid sequence of which is denoted herein as SEQ ID NO:32, assuming an open reading frame in which the first codon spans from nucleotide 2 through nucleotide 4 of SEQ ID NO:31 and the termination codon spans from nucleotide 770 through nucleotide 772 of SEQ ID NO:31. The coding region encoding PfSP6$_{256}$, is represented by nucleic acid molecule nfSP6$_{768}$, having a coding strand with the nucleic acid sequence represented by SEQ ID NO:34 and a complementary strand with nucleic acid sequence SEQ ID NO:35. Comparison of amino acid sequence SEQ ID NO:32 with amino acid sequences reported in GenBank indicates that SEQ ID NO:32 showed the most homology, i.e., about 41% identity, with an *Anopheles stepheni* trypsin protein. Comparison of nucleic acid sequence SEQ ID NO:31 with nucleic acid sequences reported in GenBank indicates that SEQ ID NO:31 showed the most homology, i.e., about 50% identity, with an *Anopheles stepheni* trypsin gene.

E. Clone 20

Flea serine protease nucleic acid molecule nfSP20$_{841}$, was produced as described in Example 18 of PCT Publication No. WO 96/11706. Nucleic acid molecule nfSP20$_{841}$ was re-sequenced, the nucleic acid sequence of which is denoted herein as SEQ ID NO:36 and the complement of which is denoted SEQ ID NO:38. Translation of SEQ ID NO:36 suggests that nfSP20$_{841}$ encodes a non-full-length serine protease protein referred to herein as PfSP20$_{248}$, the amino acid sequence of which is denoted herein as SEQ ID NO:37, assuming an open reading frame in which the first codon spans from nucleotide 2 through nucleotide 4 of SEQ ID NO:36 and the termination codon spans from nucleotide 746 through nucleotide 748 of SEQ ID NO:36. The coding region encoding PfSP20$_{248}$, is represented by nucleic acid molecule nfSP20$_{744}$, having a coding strand with the nucleic acid sequence represented by SEQ ID NO:39 and a complementary strand with nucleic acid sequence SEQ ID NO:40. Comparison of amino acid sequence SEQ ID NO:37 with amino acid sequences reported in GenBank indicates that SEQ ID NO:37 showed the most homology, i.e., about 50% identity, with a *Culex pipiens* quinquefasciatus protein. Comparison of nucleic acid sequence SEQ ID NO:36 with nucleic acid sequences reported in GenBank indicates that SEQ ID NO:36 showed the most homology, i.e., about 54% identity, with a nucleic acid molecule encoding a *Culex pipiens* quinquefasciatus gene.

F. Clone 32

Flea serine protease nucleic acid molecule nfSP32$_{933}$, was produced as described in Example 21 of PCT Publication No. WO 97/40058. Nucleic acid molecule nfSP32$_{933}$ was re-sequenced, the nucleic acid sequence of which is denoted herein as SEQ ID NO:41 and the complement of which is denoted SEQ ID NO:43. Translation of SEQ ID NO:41 suggests that nfSP32$_{933}$ encodes a full-length serine protease protein referred to herein as PfSP32$_{268}$, the amino acid sequence of which is denoted herein as SEQ ID NO:42, assuming an open reading frame in which the initiation codon spans from nucleotide 6 through nucleotide 8 of SEQ ID NO:41 and the termination codon spans from nucleotide 810 through nucleotide 812 of SEQ ID NO:41. The coding region encoding PfSP32$_{268}$, is represented by nucleic acid molecule nfSP32$_{804}$, having a coding strand with the nucleic acid sequence represented by SEQ ID NO:44 and a complementary strand with nucleic acid sequence SEQ ID NO:45. Comparison of amino acid sequence SEQ ID NO:42 with amino acid sequences reported in GenBank indicates that SEQ ID NO:42 showed the most homology, i.e., about 44% identity, with a *Fusariam oxysporum* protein. Comparison of nucleic acid sequence SEQ ID NO:41 with nucleic acid sequences reported in GenBank indicates that SEQ ID NO:41 showed the most homology, i.e., about 47% identity, with a nucleic acid molecule encoding a *Fusariam oxysporum* gene.

G. Clone 40

Flea serine protease nucleic acid molecule nfSP40$_{841}$, was produced as described in Example 22 of PCT Publication No. WO 97/40058. Nucleic acid molecule nfSP40$_{841}$ was re-sequenced, the nucleic acid sequence of which is denoted herein as SEQ ID NO:46 and the complement of which is denoted SEQ ID NO:48. Translation of SEQ ID NO:46 suggests that nfSP40$_{841}$ encodes a non-full-length serine protease protein referred to herein as PfSP40$_{242}$, the amino acid sequence of which is denoted herein as SEQ ID NO:47, assuming an open reading frame in which the first codon spans from nucleotide 2 through nucleotide 4 of SEQ ID NO:46 and the termination codon spans from nucleotide 728 through nucleotide 730 of SEQ ID NO:46. The coding region encoding PfSP40$_{242}$, is represented by nucleic acid molecule nfSP40$_{726}$, having a coding strand with the nucleic acid sequence represented by SEQ ID NO:49 and a complementary strand with nucleic acid sequence SEQ ID NO:50. Comparison of nucleic acid sequence SEQ ID NO:46 with nucleic acid sequences reported in GenBank indicates that SEQ ID NO:46 showed the most homology, i.e., about 57% identity, with a *Dermatophagoides pteronyssinus* Der P3 allergen gene. Comparison of amino acid sequence SEQ ID NO:47 (i.e., the amino acid sequence of PfSP40$_{242}$) with amino acid sequences reported in GenBank indicates that SEQ ID NO:47 showed the most homology, i.e., about 40% identity, with a *Bombyx mori* vitellin-degrading protease precursor protein.

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
       (A) LENGTH: 23 nucleotides
       (B) TYPE: nucleic acid
       (C) STRANDEDNESS: single
       (D) TOPOLOGY: linear (ii) MOLECULE TYPE: Primer (xi) SEQUENCE DESCRIPTION: SEQ ID NO:1:

```
CAGGGCGCTC TGCAGAACGC AAC                                             23
```

(2) INFORMATION FOR SEQ ID NO:2:

(i) SEQUENCE CHARACTERISTICS:
       (A) LENGTH: 22 nucleotides
       (B) TYPE: nucleic acid
       (C) STRANDEDNESS: single
       (D) TOPOLOGY: linear (ii) MOLECULE TYPE: Primer (xi) SEQUENCE DESCRIPTION: SEQ ID NO:2:

```
ATTCCTCGTG GTTCAGTCGC TC                                              22
```

(2) INFORMATION FOR SEQ ID NO:3:

(i) SEQUENCE CHARACTERISTICS:
       (A) LENGTH: 1894 nucleotides
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 335..1534

(xi) SEQUENCE DESCRIPTION: SEQ ID NO:3:

```
ACGCGACGGG CAGTCTCTTT CAGACCGCGG CCGAACGATG TTTTTGACGG                50

TTTAATTTCA ATTTTTGCAA CTTGTGACTT CGAATACACC CGTACGTGAC               100

CTATCCACTT TACCATCGGC CGACCGTGAA AGTTGTGTTT GTGCTATTGA               150

AAATTTCGTG CTCAATAATA AATATTCAGT TTTTTTGTCT AATCAGGATA               200

TTTAAATTTA TGTGTACAAG TGTTAAACGC AATCTCGTCG CTCTTCCTAA               250

TTTTCTTGTT GCCAATGCTG GCCTCAGTGC ATCGGCCGAC GCAAATGTGC               300

TTGCAAAATA GAGAAATCCG GTGAAATCAC A CAT ATG TTA GCG ATC               346
                                   Met Leu Ala Ile
                                     1

TCA AAC GGA GCG TTC GCA GAC CAT GCC AAC CTT GGT GGA GTT              388
Val Pro Ser Asn Gly Ala Phe Ala Asp His Ala Asn Leu Gly
 5              10                  15

GAT GGT GTC CCG CTT TCT GGT TTG ATT CTG GTC GCT GTT GCG              430
Gly Val Asp Gly Leu Ser Gly Leu Ile Leu Val Ala Val Ala
   20              25                  30
```

```
                                        -continued

ATA TCT TCG ATT GGA TAT GCG GAC GCG GCG AAC GTT GCG CAG          472
Ile Ser Ser Ile Gly Tyr Ala Asp Ala Ala Asn Val Ala Gln
     35              40                  45

GAC GGA CAT CCG TCC AGC CAG CAA GAG CAG GAG ATC CTG CTG          514
Asp Gly His Pro Ser Ser Gln Gln Glu Gln Glu Ile Leu Leu
             50              55                      60

CTG AAT GCC TTA GCT CGC AGG AAC GGA GCG ACG GGG CAC CAA          556
Leu Asn Ala Leu Ala Arg Arg Asn Gly Ala Thr Gly His Gln
                 65                  70

TTT GAC GTA GAT CAA GAT TCA ATT ATG GAT ATG CTA GGA AGA          598
Phe Asp Val Asp Gln Asp Ser Ile Met Asp Met Leu Gly Arg
 75                  80                  85

ATG ATA CCT CAG ACT TGC CGG TAC AAA GGC GAA CGG TTC GAG          640
Met Ile Pro Gln Thr Cys Arg Tyr Lys Gly Glu Arg Phe Glu
         90                  95             100

TGC GGT TTG TCA ATT TCG TGC GTC CTG GGC GGC GGA AAA CCT          682
Cys Gly Leu Ser Ile Ser Cys Val Leu Gly Gly Gly Lys Pro
             105                 110                 115

CTT GAC CTG TGC AGC GGC GGA ATG ATC TGG TCG TGC TGC GTC          724
Leu Asp Leu Cys Ser Gly Gly Met Ile Trp Ser Cys Cys Val
                 120                 125                 130

GAC AGG GAC ATT CGG CCT GAG CCG CAG CAC CAG GGC GCT CTG          766
Asp Arg Asp Ile Arg Pro Glu Pro Gln His Gln Gly Ala Leu
                     135                 140

CAG AAC GCA ACT TGT GGA GAA TTG TAC ACG AGG TCT AAT AGA          808
Gln Asn Ala Thr Cys Gly Glu Leu Tyr Thr Arg Ser Asn Arg
145                 150                 155

ATC GTA GGA GGT CAT TCA ACA GGA TTC GGG TCT CAT CCT TGG          850
Ile Val Gly Gly His Ser Thr Gly Phe Gly Ser His Pro Trp
     160                 165                 170

CAG GCG GCT TTG ATC AAA TCA GGA TTT TTG AGT AAA AAA TTA          892
Gln Ala Ala Leu Ile Lys Ser Gly Phe Leu Ser Lys Lys Leu
             175                 180                 185

TCT TGC GGT GGC GCT TTA GTT AGC GAT CGA TGG GTT ATA ACT          934
Ser Cys Gly Gly Ala Leu Val Ser Asp Arg Trp Val Ile Thr
                 190                 195                 200

GCT GCA CAT TGC GTT GCC ACG ACA CCA AAT TCG AAC CTG AAG          976
Ala Ala His Cys Val Ala Thr Thr Pro Asn Ser Asn Leu Lys
                     205                 210

GTG CGA TTG GGC GAA TGG GAC GTC CGC GAC CAC GAT GAG CGA         1018
Val Arg Leu Gly Glu Trp Asp Val Arg Asp His Asp Glu Arg
215                 220                 225

CTG AAC CAC GAG GAA TAC GCA ATC GAA CGC AAA GAA GTT CAT         1060
Leu Asn His Glu Glu Tyr Ala Ile Glu Arg Lys Glu Val His
     230                 235                 240

CCT TCA TAT TCA CCA ACC GAT TTC CGG AAT GAT GTA GCC TTA         1102
Pro Ser Tyr Ser Pro Thr Asp Phe Arg Asn Asp Val Ala Leu
             245                 250                 255

GTG AAA CTC GAT AGA ACT GTT ATT TTC AAA CAA CAT ATT TTA         1144
Val Lys Leu Asp Arg Thr Val Ile Phe Lys Gln His Ile Leu
                 260                 265                 270

CCT GTC TGC TTA CCT CAT AAG CAA ATG AAA CTG GCT GGA AAA         1186
Pro Val Cys Leu Pro His Lys Gln Met Lys Leu Ala Gly Lys
                     275                 280

ATG GCA ACA GTC GCC GGA TGG GGA CGG ACG AGG CAC GGG CAG         1228
Met Ala Thr Val Ala Gly Trp Gly Arg Thr Arg His Gly Gln
285                 290                 295

AGC ACT GTG CCG GCT GTC TTA CAA GAA GTC GAT GTC GAG GTG         1270
Ser Thr Val Pro Ala Val Leu Gln Glu Val Asp Val Glu Val
     300                 305                 310
```

-continued

| | | |
|---|---|---|
| ATT CCG AAT GAA AGA TGC CAG AGG TGG TTC CGT GCT GCG GGT<br>Ile Pro Asn Glu Arg Cys Gln Arg Trp Phe Arg Ala Ala Gly<br>           315                  320                  325 | | 1312 |
| CGA CGA GAA ACC ATT CAC GAT GTC TTT CTC TGC GCC GGA TAT<br>Arg Arg Glu Thr Ile His Asp Val Phe Leu Cys Ala Gly Tyr<br>              330                  335                  340 | | 1354 |
| AAA GAG GGT GGT CGT GAT TCA TGC CAA GGT GAT TCT GGA GGT<br>Lys Glu Gly Gly Arg Asp Ser Cys Gln Gly Asp Ser Gly Gly<br>                  345                  350 | | 1396 |
| CCT CTA ATA ATG CAG ATT GAG GGT AGA AGG ACC CTT GTG GGT<br>Pro Leu Ile Met Gln Ile Glu Gly Arg Arg Thr Leu Val Gly<br>355                360                        365 | | 1438 |
| CTA GTT TCT TGG GGC ATT GGA TGT GGT CGT GAG CAT TTA CCA<br>Leu Val Ser Trp Gly Ile Gly Cys Gly Arg Glu His Leu Pro<br>    370                  375                  380 | | 1480 |
| GGC GTA TAT ACC AAT ATA CAA AAA TTC ATA CCG TGG ATC GAC<br>Gly Val Tyr Thr Asn Ile Gln Lys Phe Ile Pro Trp Ile Asp<br>            385                  390                  395 | | 1522 |
| AAA GTA ATG GGA TAA TTTTTATTCC ATCGAGCTTA CCCAAAGTAT<br>Lys Val Met Gly<br>            400 | | 1567 |
| TTATTAAGTG TTAATCGAAA GTTCCAATAA TAAATTAATT TAAAATTCTA | | 1617 |
| AAGACGGGAA TTTGAAAGAC CAAAAAGACA TACTTGTGAT TGTGTAATTT | | 1667 |
| TTATGATTAA CTTTACATCA TCTGTGCTTA ATTATTAATT TGTATTATTC | | 1717 |
| TTGCAAATAT TTCAAGAGTT ACCGAAAAGT TTGCTAATCG ATAATGATAT | | 1767 |
| TTTAAGAAAA ACAACTGCTG CTGATTCAGT CAATGTTAGA ATAATTATGT | | 1817 |
| TTACTAAATA ATATTAAGTT CTGATTAGTA AATAAATAGC AAAATTATCT | | 1867 |
| AAATATATAT AAAAAAAAAA AAAAAAA | | 1894 |

(2) INFORMATION FOR SEQ ID NO:4:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:4:

CAAAGGATCC CATGCCAACC CTCGTGGAGT TGATGTGTC                            39

(2) INFORMATION FOR SEQ ID NO:5:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:5:

ATTCCTCGTG GTTCAGTCGC TC                                                  22

(2) INFORMATION FOR SEQ ID NO:6:

(i) SEQUENCE CHARACTERISTICS:
        (A) LENGTH: 1373 nucleotides
        (B) TYPE: nucleic acid

```
            (C) STRANDEDNESS: single
            (D) TOPOLOGY: linear (ii) MOLECULE TYPE: cDNA (ix) FEATURE:
            (A) NAME/KEY: CDS
            (B) LOCATION: 199..1359

(xi) SEQUENCE DESCRIPTION: SEQ ID NO:6:

TCAGTTTTTT TGTCTAATCA GGATATTTAA ATTTATGTGT ACAAGTGTTA          50

AACGCGATCT CGTCGCTTTT CCTAATTTTC TTGTTGCCAA TGCTGGCCTC         100

AGTGCATCGG CCGACGCAAA TGTGCTTGCA AAATAGAGAA ATCCGGTGAA         150

ATCACACATG TTAGCGATCG TCCCGGTCAA ACGGAGCGTT CGCAGACC           198

ATG CCA ACC CTC GTG GAG TTG ATG TGT CTT TCT GGT TTG ATT        240
Met Pro Thr Leu Val Glu Leu Met Cys Leu Ser Gly Leu Ile
1               5                   10

CTG GTC GCT GTT GCG ATA TCT TCG ATT GGA TAT GCG GAC GCG        282
Leu Val Ala Val Ala Ile Ser Ser Ile Gly Tyr Ala Asp Ala
15                  20                  25

GCG AAC GTT GCG CAG GAC GGA CAT CCG TCC AGC CAG CAA GAG        324
Ala Asn Val Ala Gln Asp Gly His Pro Ser Ser Gln Gln Glu
    30                  35                  40

CAG GAG ATC CTG CTG CTG AAC GCC CTA GCT CGC AGG AAC GGA        366
Gln Glu Ile Leu Leu Leu Asn Ala Leu Ala Arg Arg Asn Gly
            45                  50                  55

GCG ACG GGG TAC CAA TTT GAC GTA GAT CAA GAT TCA ATT ATG        408
Ala Thr Gly Tyr Gln Phe Asp Val Asp Gln Asp Ser Ile Met
                60                  65                  70

GAT ATG CTA GGA AGA ATG ATA CCT CAG ACT TGT CGG TAC AAA        450
Asp Met Leu Gly Arg Met Ile Pro Gln Thr Cys Arg Tyr Lys
                    75                  80

GGC GAA CGG TTC GAA TGC GGT TTG TCA ATT TCT TGT GTC CTG        492
Gly Glu Arg Phe Glu Cys Gly Leu Ser Ile Ser Cys Val Leu
85                  90                  95

GGC GGC GGA AAG CCC CTT GAC CTG TGC AGC GGC GGA ATG ATC        534
Gly Gly Gly Lys Pro Leu Asp Leu Cys Ser Gly Gly Met Ile
    100                 105                 110

TGG TCG TGC TGC GTC GAC AGG GAC ATT CGG CCT GAG CCG CAG        576
Trp Ser Cys Cys Val Asp Arg Asp Ile Arg Pro Glu Pro Gln
            115                 120                 125

CAC CAG GGC GCT CTG CAG AAC GCA ACT TGT GGA GAA TTG TAC        618
His Gln Gly Ala Leu Gln Asn Ala Thr Cys Gly Glu Leu Tyr
                130                 135                 140

ACG AGG TCT AAT AGA ATC GTA GGA GGT CAT TCA ACA GGA TTC        660
Thr Arg Ser Asn Arg Ile Val Gly Gly His Ser Thr Gly Phe
                    145                 150

GGG TCT CAT CCT TGG CAG GCG GCT TTG ATC AAA TCA GGA TTT        702
Gly Ser His Pro Trp Gln Ala Ala Leu Ile Lys Ser Gly Phe
155                 160                 165

TTG AGT AAA AAA TTA TCT TGC GGT GGT GCC TTA GTT AGC GAT        744
Leu Ser Lys Lys Leu Ser Cys Gly Gly Ala Leu Val Ser Asp
    170                 175                 180

CGA TGG GTT ATA ACT GCT GCA CAT TGC GTT GCC ACG ACA CCA        786
Arg Trp Val Ile Thr Ala Ala His Cys Val Ala Thr Thr Pro
            185                 190                 195

AAT TCG AAC CTG AAG GTG CGT TTG GGC GAA TGG GAC GTT CGC        828
Asn Ser Asn Leu Lys Val Arg Leu Gly Glu Trp Asp Val Arg
                200                 205                 210
```

| | | |
|---|---|---|
| GAC CAC GAT GAG CGA CTG AAC CAC GAG GAA TAC GCA ATC GAA | | 870 |
| Asp His Asp Glu Arg Leu Asn His Glu Glu Tyr Ala Ile Glu | | |
| 215 220 | | |
| CGC AAA GAA GTT CAT CCT TCA TAT TCA CCA ACC GAT TTC CGG | | 912 |
| Arg Lys Glu Val His Pro Ser Tyr Ser Pro Thr Asp Phe Arg | | |
| 225 230 235 | | |
| AAT GAT GTA GCC TTA GTG AAA CTC GAT AGA ACT GTT ATT TTC | | 954 |
| Asn Asp Val Ala Leu Val Lys Leu Asp Arg Thr Val Ile Phe | | |
| 240 245 250 | | |
| AAA CAA CAT ATT TTA CCT GTC TGC TTA CCT CAT AAG CAA ATG | | 996 |
| Lys Gln His Ile Leu Pro Val Cys Leu Pro His Lys Gln Met | | |
| 255 260 265 | | |
| AAA CTG GCT GGA AAA ATG GCA ACA GTC GCC GGA TGG GGA CGG | | 1038 |
| Lys Leu Ala Gly Lys Met Ala Thr Val Ala Gly Trp Gly Arg | | |
| 270 275 280 | | |
| ACG AGG CAC GGG CAG AGC ACT GTG CCG GCT GTC TTA CAA GAA | | 1080 |
| Thr Arg His Gly Gln Ser Thr Val Pro Ala Val Leu Gln Glu | | |
| 285 290 | | |
| GTC GAT GTC GAG GTG ATT CCG AAT GAA AGA TGC CAG AGG TGG | | 1122 |
| Val Asp Val Glu Val Ile Pro Asn Glu Arg Cys Gln Arg Trp | | |
| 295 300 305 | | |
| TTC CGT GCT GCG GGT CGA CGA GAA ACC ATT CAC GAT GTC TTT | | 1164 |
| Phe Arg Ala Ala Gly Arg Arg Glu Thr Ile His Asp Val Phe | | |
| 310 315 320 | | |
| CTC TGC GCC GGA TAT AAA GAG GGT GGT CGT GAT TCA TGC CAA | | 1206 |
| Leu Cys Ala Gly Tyr Lys Glu Gly Gly Arg Asp Ser Cys Gln | | |
| 325 330 335 | | |
| GGT GAT TCT GGA GGT CCT CTA ACA ATG CAG ATT GAG GGT AGA | | 1248 |
| Gly Asp Ser Gly Gly Pro Leu Thr Met Gln Ile Glu Gly Arg | | |
| 340 345 350 | | |
| AGG ACC CTT GTG GGT CTA GTT TCT TGG GGC ATC GGA TGT GGT | | 1290 |
| Arg Thr Leu Val Gly Leu Val Ser Trp Gly Ile Gly Cys Gly | | |
| 355 360 | | |
| CGT GAG CAT TTA CCA GGC GTA TAT ACC AAT ATA CAA AAA TTC | | 1332 |
| Arg Glu His Leu Pro Gly Val Tyr Thr Asn Ile Gln Lys Phe | | |
| 365 370 375 | | |
| ATA CCG TGG ATC GAC AAA GTA ATG GGA TAA GAATCGAAGT C | | 1373 |
| Ile Pro Trp Ile Asp Lys Val Met Gly | | |
| 380 385 | | |

(2) INFORMATION FOR SEQ ID NO:7:

(i) SEQUENCE CHARACTERISTICS:
        (A) LENGTH: 1373 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

| | |
|---|---|
| GACTTCGATT CTTATCCCAT TACTTTGTCG ATCCACGGTA TGAATTTTTG | 50 |
| TATATTGGTA TATACGCCTG GTAAATGCTC ACGACCACAT CCGATGCCCC | 100 |
| AAGAAACTAG ACCCACAAGG GTCCTTCTAC CCTCAATCTG CATTGTTAGA | 150 |
| GGACCTCCAG AATCACCTTG GCATGAATCA CGACCACCCT CTTTATATCC | 200 |
| GGCGCAGAGA AAGACATCGT GAATGGTTTC TCGTCGACCC GCAGCACGGA | 250 |
| ACCACCTCTG GCATCTTTCA TTCGGAATCA CCTCGACATC GACTTCTTGT | 300 |
| AAGACAGCCG GCACAGTGCT CTGCCCGTGC CTCGTCCGTC CCCATCCGGC | 350 |

-continued

```
GACTGTTGCC ATTTTTCCAG CCAGTTTCAT TTGCTTATGA GGTAAGCAGA        400

CAGGTAAAAT ATGTTGTTTG AAAATAACAG TTCTATCGAG TTTCACTAAG        450

GCTACATCAT TCCGGAAATC GGTTGGTGAA TATGAAGGAT GAACTTCTTT        500

GCGTTCGATT GCGTATTCCT CGTGGTTCAG TCGCTCATCG TGGTCGCGAA        550

CGTCCCATTC GCCCAAACGC ACCTTCAGGT TCGAATTTGG TGTCGTGGCA        600

ACGCAATGTG CAGCAGTTAT AACCCATCGA TCGCTAACTA AGGCACCACC        650

GCAAGATAAT TTTTTACTCA AAAATCCTGA TTTGATCAAA GCCGCCTGCC        700

AAGGATGAGA CCCGAATCCT GTTGAATGAC CTCCTACGAT TCTATTAGAC        750

CTCGTGTACA ATTCTCCACA AGTTGCGTTC TGCAGAGCGC CCTGGTGCTG        800

CGGCTCAGGC CGAATGTCCC TGTCGACGCA GCACGACCAG ATCATTCCGC        850

CGCTGCACAG GTCAAGGGGC TTTCCGCCGC CCAGGACACA AGAAATTGAC        900

AAACCGCATT CGAACCGTTC GCCTTTGTAC CGACAAGTCT GAGGTATCAT        950

TCTTCCTAGC ATATCCATAA TTGAATCTTG ATCTACGTCA AATTGGTACC       1000

CCGTCGCTCC GTTCCTGCGA GCTAGGGCGT TCAGCAGCAG GATCTCCTGC       1050

TCTTGCTGGC TGGACGGATG TCCGTCCTGC GCAACGTTCG CCGCGTCCGC       1100

ATATCCAATC GAAGATATCG CAACAGCGAC CAGAATCAAA CCAGAAAGAC       1150

ACATCAACTC CACGAGGGTT GGCATGGTCT GCGAACGCTC CGTTTGACCG       1200

GGACGATCGC TAACATGTGT GATTTCACCG GATTTCTCTA TTTTGCAAGC       1250

ACATTTGCGT CGGCCGATGC ACTGAGGCCA GCATTGGCAA CAAGAAAATT       1300

AGGAAAAGCG ACGAGATCGC GTTTAACACT TGTACACATA AATTTAAATA       1350

TCCTGATTAG ACAAAAAAAC TGA                                    1373
```

(2) INFORMATION FOR SEQ ID NO:8:

(i) SEQUENCE CHARACTERISTICS:
        (A) LENGTH: 387 amino acids
        (B) TYPE: amino acid
        (D) TOPOLOGY: linear (ii) MOLECULE TYPE: Protein (xi) SEQUENCE DESCRIPTION: SEQ ID NO:8:

```
Met Pro Thr Leu Val Glu Leu Met Cys Leu Ser Gly Leu Ile
 1               5                  10

Leu Val Ala Val Ala Ile Ser Ser Ile Gly Tyr Ala Asp Ala
        15                  20                  25

Ala Asn Val Ala Gln Asp Gly His Pro Ser Ser Gln Gln Glu
             30                  35                  40

Gln Glu Ile Leu Leu Asn Ala Leu Ala Arg Arg Asn Gly
                45                  50                  55

Ala Thr Gly Tyr Gln Phe Asp Val Asp Gln Asp Ser Ile Met
                     60                  65              70

Asp Met Leu Gly Arg Met Ile Pro Gln Thr Cys Arg Tyr Lys
                75                  80

Gly Glu Arg Phe Glu Cys Gly Leu Ser Ile Ser Cys Val Leu
85                  90                  95

Gly Gly Gly Lys Pro Leu Asp Leu Cys Ser Gly Gly Met Ile
        100                 105                 110
```

```
Trp Ser Cys Cys Val Asp Arg Asp Ile Arg Pro Glu Pro Gln
        115                 120                 125

His Gln Gly Ala Leu Gln Asn Ala Thr Cys Gly Glu Leu Tyr
            130                 135                 140

Thr Arg Ser Asn Arg Ile Val Gly Gly His Ser Thr Gly Phe
                145                 150

Gly Ser His Pro Trp Gln Ala Ala Leu Ile Lys Ser Gly Phe
155                 160                 165

Leu Ser Lys Lys Leu Ser Cys Gly Gly Ala Leu Val Ser Asp
    170                 175                 180

Arg Trp Val Ile Thr Ala Ala His Cys Val Ala Thr Thr Pro
            185                 190                 195

Asn Ser Asn Leu Lys Val Arg Leu Gly Glu Trp Asp Val Arg
                200                 205                 210

Asp His Asp Glu Arg Leu Asn His Glu Glu Tyr Ala Ile Glu
                    215                 220

Arg Lys Glu Val His Pro Ser Tyr Ser Pro Thr Asp Phe Arg
225                 230                 235

Asn Asp Val Ala Leu Val Lys Leu Asp Arg Thr Val Ile Phe
    240                 245                 250

Lys Gln His Ile Leu Pro Val Cys Leu Pro His Lys Gln Met
        255                 260                 265

Lys Leu Ala Gly Lys Met Ala Thr Val Ala Gly Trp Gly Arg
            270                 275                 280

Thr Arg His Gly Gln Ser Thr Val Pro Ala Val Leu Gln Glu
                285                 290

Val Asp Val Glu Val Ile Pro Asn Glu Arg Cys Gln Arg Trp
295                 300                 305

Phe Arg Ala Ala Gly Arg Arg Glu Thr Ile His Asp Val Phe
    310                 315                 320

Leu Cys Ala Gly Tyr Lys Glu Gly Gly Arg Asp Ser Cys Gln
        325                 330                 335

Gly Asp Ser Gly Gly Pro Leu Thr Met Gln Ile Glu Gly Arg
            340                 345                 350

Arg Thr Leu Val Gly Leu Val Ser Trp Gly Ile Gly Cys Gly
                355                 360

Arg Glu His Leu Pro Gly Val Tyr Thr Asn Ile Gln Lys Phe
365                 370                 375

Ile Pro Trp Ile Asp Lys Val Met Gly
    380                 385

(2) INFORMATION FOR SEQ ID NO:9:

(i) SEQUENCE CHARACTERISTICS:
        (A) LENGTH: 1161 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1161

(xi) SEQUENCE DESCRIPTION: SEQ ID NO:9:
```

| | | | | | | | | | | | |
|---|---|---|---|---|---|---|---|---|---|---|---|
| ATG | CCA | ACC | CTC | GTG | GAG | TTG | ATG | TGT | CTT | TCT GGT TTG ATT | 42 |
| Met | Pro | Thr | Leu | Val | Glu | Leu | Met | Cys | Leu | Ser Gly Leu Ile | |
| 1 | | | 5 | | | | | 10 | | | |
| CTG | GTC | GCT | GTT | GCG | ATA | TCT | TCG | ATT | GGA | TAT GCG GAC GCG | 84 |
| Leu | Val | Ala | Val | Ala | Ile | Ser | Ser | Ile | Gly | Tyr Ala Asp Ala | |
| 15 | | | | 20 | | | | | 25 | | |
| GCG | AAC | GTT | GCG | CAG | GAC | GGA | CAT | CCG | TCC | AGC CAG CAA GAG | 126 |
| Ala | Asn | Val | Ala | Gln | Asp | Gly | His | Pro | Ser | Ser Gln Gln Glu | |
| | 30 | | | | 35 | | | | 40 | | |
| CAG | GAG | ATC | CTG | CTG | CTG | AAC | GCC | CTA | GCT | CGC AGG AAC GGA | 168 |
| Gln | Glu | Ile | Leu | Leu | Leu | Asn | Ala | Leu | Ala | Arg Arg Asn Gly | |
| | | 45 | | | | 50 | | | | 55 | |
| GCG | ACG | GGG | TAC | CAA | TTT | GAC | GTA | GAT | CAA | GAT TCA ATT ATG | 210 |
| Ala | Thr | Gly | Tyr | Gln | Phe | Asp | Val | Asp | Gln | Asp Ser Ile Met | |
| | | | 60 | | | | 65 | | | | 70 |
| GAT | ATG | CTA | GGA | AGA | ATG | ATA | CCT | CAG | ACT | TGT CGG TAC AAA | 252 |
| Asp | Met | Leu | Gly | Arg | Met | Ile | Pro | Gln | Thr | Cys Arg Tyr Lys | |
| | | | | 75 | | | | 80 | | | |
| GGC | GAA | CGG | TTC | GAA | TGC | GGT | TTG | TCA | ATT | TCT TGT GTC CTG | 294 |
| Gly | Glu | Arg | Phe | Glu | Cys | Gly | Leu | Ser | Ile | Ser Cys Val Leu | |
| 85 | | | | 90 | | | | 95 | | | |
| GGC | GGC | GGA | AAG | CCC | CTT | GAC | CTG | TGC | AGC | GGC GGA ATG ATC | 336 |
| Gly | Gly | Gly | Lys | Pro | Leu | Asp | Leu | Cys | Ser | Gly Gly Met Ile | |
| | 100 | | | | 105 | | | | 110 | | |
| TGG | TCG | TGC | TGC | GTC | GAC | AGG | GAC | ATT | CGG | CCT GAG CCG CAG | 378 |
| Trp | Ser | Cys | Cys | Val | Asp | Arg | Asp | Ile | Arg | Pro Glu Pro Gln | |
| | | 115 | | | | 120 | | | | 125 | |
| CAC | CAG | GGC | GCT | CTG | CAG | AAC | GCA | ACT | TGT | GGA GAA TTG TAC | 420 |
| His | Gln | Gly | Ala | Leu | Gln | Asn | Ala | Thr | Cys | Gly Glu Leu Tyr | |
| | | | 130 | | | | 135 | | | | 140 |
| ACG | AGG | TCT | AAT | AGA | ATC | GTA | GGA | GGT | CAT | TCA ACA GGA TTC | 462 |
| Thr | Arg | Ser | Asn | Arg | Ile | Val | Gly | Gly | His | Ser Thr Gly Phe | |
| | | | | 145 | | | | 150 | | | |
| GGG | TCT | CAT | CCT | TGG | CAG | GCG | GCT | TTG | ATC | AAA TCA GGA TTT | 504 |
| Gly | Ser | His | Pro | Trp | Gln | Ala | Ala | Leu | Ile | Lys Ser Gly Phe | |
| 155 | | | | 160 | | | | 165 | | | |
| TTG | AGT | AAA | AAA | TTA | TCT | TGC | GGT | GGT | GCC | TTA GTT AGC GAT | 546 |
| Leu | Ser | Lys | Lys | Leu | Ser | Cys | Gly | Gly | Ala | Leu Val Ser Asp | |
| | 170 | | | | 175 | | | | 180 | | |
| CGA | TGG | GTT | ATA | ACT | GCT | GCA | CAT | TGC | GTT | GCC ACG ACA CCA | 588 |
| Arg | Trp | Val | Ile | Thr | Ala | Ala | His | Cys | Val | Ala Thr Thr Pro | |
| | | 185 | | | | 190 | | | | 195 | |
| AAT | TCG | AAC | CTG | AAG | GTG | CGT | TTG | GGC | GAA | TGG GAC GTT CGC | 630 |
| Asn | Ser | Asn | Leu | Lys | Val | Arg | Leu | Gly | Glu | Trp Asp Val Arg | |
| | | | 200 | | | | 205 | | | | 210 |
| GAC | CAC | GAT | GAG | CGA | CTG | AAC | CAC | GAG | GAA | TAC GCA ATC GAA | 672 |
| Asp | His | Asp | Glu | Arg | Leu | Asn | His | Glu | Glu | Tyr Ala Ile Glu | |
| | | | | 215 | | | | 220 | | | |
| CGC | AAA | GAA | GTT | CAT | CCT | TCA | TAT | TCA | CCA | ACC GAT TTC CGG | 714 |
| Arg | Lys | Glu | Val | His | Pro | Ser | Tyr | Ser | Pro | Thr Asp Phe Arg | |
| 225 | | | | 230 | | | | 235 | | | |
| AAT | GAT | GTA | GCC | TTA | GTG | AAA | CTC | GAT | AGA | ACT GTT ATT TTC | 756 |
| Asn | Asp | Val | Ala | Leu | Val | Lys | Leu | Asp | Arg | Thr Val Ile Phe | |
| | 240 | | | | 245 | | | | 250 | | |
| AAA | CAA | CAT | ATT | TTA | CCT | GTC | TGC | TTA | CCT | CAT AAG CAA ATG | 798 |
| Lys | Gln | His | Ile | Leu | Pro | Val | Cys | Leu | Pro | His Lys Gln Met | |
| | | 255 | | | | 260 | | | | 265 | |
| AAA | CTG | GCT | GGA | AAA | ATG | GCA | ACA | GTC | GCC | GGA TGG GGA CGG | 840 |
| Lys | Leu | Ala | Gly | Lys | Met | Ala | Thr | Val | Ala | Gly Trp Gly Arg | |
| | | | 270 | | | | 275 | | | | 280 |

```
ACG AGG CAC GGG CAG AGC ACT GTG CCG GCT GTC TTA CAA GAA       882
Thr Arg His Gly Gln Ser Thr Val Pro Ala Val Leu Gln Glu
            285                 290

GTC GAT GTC GAG GTG ATT CCG AAT GAA AGA TGC CAG AGG TGG       924
Val Asp Val Glu Val Ile Pro Asn Glu Arg Cys Gln Arg Trp
295                 300                 305

TTC CGT GCT GCG GGT CGA CGA GAA ACC ATT CAC GAT GTC TTT       966
Phe Arg Ala Ala Gly Arg Arg Glu Thr Ile His Asp Val Phe
    310                 315                 320

CTC TGC GCC GGA TAT AAA GAG GGT GGT CGT GAT TCA TGC CAA      1008
Leu Cys Ala Gly Tyr Lys Glu Gly Gly Arg Asp Ser Cys Gln
        325                 330                 335

GGT GAT TCT GGA GGT CCT CTA ACA ATG CAG ATT GAG GGT AGA      1050
Gly Asp Ser Gly Gly Pro Leu Thr Met Gln Ile Glu Gly Arg
            340                 345                 350

AGG ACC CTT GTG GGT CTA GTT TCT TGG GGC ATC GGA TGT GGT      1092
Arg Thr Leu Val Gly Leu Val Ser Trp Gly Ile Gly Cys Gly
                355                 360

CGT GAG CAT TTA CCA GGC GTA TAT ACC AAT ATA CAA AAA TTC      1134
Arg Glu His Leu Pro Gly Val Tyr Thr Asn Ile Gln Lys Phe
365                 370                 375

ATA CCG TGG ATC GAC AAA GTA ATG GGA                          1161
Ile Pro Trp Ile Asp Lys Val Met Gly
    380                 385

(2) INFORMATION FOR SEQ ID NO:10:

(i) SEQUENCE CHARACTERISTICS:
        (A) LENGTH:  1161 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:10:

TCCCATTACT TTGTCGATCC ACGGTATGAA TTTTTGTATA TTGGTATATA         50

CGCCTGGTAA ATGCTCACGA CCACATCCGA TGCCCCAAGA AACTAGACCC        100

ACAAGGGTCC TTCTACCCTC AATCTGCATT GTTAGAGGAC CTCCAGAATC        150

ACCTTGGCAT GAATCACGAC CACCCTCTTT ATATCCGGCG CAGAGAAAGA        200

CATCGTGAAT GGTTTCTCGT CGACCCGCAG CACGGAACCA CCTCTGGCAT        250

CTTTCATTCG GAATCACCTC GACATCGACT TCTTGTAAGA CAGCCGGCAC        300

AGTGCTCTGC CCGTGCCTCG TCCGTCCCCA TCCGGCGACT GTTGCCATTT        350

TTCCAGCCAG TTTCATTTGC TTATGAGGTA AGCAGACAGG TAAAATATGT        400

TGTTTGAAAA TAACAGTTCT ATCGAGTTTC ACTAAGGCTA CATCATTCCG        450

GAAATCGGTT GGTGAATATG AAGGATGAAC TTCTTTGCGT TCGATTGCGT        500

ATTCCTCGTG GTTCAGTCGC TCATCGTGGT CGCGAACGTC CCATTCGCCC        550

AAACGCACCT TCAGGTTCGA ATTTGGTGTC GTGGCAACGC AATGTGCAGC        600

AGTTATAACC CATCGATCGC TAACTAAGGC ACCACCGCAA GATAATTTTT        650

TACTCAAAAA TCCTGATTTG ATCAAAGCCG CCTGCCAAGG ATGAGACCCG        700

AATCCTGTTG AATGACCTCC TACGATTCTA TTAGACCTCG TGTACAATTC        750

TCCACAAGTT GCGTTCTGCA GAGCGCCCTG GTGCTGCGGC TCAGGCCGAA        800

TGTCCCTGTC GACGCAGCAC GACCAGATCA TTCCGCCGCT GCACAGGTCA        850
```

```
AGGGGCTTTC CGCCGCCCAG GACACAAGAA ATTGACAAAC CGCATTCGAA              900

CCGTTCGCCT TTGTACCGAC AAGTCTGAGG TATCATTCTT CCTAGCATAT              950

CCATAATTGA ATCTTGATCT ACGTCAAATT GGTACCCCGT CGCTCCGTTC             1000

CTGCGAGCTA GGGCGTTCAG CAGCAGGATC TCCTGCTCTT GCTGGCTGGA             1050

CGGATGTCCG TCCTGCGCAA CGTTCGCCGC GTCCGCATAT CCAATCGAAG             1100

ATATCGCAAC AGCGACCAGA ATCAAACCAG AAAGACACAT CAACTCCACG             1150

AGGGTTGGCA T                                                      1161

(2) INFORMATION FOR SEQ ID NO:11:

(i) SEQUENCE CHARACTERISTICS:
        (A) LENGTH:  32 nucleotides
        (B) TYPE:  nucleic acid
        (C) STRANDEDNESS:  single
        (D) TOPOLOGY:  linear (ii) MOLECULE TYPE:  Primer (xi) SEQUENCE DESCRIPTION:  SEQ ID NO:11:

CCGGAATTCT TATCCCATTA CTTTGTCGAT CC                                 32

(2) INFORMATION FOR SEQ ID NO:12:

(i) SEQUENCE CHARACTERISTICS:
        (A) LENGTH:  1175 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  1..1161

(xi) SEQUENCE DESCRIPTION:  SEQ ID NO:12:

ATG CCA ACC CTC GTG GAG TTG ATG TGT CTT TCT GGT TTG ATT              42
Met Pro Thr Leu Val Glu Leu Met Cys Leu Ser Gly Leu Ile
 1               5                  10

CTG GTC GCT GTT GCG ATA TCT TCG ATT GGA TAT GCG GAC GCG              84
Leu Val Ala Val Ala Ile Ser Ser Ile Gly Tyr Ala Asp Ala
 15                  20                  25

GCG AAC GTT GCG CAG GAC GGA CAT CCG TCC AGC CAG CAA GAG             126
Ala Asn Val Ala Gln Asp Gly His Pro Ser Ser Gln Gln Glu
     30                  35                  40

CAG GAG ATC CTG CTG CTG AAC GCC CTA GCT CGC AGG AAC GGA             168
Gln Glu Ile Leu Leu Leu Asn Ala Leu Ala Arg Arg Asn Gly
         45                  50                  55

GCG ACG GGG TAC CAA TTT GAC GTA GAT CAA GAT TCA ATT ATG             210
Ala Thr Gly Tyr Gln Phe Asp Val Asp Gln Asp Ser Ile Met
                 60                  65                  70

GAT ATG CTA GGA AGA ATG ATA CCT CAG ACT TGT CGG TAC AAA             252
Asp Met Leu Gly Arg Met Ile Pro Gln Thr Cys Arg Tyr Lys
                     75                  80

GGC GAA CGG TTC GAA TGC GGT TTG TCA ATT TCT TGT GTC CTG             294
Gly Glu Arg Phe Glu Cys Gly Leu Ser Ile Ser Cys Val Leu
85                  90                  95

GGC GGC GGA AAG CCC CTT GAC CTG TGC AGC GGC GGA ATG ATC             336
Gly Gly Gly Lys Pro Leu Asp Leu Cys Ser Gly Gly Met Ile
        100                 105                 110
```

```
TGG TCG TGC TGC GTC GAC AGG GAC ATT CGG CCT GAG CCG CAG           378
Trp Ser Cys Cys Val Asp Arg Asp Ile Arg Pro Glu Pro Gln
    115                 120                 125

CAC CAG GGC GCT CTG CAG AAC GCA ACT TGT GGA GAA TTG TAC           420
His Gln Gly Ala Leu Gln Asn Ala Thr Cys Gly Glu Leu Tyr
        130                 135                 140

ACG AGG TCT AAT AGA ATC GTA GGA GGT CAT TCA ACA GGA TTC           462
Thr Arg Ser Asn Arg Ile Val Gly Gly His Ser Thr Gly Phe
            145                 150

GGG TCT CAT CCT TGG CAG GCG GCT TTG ATC AAA TCA GGA TTT           504
Gly Ser His Pro Trp Gln Ala Ala Leu Ile Lys Ser Gly Phe
155                 160                 165

TTG AGT AAA AAA TTA TCT TGC GGT GGT GCC TTA GTT AGC GAT           546
Leu Ser Lys Lys Leu Ser Cys Gly Gly Ala Leu Val Ser Asp
    170                 175                 180

CGA TGG GTT ATA ACT GCT GCA CAT TGC GTT GCC ACG ACA CCA           588
Arg Trp Val Ile Thr Ala Ala His Cys Val Ala Thr Thr Pro
        185                 190                 195

AAT TCG AAC CTG AAG GTG CGT TTG GGC GAA TGG GAC GTT CGC           630
Asn Ser Asn Leu Lys Val Arg Leu Gly Glu Trp Asp Val Arg
            200                 205                 210

GAC CAC GAT GAG CGA CTG AAC CAC GAG GAA TAC GCA ATC GAA           672
Asp His Asp Glu Arg Leu Asn His Glu Glu Tyr Ala Ile Glu
                215                 220

CGC AAA GAA GTT CAT CCT TCA TAT TCA CCA ACC GAT TTC CGG           714
Arg Lys Glu Val His Pro Ser Tyr Ser Pro Thr Asp Phe Arg
225                 230                 235

AAT GAT GTA GCC TTA GTG AAA CTC GAT AGA ACT GTT ATT TTC           756
Asn Asp Val Ala Leu Val Lys Leu Asp Arg Thr Val Ile Phe
    240                 245                 250

AAA CAA CAT ATT TTA CCT GTC TGC TTA CCT CAT AAG CAA ATG           798
Lys Gln His Ile Leu Pro Val Cys Leu Pro His Lys Gln Met
        255                 260                 265

AAA CTG GCT GGA AAA ATG GCA ACA GTC GCC GGA TGG GGA CGG           840
Lys Leu Ala Gly Lys Met Ala Thr Val Ala Gly Trp Gly Arg
            270                 275                 280

ACG AGG CAC GGG CAG AGC ACT GTG CCG GCT GTC TTA CAA GAA           882
Thr Arg His Gly Gln Ser Thr Val Pro Ala Val Leu Gln Glu
                285                 290

GTC GAT GTC GAG GTG ATT CCG AAT GAA AGA TGC CAG AGG TGG           924
Val Asp Val Glu Val Ile Pro Asn Glu Arg Cys Gln Arg Trp
295                 300                 305

TTC CGT GCT GCG GGT CGA CGA GAA ACC ATT CAC GAT GTC TTT           966
Phe Arg Ala Ala Gly Arg Arg Glu Thr Ile His Asp Val Phe
    310                 315                 320

CTC TGC GCC GGA TAT AAA GAG GGT GGT CGT GAT TCA TGC CAA          1008
Leu Cys Ala Gly Tyr Lys Glu Gly Gly Arg Asp Ser Cys Gln
        325                 330                 335

GGT GAT TCT GGA GGT CCT CTA ACA ATG CAG ATT GAG GGT AGA          1050
Gly Asp Ser Gly Gly Pro Leu Thr Met Gln Ile Glu Gly Arg
            340                 345                 350

AGG ACC CTT GTG GGT CTA GTT TCT TGG GGC ATC GGA TGT GGT          1092
Arg Thr Leu Val Gly Leu Val Ser Trp Gly Ile Gly Cys Gly
                355                 360

CGT GAG CAT TTA CCA GGC GTA TAT ACC AAT ATA CAA AAA TTC          1134
Arg Glu His Leu Pro Gly Val Tyr Thr Asn Ile Gln Lys Phe
365                 370                 375

ATA CCG TGG ATC GAC AAA GTA ATG GGA TAA GAATCGAAGT C             1175
Ile Pro Trp Ile Asp Lys Val Met Gly
    380                 385
```

(2) INFORMATION FOR SEQ ID NO:13:

(i) SEQUENCE CHARACTERISTICS:
        (A) LENGTH: 387 amino acids
        (B) TYPE: amino acid
        (D) TOPOLOGY: linear (ii) MOLECULE TYPE: Protein (xi) SEQUENCE DESCRIPTION: SEQ ID NO:13:

```
Met Pro Thr Leu Val Glu Leu Met Cys Leu Ser Gly Leu Ile
 1               5                  10

Leu Val Ala Val Ala Ile Ser Ser Ile Gly Tyr Ala Asp Ala
 15                  20                  25

Ala Asn Val Ala Gln Asp Gly His Pro Ser Ser Gln Gln Glu
         30                  35                  40

Gln Glu Ile Leu Leu Leu Asn Ala Leu Ala Arg Arg Asn Gly
                 45                  50                  55

Ala Thr Gly Tyr Gln Phe Asp Val Asp Gln Asp Ser Ile Met
                     60                  65                  70

Asp Met Leu Gly Arg Met Ile Pro Gln Thr Cys Arg Tyr Lys
                     75                  80

Gly Glu Arg Phe Glu Cys Gly Leu Ser Ile Ser Cys Val Leu
 85                  90                  95

Gly Gly Gly Lys Pro Leu Asp Leu Cys Ser Gly Gly Met Ile
 100                 105                 110

Trp Ser Cys Cys Val Asp Arg Asp Ile Arg Pro Glu Pro Gln
         115                 120                 125

His Gln Gly Ala Leu Gln Asn Ala Thr Cys Gly Glu Leu Tyr
             130                 135                 140

Thr Arg Ser Asn Arg Ile Val Gly Gly His Ser Thr Gly Phe
                 145                 150

Gly Ser His Pro Trp Gln Ala Ala Leu Ile Lys Ser Gly Phe
155                 160                 165

Leu Ser Lys Lys Leu Ser Cys Gly Gly Ala Leu Val Ser Asp
     170                 175                 180

Arg Trp Val Ile Thr Ala Ala His Cys Val Ala Thr Thr Pro
             185                 190                 195

Asn Ser Asn Leu Lys Val Arg Leu Gly Glu Trp Asp Val Arg
                 200                 205                 210

Asp His Asp Glu Arg Leu Asn His Glu Glu Tyr Ala Ile Glu
                     215                 220

Arg Lys Glu Val His Pro Ser Tyr Ser Pro Thr Asp Phe Arg
225                 230                 235

Asn Asp Val Ala Leu Val Lys Leu Asp Arg Thr Val Ile Phe
     240                 245                 250

Lys Gln His Ile Leu Pro Val Cys Leu Pro His Lys Gln Met
             255                 260                 265

Lys Leu Ala Gly Lys Met Ala Thr Val Ala Gly Trp Gly Arg
                 270                 275                 280

Thr Arg His Gly Gln Ser Thr Val Pro Ala Val Leu Gln Glu
                     285                 290

Val Asp Val Glu Val Ile Pro Asn Glu Arg Cys Gln Arg Trp
295                 300                 305
```

```
Phe Arg Ala Ala Gly Arg Arg Glu Thr Ile His Asp Val Phe
    310                 315                 320
Leu Cys Ala Gly Tyr Lys Glu Gly Gly Arg Asp Ser Cys Gln
        325                 330                 335
Gly Asp Ser Gly Gly Pro Leu Thr Met Gln Ile Glu Gly Arg
            340                 345                 350
Arg Thr Leu Val Gly Leu Val Ser Trp Gly Ile Gly Cys Gly
                355                 360
Arg Glu His Leu Pro Gly Val Tyr Thr Asn Ile Gln Lys Phe
365                 370                 375
Ile Pro Trp Ile Asp Lys Val Met Gly
    380                 385
```

(2) INFORMATION FOR SEQ ID NO:14:

(i) SEQUENCE CHARACTERISTICS:
        (A) LENGTH: 1175 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GACTTCGATT CTTATCCCAT TACTTTGTCG ATCCACGGTA TGAATTTTTG          50
TATATTGGTA TATACGCCTG GTAAATGCTC ACGACCACAT CCGATGCCCC         100
AAGAAACTAG ACCCACAAGG GTCCTTCTAC CCTCAATCTG CATTGTTAGA         150
GGACCTCCAG AATCACCTTG GCATGAATCA CGACCACCCT CTTTATATCC         200
GGCGCAGAGA AAGACATCGT GAATGGTTTC TCGTCGACCC GCAGCACGGA         250
ACCACCTCTG GCATCTTTCA TTCGGAATCA CCTCGACATC GACTTCTTGT         300
AAGACAGCCG GCACAGTGCT CTGCCCGTGC CTCGTCCGTC CCCATCCGGC         350
GACTGTTGCC ATTTTTCCAG CCAGTTTCAT TTGCTTATGA GGTAAGCAGA         400
CAGGTAAAAT ATGTTGTTTG AAAATAACAG TTCTATCGAG TTTCACTAAG         450
GCTACATCAT TCCGGAAATC GGTTGGTGAA TATGAAGGAT GAACTTCTTT         500
GCGTTCGATT GCGTATTCCT CGTGGTTCAG TCGCTCATCG TGGTCGCGAA         550
CGTCCCATTC GCCCAAACGC ACCTTCAGGT TCGAATTTGG TGTCGTGGCA         600
ACGCAATGTG CAGCAGTTAT AACCCATCGA TCGCTAACTA AGGCACCACC         650
GCAAGATAAT TTTTTACTCA AAAATCCTGA TTTGATCAAA GCCGCCTGCC         700
AAGGATGAGA CCCGAATCCT GTTGAATGAC CTCCTACGAT TCTATTAGAC         750
CTCGTGTACA ATTCTCCACA AGTTGCGTTC TGCAGAGCGC CCTGGTGCTG         800
CGGCTCAGGC CGAATGTCCC TGTCGACGCA GCACGACCAG ATCATTCCGC         850
CGCTGCACAG GTCAAGGGGC TTTCCGCCGC CCAGGACACA AGAAATTGAC         900
AAACCGCATT CGAACCGTTC GCCTTTGTAC CGACAAGTCT GAGGTATCAT         950
TCTTCCTAGC ATATCCATAA TTGAATCTTG ATCTACGTCA AATTGGTACC        1000
CCGTCGCTCC GTTCCTGCGA GCTAGGGCGT TCAGCAGCAG GATCTCCTGC        1050
TCTTGCTGGC TGGACGGATG TCCGTCCTGC GCAACGTTCG CCGCGTCCGC        1100
ATATCCAATC GAAGATATCG CAACAGCGAC CAGAATCAAA CCAGAAAGAC        1150
ACATCAACTC CACGAGGGTT GGCAT                                  1175
```

(2) INFORMATION FOR SEQ ID NO:15:

(i) SEQUENCE CHARACTERISTICS:
        (A) LENGTH: 1161 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
ATG CCA ACC CTC GTG GAG TTG ATG TGT CTT TCT GGT TTG ATT              42
Met Pro Thr Leu Val Glu Leu Met Cys Leu Ser Gly Leu Ile
 1               5                  10

CTG GTC GCT GTT GCG ATA TCT TCG ATT GGA TAT GCG GAC GCG              84
Leu Val Ala Val Ala Ile Ser Ser Ile Gly Tyr Ala Asp Ala
 15                  20                  25

GCG AAC GTT GCG CAG GAC GGA CAT CCG TCC AGC CAG CAA GAG             126
Ala Asn Val Ala Gln Asp Gly His Pro Ser Ser Gln Gln Glu
     30                  35                  40

CAG GAG ATC CTG CTG CTG AAC GCC CTA GCT CGC AGG AAC GGA             168
Gln Glu Ile Leu Leu Leu Asn Ala Leu Ala Arg Arg Asn Gly
             45                  50                  55

GCG ACG GGG TAC CAA TTT GAC GTA GAT CAA GAT TCA ATT ATG             210
Ala Thr Gly Tyr Gln Phe Asp Val Asp Gln Asp Ser Ile Met
                 60                  65                  70

GAT ATG CTA GGA AGA ATG ATA CCT CAG ACT TGT CGG TAC AAA             252
Asp Met Leu Gly Arg Met Ile Pro Gln Thr Cys Arg Tyr Lys
                     75                  80

GGC GAA CGG TTC GAA TGC GGT TTG TCA ATT TCT TGT GTC CTG             294
Gly Glu Arg Phe Glu Cys Gly Leu Ser Ile Ser Cys Val Leu
 85                  90                  95

GGC GGC GGA AAG CCC CTT GAC CTG TGC AGC GGC GGA ATG ATC             336
Gly Gly Gly Lys Pro Leu Asp Leu Cys Ser Gly Gly Met Ile
    100                 105                 110

TGG TCG TGC TGC GTC GAC AGG GAC ATT CGG CCT GAG CCG CAG             378
Trp Ser Cys Cys Val Asp Arg Asp Ile Arg Pro Glu Pro Gln
            115                 120                 125

CAC CAG GGC GCT CTG CAG AAC GCA ACT TGT GGA GAA TTG TAC             420
His Gln Gly Ala Leu Gln Asn Ala Thr Cys Gly Glu Leu Tyr
                130                 135                 140

ACG AGG TCT AAT AGA ATC GTA GGA GGT CAT TCA ACA GGA TTC             462
Thr Arg Ser Asn Arg Ile Val Gly Gly His Ser Thr Gly Phe
                    145                 150

GGG TCT CAT CCT TGG CAG GCG GCT TTG ATC AAA TCA GGA TTT             504
Gly Ser His Pro Trp Gln Ala Ala Leu Ile Lys Ser Gly Phe
155                 160                 165

TTG AGT AAA AAA TTA TCT TGC GGT GGT GCC TTA GTT AGC GAT             546
Leu Ser Lys Lys Leu Ser Cys Gly Gly Ala Leu Val Ser Asp
    170                 175                 180

CGA TGG GTT ATA ACT GCT GCA CAT TGC GTT GCC ACG ACA CCA             588
Arg Trp Val Ile Thr Ala Ala His Cys Val Ala Thr Thr Pro
            185                 190                 195

AAT TCG AAC CTG AAG GTG CGT TTG GGC GAA TGG GAC GTT CGC             630
Asn Ser Asn Leu Lys Val Arg Leu Gly Glu Trp Asp Val Arg
                200                 205                 210

GAC CAC GAT GAG CGA CTG AAC CAC GAG GAA TAC GCA ATC GAA             672
Asp His Asp Glu Arg Leu Asn His Glu Glu Tyr Ala Ile Glu
                    215                 220
```

-continued

```
CGC AAA GAA GTT CAT CCT TCA TAT TCA CCA ACC GAT TTC CGG         714
Arg Lys Glu Val His Pro Ser Tyr Ser Pro Thr Asp Phe Arg
225                 230                 235

AAT GAT GTA GCC TTA GTG AAA CTC GAT AGA ACT GTT ATT TTC         756
Asn Asp Val Ala Leu Val Lys Leu Asp Arg Thr Val Ile Phe
        240                 245                 250

AAA CAA CAT ATT TTA CCT GTC TGC TTA CCT CAT AAG CAA ATG         798
Lys Gln His Ile Leu Pro Val Cys Leu Pro His Lys Gln Met
            255                 260                 265

AAA CTG GCT GGA AAA ATG GCA ACA GTC GCC GGA TGG GGA CGG         840
Lys Leu Ala Gly Lys Met Ala Thr Val Ala Gly Trp Gly Arg
                270                 275                 280

ACG AGG CAC GGG CAG AGC ACT GTG CCG GCT GTC TTA CAA GAA         882
Thr Arg His Gly Gln Ser Thr Val Pro Ala Val Leu Gln Glu
                    285                 290

GTC GAT GTC GAG GTG ATT CCG AAT GAA AGA TGC CAG AGG TGG         924
Val Asp Val Glu Val Ile Pro Asn Glu Arg Cys Gln Arg Trp
295                 300                 305

TTC CGT GCT GCG GGT CGA CGA GAA ACC ATT CAC GAT GTC TTT         966
Phe Arg Ala Ala Gly Arg Arg Glu Thr Ile His Asp Val Phe
        310                 315                 320

CTC TGC GCC GGA TAT AAA GAG GGT GGT CGT GAT TCA TGC CAA        1008
Leu Cys Ala Gly Tyr Lys Glu Gly Gly Arg Asp Ser Cys Gln
            325                 330                 335

GGT GAT TCT GGA GGT CCT CTA ACA ATG CAG ATT GAG GGT AGA        1050
Gly Asp Ser Gly Gly Pro Leu Thr Met Gln Ile Glu Gly Arg
                340                 345                 350

AGG ACC CTT GTG GGT CTA GTT TCT TGG GGC ATC GGA TGT GGT        1092
Arg Thr Leu Val Gly Leu Val Ser Trp Gly Ile Gly Cys Gly
                    355                 360

CGT GAG CAT TTA CCA GGC GTA TAT ACC AAT ATA CAA AAA TTC        1134
Arg Glu His Leu Pro Gly Val Tyr Thr Asn Ile Gln Lys Phe
365                 370                 375

ATA CCG TGG ATC GAC AAA GTA ATG GGA                            1161
Ile Pro Trp Ile Asp Lys Val Met Gly
        380                 385
```

(2) INFORMATION FOR SEQ ID NO:16:

(i) SEQUENCE CHARACTERISTICS:
        (A) LENGTH: 1161 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
TCCCATTACT TGTCGATCC ACGGTATGAA TTTTTGTATA TTGGTATATA            50

CGCCTGGTAA ATGCTCACGA CCACATCCGA TGCCCCAAGA AACTAGACCC           100

ACAAGGGTCC TTCTACCCTC AATCTGCATT GTTAGAGGAC CTCCAGAATC           150

ACCTTGGCAT GAATCACGAC CACCCTCTTT ATATCCGGCG CAGAGAAAGA           200

CATCGTGAAT GGTTTCTCGT CGACCCGCAG CACGGAACCA CCTCTGGCAT           250

CTTTCATTCG GAATCACCTC GACATCGACT TCTTGTAAGA CAGCCGGCAC           300

AGTGCTCTGC CCGTGCCTCG TCCGTCCCCA TCCGGCGACT GTTGCCATTT           350

TTCCAGCCAG TTTCATTTGC TTATGAGGTA AGCAGACAGG TAAAATATGT           400

TGTTTGAAAA TAACAGTTCT ATCGAGTTTC ACTAAGGCTA CATCATTCCG           450
```

| | |
|---|---|
| GAAATCGGTT GGTGAATATG AAGGATGAAC TTCTTTGCGT TCGATTGCGT | 500 |
| ATTCCTCGTG GTTCAGTCGC TCATCGTGGT CGCGAACGTC CCATTCGCCC | 550 |
| AAACGCACCT TCAGGTTCGA ATTTGGTGTC GTGGCAACGC AATGTGCAGC | 600 |
| AGTTATAACC CATCGATCGC TAACTAAGGC ACCACCGCAA GATAATTTTT | 650 |
| TACTCAAAAA TCCTGATTTG ATCAAAGCCG CCTGCCAAGG ATGAGACCCG | 700 |
| AATCCTGTTG AATGACCTCC TACGATTCTA TTAGACCTCG TGTACAATTC | 750 |
| TCCACAAGTT GCGTTCTGCA GAGCGCCCTG GTGCTGCGGC TCAGGCCGAA | 800 |
| TGTCCCTGTC GACGCAGCAC GACCAGATCA TTCCGCCGCT GCACAGGTCA | 850 |
| AGGGGCTTTC CGCCGCCCAG GACACAAGAA ATTGACAAAC CGCATTCGAA | 900 |
| CCGTTCGCCT TTGTACCGAC AAGTCTGAGG TATCATTCTT CCTAGCATAT | 950 |
| CCATAATTGA ATCTTGATCT ACGTCAAATT GGTACCCCGT CGCTCCGTTC | 1000 |
| CTGCGAGCTA GGGCGTTCAG CAGCAGGATC TCCTGCTCTT GCTGGCTGGA | 1050 |
| CGGATGTCCG TCCTGCGCAA CGTTCGCCGC GTCCGCATAT CCAATCGAAG | 1100 |
| ATATCGCAAC AGCGACCAGA ATCAAACCAG AAAGACACAT CAACTCCACG | 1150 |
| AGGGTTGGCA T | 1161 |

(2) INFORMATION FOR SEQ ID NO:17:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (ii) MOLECULE TYPE: Primer (ix) FEATURE:
        (A) NAME/KEY: W = A or T/U
        (B) LOCATION: 4, 7, 10

(ix) FEATURE:
        (A) NAME/KEY: Y = C or T/U
        (B) LOCATION: 13

(xi) SEQUENCE DESCRIPTION: SEQ ID NO:17:

| | |
|---|---|
| TAAWGGWCCW CCYGAATCTC CCTGGCA | 27 |

(2) INFORMATION FOR SEQ ID NO:18:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: Primer (ix) FEATURE:
        (A) NAME/KEY: W = A or T/U
        (B) LOCATION: 4, 7

(ix) FEATURE:
        (A) NAME/KEY: R = A or G
        (B) LOCATION: 13

(xi) SEQUENCE DESCRIPTION: SEQ ID NO:18:

| | |
|---|---|
| TAAWGGWCCA GARTCTCCTT GACA | 24 |

(2) INFORMATION FOR SEQ ID NO:19:

(i) SEQUENCE CHARACTERISTICS:
        (A) LENGTH: 436 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..436

(ix) FEATURE:
        (A) NAME/KEY: W = A
        (B) LOCATION: 301

(ix) FEATURE:
        (A) NAME/KEY: Y = C
        (B) LOCATION: 342, 397

(ix) FEATURE:
        (A) NAME/KEY: S = C
        (B) LOCATION: 431

(ix) FEATURE:
        (A) NAME/KEY: Xaa = Unknown
        (B) LOCATION: 100, 114, 144

(xi) SEQUENCE DESCRIPTION: SEQ ID NO:19:

```
A GTT AGT CTT TCC AAT TCG ATC AGA CCT TCT TGT TTA TGG             40
  Val Ser Leu Ser Asn Ser Ile Arg Pro Ser Cys Leu Trp
  1               5                  10

GCC AAT GAC GAG TTC GAC ACA GAT AGT TCA ATT GCT ACT GGT           82
Ala Asn Asp Glu Phe Asp Thr Asp Ser Ser Ile Ala Thr Gly
        15                  20                  25

TGG GGA AAG ATA GAC TAT GCT GAG AGC AGA AGT GAT GAC CTA           124
Trp Gly Lys Ile Asp Tyr Ala Glu Ser Arg Ser Asp Asp Leu
            30                  35                  40

CTG AAA GTA GTA CTG AAA ATT ATT GAT AAT AGG CAA TGC GCT           166
Leu Lys Val Val Leu Lys Ile Ile Asp Asn Arg Gln Cys Ala
                45                  50                  55

CCC TTA TAC GTT GAT CAG ATT AAT AGA AGA AGA TTG AGA AAT           208
Pro Leu Tyr Val Asp Gln Ile Asn Arg Arg Arg Leu Arg Asn
                    60                  65

GGA ATT GTA GAT ACA CAG ATG TGT GCA GGA GAA TTG GAT GGT           250
Gly Ile Val Asp Thr Gln Met Cys Ala Gly Glu Leu Asp Gly
    70                  75                  80

GGC AAA GAC ACT TGC CAG GGA GAT TCA GGT GGG CCA TTG CAA           292
Gly Lys Asp Thr Cys Gln Gly Asp Ser Gly Gly Pro Leu Gln
        85                  90                  95

ATA ACA AAW CAA AGC AAC AAA TGT ATC TTC TAC ATA GTG GGA           334
Ile Thr Xaa Gln Ser Asn Lys Cys Ile Phe Tyr Ile Val Gly
            100                 105                 110

ATA ACA TYA TTC GGA AGG GGA TGT GGT GCT CCT AAT AGC CCC           376
Ile Thr Xaa Phe Gly Arg Gly Cys Gly Ala Pro Asn Ser Pro
                115                 120                 125

GGT GTT TAT ACT AGA GTC AGY AAG TAT GTT GAC TGG ATT GAA           418
Gly Val Tyr Thr Arg Val Ser Lys Tyr Val Asp Trp Ile Glu
                    130                 135

AGT GTT GTT TGG SCA AAT                                           436
Ser Val Val Trp Xaa Asn
140                 145
```

-continued (2) INFORMATION FOR SEQ ID NO:20:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:20:

```
AACTATCTGT GTCGAACTCG TC                                              22
```

(2) INFORMATION FOR SEQ ID NO:21:

(i) SEQUENCE CHARACTERISTICS:
        (A) LENGTH: 1303 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 149..1300

(ix) FEATURE:
        (A) NAME/KEY: W = A or T/U
        (B) LOCATION: 1165

(ix) FEATURE:
        (A) NAME/KEY: Y = C or T/U
        (B) LOCATION: 1206,1261

(ix) FEATURE:
        (A) NAME/KEY: S = C or G
        (B) LOCATION: 1295

(ix) FEATURE:
        (A) NAME/KEY: Xaa = Unknown
        (B) LOCATION: 339, 353, 383

(xi) SEQUENCE DESCRIPTION: SEQ ID NO:21:

```
GCGAGGTGAG ACGTAATTAA GTTGTAAGTT GTGTCGTGTT GTGGAATATT                50

AATTAAAATT TTAGATATAT TTAAAAAAAA AGTTAAATCG GCATAGTGTT               100

GTTTTTGCGA ATGGTCGAAT TTCCCATTTG ACTTGCTTTT ATGTGATA                 148
```

```
ATG TTT TTG TTA ATA TGC GCG CTA TTG TTT GTA AAA AAC ATT              190
Met Phe Leu Leu Ile Cys Ala Leu Leu Phe Val Lys Asn Ile
 1               5                  10

GTA CTG ATA AAT GCT CAG ATA TCT GTG ATA GGC GAT AGT TGC              232
Val Leu Ile Asn Ala Gln Ile Ser Val Ile Gly Asp Ser Cys
 15              20                 25

ACT AGA AGT TAT GAT GGG GAG GCA GGT GAA TGC GCC CTG ATT              274
Thr Arg Ser Tyr Asp Gly Glu Ala Gly Glu Cys Ala Leu Ile
   30              35                 40

ACT CAA TGT CCT TCG GCA AAC CGC ATC CTT CAG ACC ACC GGC              316
Thr Gln Cys Pro Ser Ala Asn Arg Ile Leu Gln Thr Thr Gly
          45                 50                 55

ATC AGA CCT GAC GTA TGC GGT TAT TCT ACG TAT GAA CCG ATA              358
Ile Arg Pro Asp Val Cys Gly Tyr Ser Thr Tyr Glu Pro Ile
             60                 65                 70

GTT TGC TGC GTC CAA CAG AGA TAC AAT TCT AAC TGG AAT TCT              400
Val Cys Cys Val Gln Gln Arg Tyr Asn Ser Asn Trp Asn Ser
                75                 80
```

-continued

| | |
|---|---|
| AAC CGC GAA GGC AAC AAG AGG ATC AGC GAA CAA AAA TGT GAT<br>Asn Arg Glu Gly Asn Lys Arg Ile Ser Glu Gln Lys Cys Asp<br>85                    90                    95 | 442 |
| GGG TAC AGT ACT GCC GTA AAA CAA ACA TTG ACG GTT CTG CCA<br>Gly Tyr Ser Thr Ala Val Lys Gln Thr Leu Thr Val Leu Pro<br>100                   105                 110 | 484 |
| TTG GTG TCA GAC CCA AAT CCA ATA TCA TTT ACA GTT GAA AAA<br>Leu Val Ser Asp Pro Asn Pro Ile Ser Phe Thr Val Glu Lys<br>115                   120                 125 | 526 |
| TGT GAT TAC AAT AGC GTT CCT TTG ATC GTT GGA GGA GAA GTC<br>Cys Asp Tyr Asn Ser Val Pro Leu Ile Val Gly Gly Glu Val<br>130                   135                 140 | 568 |
| GCA AAA TTG GGC GAA TTT CCA CAT ATG GCA GCC ATC GGT TGG<br>Ala Lys Leu Gly Glu Phe Pro His Met Ala Ala Ile Gly Trp<br>145                   150 | 610 |
| ACA GAA ACT AGT GGG GCC GTA AAT TGG TGG TGC GGA GGC ACT<br>Thr Glu Thr Ser Gly Ala Val Asn Trp Trp Cys Gly Gly Thr<br>155                   160                 165 | 652 |
| TTA ATT AGT CCC GAA TAT GTA CTC ACA GCG GCG CAT TGT GCA<br>Leu Ile Ser Pro Glu Tyr Val Leu Thr Ala Ala His Cys Ala<br>170                   175                 180 | 694 |
| AGC GTA AAT AGT GAG CAA CCT GAT ATC GTT CGA CTT GGG GAA<br>Ser Val Asn Ser Glu Gln Pro Asp Ile Val Arg Leu Gly Glu<br>185                   190                 195 | 736 |
| CAT AAC TTA AAA CAT TCG GAC GAT GGG GCC GAT CCC ATT GAT<br>His Asn Leu Lys His Ser Asp Asp Gly Ala Asp Pro Ile Asp<br>200                   205                 210 | 778 |
| GTT CCA GTC GAT TCC GTC ATC ACT CAT CCT AGT TAT CAT TAT<br>Val Pro Val Asp Ser Val Ile Thr His Pro Ser Tyr His Tyr<br>215                   220 | 820 |
| CCA TCT AAA TAT AAT GAT ATT GCA CTA GTT AAA CTG CGG TAT<br>Pro Ser Lys Tyr Asn Asp Ile Ala Leu Val Lys Leu Arg Tyr<br>225                     230                 235 | 862 |
| CCA GTT AGT CTT TCC AAT TCG ATC AGA CCT TCT TGT CTA TGG<br>Pro Val Ser Leu Ser Asn Ser Ile Arg Pro Ser Cys Leu Trp<br>240                   245                 250 | 904 |
| GCC AAT GAC GAG TTC GAC ACA GAT AGT TCA ATT GCT ACT GGT<br>Ala Asn Asp Glu Phe Asp Thr Asp Ser Ser Ile Ala Thr Gly<br>255                   260                 265 | 946 |
| TGG GGA AAG ATA GAC TAT GCT GAG AGC AGA AGT GAT GAC CTA<br>Trp Gly Lys Ile Asp Tyr Ala Glu Ser Arg Ser Asp Asp Leu<br>270                   275                 280 | 988 |
| CTG AAA GTA GTA CTG AAA ATT ATT GAT AAT AGG CAA TGC GCT<br>Leu Lys Val Val Leu Lys Ile Ile Asp Asn Arg Gln Cys Ala<br>285                   290 | 1030 |
| CCC TTA TAC GTT GAT CAG ATT AAT AGA AGA AGA TTG AGA AAT<br>Pro Leu Tyr Val Asp Gln Ile Asn Arg Arg Arg Leu Arg Asn<br>295                   300                 305 | 1072 |
| GGA ATT GTA GAT ACA CAG ATG TGT GCA GGA GAA TTG GAT GGT<br>Gly Ile Val Asp Thr Gln Met Cys Ala Gly Glu Leu Asp Gly<br>310                   315                 320 | 1114 |
| GGC AAA GAC ACT TGC CAG GGA GAT TCA GGT GGG CCA TTG CAA<br>Gly Lys Asp Thr Cys Gln Gly Asp Ser Gly Gly Pro Leu Gln<br>325                   330                 335 | 1156 |
| ATA ACA AAW CAA AGC AAC AAA TGT ATC TTC TAC ATA GTG GGA<br>Ile Thr Xaa Gln Ser Asn Lys Cys Ile Phe Tyr Ile Val Gly<br>340                   345                 350 | 1198 |
| ATA ACA TYA TTC GGA AGG GGA TGT GGT GCT CCT AAT AGC CCC<br>Ile Thr Xaa Phe Gly Arg Gly Cys Gly Ala Pro Asn Ser Pro<br>355                   360 | 1240 |

```
GGT GTT TAT ACT AGA GTC AGY AAG TAT GTT GAC TGG ATT GAA      1282
Gly Val Tyr Thr Arg Val Ser Lys Tyr Val Asp Trp Ile Glu
365                 370                 375

AGT GTT GTT TGG SCA AAT TAA                                  1303
Ser Val Val Trp Xaa Asn
    380
```

(2) INFORMATION FOR SEQ ID NO:22:

(i) SEQUENCE CHARACTERISTICS:
        (A) LENGTH: 384 amino acids
        (B) TYPE: amino acid
        (D) TOPOLOGY: linear (ii) MOLECULE TYPE: Protein (ix) FEATURE:
        (A) NAME/KEY: Xaa = Unknown
        (B) LOCATION: 339, 353, 383

(xi) SEQUENCE DESCRIPTION: SEQ ID NO:22:

```
Met Phe Leu Leu Ile Cys Ala Leu Leu Phe Val Lys Asn Ile
 1               5                  10

Val Leu Ile Asn Ala Gln Ile Ser Val Ile Gly Asp Ser Cys
15                  20                  25

Thr Arg Ser Tyr Asp Gly Glu Ala Gly Glu Cys Ala Leu Ile
        30                  35                  40

Thr Gln Cys Pro Ser Ala Asn Arg Ile Leu Gln Thr Thr Gly
            45                  50                  55

Ile Arg Pro Asp Val Cys Gly Tyr Ser Thr Tyr Glu Pro Ile
                60                  65                  70

Val Cys Cys Val Gln Gln Arg Tyr Asn Ser Asn Trp Asn Ser
                    75                  80

Asn Arg Glu Gly Asn Lys Arg Ile Ser Glu Gln Lys Cys Asp
85                  90                  95

Gly Tyr Ser Thr Ala Val Lys Gln Thr Leu Thr Val Leu Pro
    100                 105                 110

Leu Val Ser Asp Pro Asn Pro Ile Ser Phe Thr Val Glu Lys
        115                 120                 125

Cys Asp Tyr Asn Ser Val Pro Leu Ile Val Gly Gly Glu Val
            130                 135                 140

Ala Lys Leu Gly Glu Phe Pro His Met Ala Ala Ile Gly Trp
                145                 150

Thr Glu Thr Ser Gly Ala Val Asn Trp Trp Cys Gly Gly Thr
155                 160                 165

Leu Ile Ser Pro Glu Tyr Val Leu Thr Ala Ala His Cys Ala
    170                 175                 180

Ser Val Asn Ser Glu Gln Pro Asp Ile Val Arg Leu Gly Glu
        185                 190                 195

His Asn Leu Lys His Ser Asp Asp Gly Ala Asp Pro Ile Asp
            200                 205                 210

Val Pro Val Asp Ser Val Ile Thr His Pro Ser Tyr His Tyr
                215                 220

Pro Ser Lys Tyr Asn Asp Ile Ala Leu Val Lys Leu Arg Tyr
225                 230                 235

Pro Val Ser Leu Ser Asn Ser Ile Arg Pro Ser Cys Leu Trp
    240                 245                 250
```

```
Ala Asn Asp Glu Phe Asp Thr Asp Ser Ser Ile Ala Thr Gly
            255                 260                 265

Trp Gly Lys Ile Asp Tyr Ala Glu Ser Arg Ser Asp Asp Leu
            270                 275                 280

Leu Lys Val Val Leu Lys Ile Ile Asp Asn Arg Gln Cys Ala
                285                 290

Pro Leu Tyr Val Asp Gln Ile Asn Arg Arg Arg Leu Arg Asn
295                 300                 305

Gly Ile Val Asp Thr Gln Met Cys Ala Gly Glu Leu Asp Gly
    310                 315                 320

Gly Lys Asp Thr Cys Gln Gly Asp Ser Gly Gly Pro Leu Gln
            325                 330                 335

Ile Thr Xaa Gln Ser Asn Lys Cys Ile Phe Tyr Ile Val Gly
            340                 345                 350

Ile Thr Xaa Phe Gly Arg Gly Cys Gly Ala Pro Asn Ser Pro
                355                 360

Gly Val Tyr Thr Arg Val Ser Lys Tyr Val Asp Trp Ile Glu
365                 370                 375

Ser Val Val Trp Xaa Asn
    380
```

(2) INFORMATION FOR SEQ ID NO:23:

(i) SEQUENCE CHARACTERISTICS:
        (A) LENGTH: 1303 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: R = A or G
        (B) LOCATION: 43, 98

(ix) FEATURE:
        (A) NAME/KEY: W = A or T/U
        (B) LOCATION: 139

(ix) FEATURE:
        (A) NAME/KEY: S = C or G
        (B) LOCATION: 9

(xi) SEQUENCE DESCRIPTION: SEQ ID NO:23:

```
TTAATTTGSC CAAACAACAC TTTCAATCCA GTCAACATAC TTRCTGACTC         50

TAGTATAAAC ACCGGGGCTA TTAGGAGCAC CACATCCCCT TCCGAATRAT        100

GTTATTCCCA CTATGTAGAA GATACATTTG TTGCTTTGWT TTGTTATTTG        150

CAATGGCCCA CCTGAATCTC CCTGGCAAGT GTCTTTGCCA CCATCCAATT        200

CTCCTGCACA CATCTGTGTA TCTACAATTC CATTTCTCAA TCTTCTTCTA        250

TTAATCTGAT CAACGTATAA GGGAGCGCAT TGCCTATTAT CAATAATTTT        300

CAGTACTACT TTCAGTAGGT CATCACTTCT GCTCTCAGCA TAGTCTATCT        350

TTCCCCAACC AGTAGCAATT GAACTATCTG TGTCGAACTC GTCATTGGCC        400

CATAGACAAG AAGGTCTGAT CGAATTGGAA AGACTAACTG GATACCGCAG        450

TTTAACTAGT GCAATATCAT TATATTTAGA TGGATAATGA TAACTAGGAT        500

GAGTGATGAC GGAATCGACT GGAACATCAA TGGGATCGGC CCCATCGTCC        550

GAATGTTTTA AGTTATGTTC CCCAAGTCGA ACGATATCAG GTTGCTCACT        600
```

-continued

| | |
|---|---|
| ATTTACGCTT GCACAATGCG CCGCTGTGAG TACATATTCG GGACTAATTA | 650 |
| AAGTGCCTCC GCACCACCAA TTTACGGCCC CACTAGTTTC TGTCCAACCG | 700 |
| ATGGCTGCCA TATGTGGAAA TTCGCCCAAT TTTGCGACTT CTCCTCCAAC | 750 |
| GATCAAAGGA ACGCTATTGT AATCACATTT TCAACTGTA AATGATATTG | 800 |
| GATTTGGGTC TGACACCAAT GGCAGAACCG TCAATGTTTG TTTTACGGCA | 850 |
| GTACTGTACC CATCACATTT TTGTTCGCTG ATCCTCTTGT TGCCTTCGCG | 900 |
| GTTAGAATTC CAGTTAGAAT TGTATCTCTG TTGGACGCAG CAAACTATCG | 950 |
| GTTCATACGT AGAATAACCG CATACGTCAG GTCTGATGCC GGTGGTCTGA | 1000 |
| AGGATGCGGT TTGCCGAAGG ACATTGAGTA ATCAGGGCGC ATTCACCTGC | 1050 |
| CTCCCCATCA TAACTTCTAG TGCAACTATC GCCTATCACA GATATCTGAG | 1100 |
| CATTTATCAG TACAATGTTT TTTACAAACA ATAGCGCGCA TATTAACAAA | 1150 |
| AACATTATCA CATAAAAGCA AGTCAAATGG GAAATTCGAC CATTCGCAAA | 1200 |
| AACAACACTA TGCCGATTTA ACTTTTTTTT TAAATATATC TAAAATTTTA | 1250 |
| ATTAATATTC CACAACACGA CACAACTTAC AACTTAATTA CGTCTCACCT | 1300 |
| CGC | 1303 |

(2) INFORMATION FOR SEQ ID NO:24:

(i) SEQUENCE CHARACTERISTICS:
        (A) LENGTH: 1152 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1152

(ix) FEATURE:
        (A) NAME/KEY: W = A or T/U
        (B) LOCATION: 1017

(ix) FEATURE:
        (A) NAME/KEY: Y = C or T/U
        (B) LOCATION: 1058, 1113

(ix) FEATURE:
        (A) NAME/KEY: S = C or G
        (B) LOCATION: 1147

(ix) FEATURE:
        (A) NAME/KEY: Xaa = Unknown
        (B) LOCATION: 339, 353, 383

(xi) SEQUENCE DESCRIPTION: SEQ ID NO:24:

| | |
|---|---|
| ATG TTT TTG TTA ATA TGC GCG CTA TTG TTT GTA AAA AAC ATT<br>Met Phe Leu Leu Ile Cys Ala Leu Leu Phe Val Lys Asn Ile<br>1                5                  10 | 42 |
| GTA CTG ATA AAT GCT CAG ATA TCT GTG ATA GGC GAT AGT TGC<br>Val Leu Ile Asn Ala Gln Ile Ser Val Ile Gly Asp Ser Cys<br>  15              20                 25 | 84 |
| ACT AGA AGT TAT GAT GGG GAG GCA GGT GAA TGC GCC CTG ATT<br>Thr Arg Ser Tyr Asp Gly Glu Ala Gly Glu Cys Ala Leu Ile<br>      30              35                 40 | 126 |
| ACT CAA TGT CCT TCG GCA AAC CGC ATC CTT CAG ACC ACC GGC<br>Thr Gln Cys Pro Ser Ala Asn Arg Ile Leu Gln Thr Thr Gly<br>            45              50              55 | 168 |

```
ATC AGA CCT GAC GTA TGC GGT TAT TCT ACG TAT GAA CCG ATA              210
Ile Arg Pro Asp Val Cys Gly Tyr Ser Thr Tyr Glu Pro Ile
            60                  65                  70

GTT TGC TGC GTC CAA CAG AGA TAC AAT TCT AAC TGG AAT TCT              252
Val Cys Cys Val Gln Gln Arg Tyr Asn Ser Asn Trp Asn Ser
                75                  80

AAC CGC GAA GGC AAC AAG AGG ATC AGC GAA CAA AAA TGT GAT              294
Asn Arg Glu Gly Asn Lys Arg Ile Ser Glu Gln Lys Cys Asp
 85                  90                  95

GGG TAC AGT ACT GCC GTA AAA CAA ACA TTG ACG GTT CTG CCA              336
Gly Tyr Ser Thr Ala Val Lys Gln Thr Leu Thr Val Leu Pro
    100                 105                 110

TTG GTG TCA GAC CCA AAT CCA ATA TCA TTT ACA GTT GAA AAA              378
Leu Val Ser Asp Pro Asn Pro Ile Ser Phe Thr Val Glu Lys
        115                 120                 125

TGT GAT TAC AAT AGC GTT CCT TTG ATC GTT GGA GGA GAA GTC              420
Cys Asp Tyr Asn Ser Val Pro Leu Ile Val Gly Gly Glu Val
            130                 135                 140

GCA AAA TTG GGC GAA TTT CCA CAT ATG GCA GCC ATC GGT TGG              462
Ala Lys Leu Gly Glu Phe Pro His Met Ala Ala Ile Gly Trp
                145                 150

ACA GAA ACT AGT GGG GCC GTA AAT TGG TGG TGC GGA GGC ACT              504
Thr Glu Thr Ser Gly Ala Val Asn Trp Trp Cys Gly Gly Thr
155                 160                 165

TTA ATT AGT CCC GAA TAT GTA CTC ACA GCG GCG CAT TGT GCA              546
Leu Ile Ser Pro Glu Tyr Val Leu Thr Ala Ala His Cys Ala
    170                 175                 180

AGC GTA AAT AGT GAG CAA CCT GAT ATC GTT CGA CTT GGG GAA              588
Ser Val Asn Ser Glu Gln Pro Asp Ile Val Arg Leu Gly Glu
        185                 190                 195

CAT AAC TTA AAA CAT TCG GAC GAT GGG GCC GAT CCC ATT GAT              630
His Asn Leu Lys His Ser Asp Asp Gly Ala Asp Pro Ile Asp
            200                 205                 210

GTT CCA GTC GAT TCC GTC ATC ACT CAT CCT AGT TAT CAT TAT              672
Val Pro Val Asp Ser Val Ile Thr His Pro Ser Tyr His Tyr
                215                 220

CCA TCT AAA TAT AAT GAT ATT GCA CTA GTT AAA CTG CGG TAT              714
Pro Ser Lys Tyr Asn Asp Ile Ala Leu Val Lys Leu Arg Tyr
225                 230                 235

CCA GTT AGT CTT TCC AAT TCG ATC AGA CCT TCT TGT CTA TGG              756
Pro Val Ser Leu Ser Asn Ser Ile Arg Pro Ser Cys Leu Trp
    240                 245                 250

GCC AAT GAC GAG TTC GAC ACA GAT AGT TCA ATT GCT ACT GGT              798
Ala Asn Asp Glu Phe Asp Thr Asp Ser Ser Ile Ala Thr Gly
        255                 260                 265

TGG GGA AAG ATA GAC TAT GCT GAG AGC AGA AGT GAT GAC CTA              840
Trp Gly Lys Ile Asp Tyr Ala Glu Ser Arg Ser Asp Asp Leu
            270                 275                 280

CTG AAA GTA GTA CTG AAA ATT ATT GAT AAT AGG CAA TGC GCT              882
Leu Lys Val Val Leu Lys Ile Ile Asp Asn Arg Gln Cys Ala
                285                 290

CCC TTA TAC GTT GAT CAG ATT AAT AGA AGA AGA TTG AGA AAT              924
Pro Leu Tyr Val Asp Gln Ile Asn Arg Arg Arg Leu Arg Asn
295                 300                 305

GGA ATT GTA GAT ACA CAG ATG TGT GCA GGA GAA TTG GAT GGT              966
Gly Ile Val Asp Thr Gln Met Cys Ala Gly Glu Leu Asp Gly
    310                 315                 320

GGC AAA GAC ACT TGC CAG GGA GAT TCA GGT GGG CCA TTG CAA             1008
Gly Lys Asp Thr Cys Gln Gly Asp Ser Gly Gly Pro Leu Gln
        325                 330                 335
```

```
ATA ACA AAW CAA AGC AAC AAA TGT ATC TTC TAC ATA GTG GGA                    1050
Ile Thr Xaa Gln Ser Asn Lys Cys Ile Phe Tyr Ile Val Gly
            340                 345                 350

ATA ACA TYA TTC GGA AGG GGA TGT GGT GCT CCT AAT AGC CCC                    1092
Ile Thr Xaa Phe Gly Arg Gly Cys Gly Ala Pro Asn Ser Pro
            355                 360

GGT GTT TAT ACT AGA GTC AGY AAG TAT GTT GAC TGG ATT GAA                    1134
Gly Val Tyr Thr Arg Val Ser Lys Tyr Val Asp Trp Ile Glu
365                 370                 375

AGT GTT GTT TGG SCA AAT                                                     1152
Ser Val Val Trp Xaa Asn
    380
```

(2) INFORMATION FOR SEQ ID NO:25:

(i) SEQUENCE CHARACTERISTICS:
        (A) LENGTH: 1152 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: S = C or G
        (B) LOCATION: 6

(ix) FEATURE:
        (A) NAME/KEY: R = A or G
        (B) LOCATION: 40, 95

(ix) FEATURE:
        (A) NAME/KEY: W = A or T/U
        (B) LOCATION: 136

(xi) SEQUENCE DESCRIPTION: SEQ ID NO:25:

```
ATTTGSCCAA ACAACACTTT CAATCCAGTC AACATACTTR CTGACTCTAG         50

TATAAACACC GGGGCTATTA GGAGCACCAC ATCCCCTTCC GAATRATGTT         100

ATTCCCACTA TGTAGAAGAT ACATTTGTTG CTTTGWTTTG TTATTTGCAA         150

TGGCCCACCT GAATCTCCCT GGCAAGTGTC TTTGCCACCA TCCAATTCTC         200

CTGCACACAT CTGTGTATCT ACAATTCCAT TTCTCAATCT TCTTCTATTA         250

ATCTGATCAA CGTATAAGGG AGCGCATTGC CTATTATCAA TAATTTTCAG         300

TACTACTTTC AGTAGGTCAT CACTTCTGCT CTCAGCATAG TCTATCTTTC         350

CCCAACCAGT AGCAATTGAA CTATCTGTGT CGAACTCGTC ATTGGCCCAT         400

AGACAAGAAG GTCTGATCGA ATTGGAAAGA CTAACTGGAT ACCGCAGTTT         450

AACTAGTGCA ATATCATTAT ATTTAGATGG ATAATGATAA CTAGGATGAG         500

TGATGACGGA ATCGACTGGA ACATCAATGG GATCGGCCCC ATCGTCCGAA         550

TGTTTTAAGT TATGTTCCCC AAGTCGAACG ATATCAGGTT GCTCACTATT         600

TACGCTTGCA CAATGCGCCG CTGTGAGTAC ATATTCGGGA CTAATTAAAG         650

TGCCTCCGCA CCACCAATTT ACGGCCCCAC TAGTTTCTGT CCAACCGATG         700

GCTGCCATAT GTGGAAATTC GCCCAATTTT GCGACTTCTC CTCCAACGAT         750

CAAAGGAACG CTATTGTAAT CACATTTTTC AACTGTAAAT GATATTGGAT         800

TTGGGTCTGA CACCAATGGC AGAACCGTCA ATGTTTGTTT TACGGCAGTA         850

CTGTACCCAT CACATTTTTG TTCGCTGATC CTCTTGTTGC CTTCGCGGTT         900

AGAATTCCAG TTAGAATTGT ATCTCTGTTG GACGCAGCAA ACTATCGGTT         950
```

-continued

```
CATACGTAGA ATAACCGCAT ACGTCAGGTC TGATGCCGGT GGTCTGAAGG          1000

ATGCGGTTTG CCGAAGGACA TTGAGTAATC AGGGCGCATT CACCTGCCTC          1050

CCCATCATAA CTTCTAGTGC AACTATCGCC TATCACAGAT ATCTGAGCAT          1100

TTATCAGTAC AATGTTTTTT ACAAACAATA GCGCGCATAT TAACAAAAAC          1150

AT                                                             1152
```

(2) INFORMATION FOR SEQ ID NO:26:

(i) SEQUENCE CHARACTERISTICS:
        (A) LENGTH: 945 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..768

(xi) SEQUENCE DESCRIPTION: SEQ ID NO:26:

```
CTG AAG TGT GGA TTC ATC GTT GTT TTC CTT GTG GCG GCA GCT           42
Leu Lys Cys Gly Phe Ile Val Val Phe Leu Val Ala Ala Ala
 1               5                  10

TTG GGT GAA GAT TCG GTC GTC GAC CGC ATC GTC GGC GGC ACC           84
Leu Gly Glu Asp Ser Val Val Asp Arg Ile Val Gly Gly Thr
 15              20                  25

AGT GTT AAA ATT GAG AAC TTC GGA TGG CAA GTG TCC TTA TTC          126
Ser Val Lys Ile Glu Asn Phe Gly Trp Gln Val Ser Leu Phe
     30              35                  40

GAT CGT AAG GGT CAC TTT TGC GGT GGT TCT ATA ATC AGC GAC          168
Asp Arg Lys Gly His Phe Cys Gly Gly Ser Ile Ile Ser Asp
         45              50                  55

GAA TGG GTC TTG ACT GCT GCA CAT TGC GTA TAC GAT TAT TTC          210
Glu Trp Val Leu Thr Ala Ala His Cys Val Tyr Asp Tyr Phe
             60              65                  70

TCG CCA AAG CAA TAT GGA GTG CGT GTC GGA AGC AGT TTA CGC          252
Ser Pro Lys Gln Tyr Gly Val Arg Val Gly Ser Ser Leu Arg
                 75              80

AAC AAA GGT GGA GTC CTT CAC AGA ATT TCC AGG GTA CAC ATT          294
Asn Lys Gly Gly Val Leu His Arg Ile Ser Arg Val His Ile
 85                  90                  95

CAC CCA GAC TAC GAC ACG GTC AGC TAC GAC AAT GAC GTC GCG          336
His Pro Asp Tyr Asp Thr Val Ser Tyr Asp Asn Asp Val Ala
     100                 105                 110

CTC CTG AAA GTT GAA ACC AAA TTT AAA CTA AAC GGC AGG AGC          378
Leu Leu Lys Val Glu Thr Lys Phe Lys Leu Asn Gly Arg Ser
             115                 120                 125

GTT CGC AAA GTT AAA TTG GTT GAC GAA GAT CAC GAG GTT GAT          420
Val Arg Lys Val Lys Leu Val Asp Glu Asp His Glu Val Asp
                 130                 135                 140

GAT GGT GCC CGG CTC ACC GTC ACT GGA TGG GGC AAA TTA AGT          462
Asp Gly Ala Arg Leu Thr Val Thr Gly Trp Gly Lys Leu Ser
                     145                 150

GAA TCA GGA CCC AAG CCA GTA AAT CTA CAA GGA GTA AAA GTG          504
Glu Ser Gly Pro Lys Pro Val Asn Leu Gln Gly Val Lys Val
155                 160                 165

CCT TAT GTG GAC CAA GAT ACA TGC TCT GAC AGC TAC GTC TTT          546
Pro Tyr Val Asp Gln Asp Thr Cys Ser Asp Ser Tyr Val Phe
         170                 175                 180
```

```
GCA GGA AAA GAT ATC ACC GAA AAC ATG TTG TGT GCC GGA GTT            588
Ala Gly Lys Asp Ile Thr Glu Asn Met Leu Cys Ala Gly Val
        185                 190                 195

AGA AGA GGT GGC AAG GAC TCC TGC CAG GGT GAC AGC GGT GGT            630
Arg Arg Gly Gly Lys Asp Ser Cys Gln Gly Asp Ser Gly Gly
            200                 205                 210

CCA CTT TG GAC GAA AAC AAA AAT CTG GTC GGA GTC GTC TCT             672
Pro Leu Val Asp Glu Asn Lys Asn Leu Val Gly Val Val Ser
                215                 220

TGG GGA AAT GGT TGT GCC AGA CCA AAC ATG CCA GGA GTA TAC            714
Trp Gly Asn Gly Cys Ala Arg Pro Asn Met Pro Gly Val Tyr
225                 230                 235

GCT AAA GTT GCT GCT TCT AGC ATT AGA GAG TTC ATT CGC AAA            756
Ala Lys Val Ala Ala Ser Ser Ile Arg Glu Phe Ile Arg Lys
        240                 245                 250

AAA ACT GGT CTT TAA TTTCCTTATA TGAACAAATG TTCCACCAAA               801
Lys Thr Gly Leu
            255

AATATAGTTT AGATTTTAGT ATAATAAATC CTTTGTGATT CATGCAAATA             851

TTTTGTTTTA TTTATTTATT TACTTTATTC AAACGAATGT ATAAAGTGAA             901

TTAACAATAA AAATGTTAGT GTTGCCAAAA AAAAAAAAA AAAA                    945

(2) INFORMATION FOR SEQ ID NO:27:

(i) SEQUENCE CHARACTERISTICS:
        (A) LENGTH: 256 amino acids
        (B) TYPE: amino acid
        (D) TOPOLOGY: linear (ii) MOLECULE TYPE: Protein (xi) SEQUENCE DESCRIPTION: SEQ ID NO:27:

Leu Lys Cys Gly Phe Ile Val Val Phe Leu Val Ala Ala Ala
  1               5                  10

Leu Gly Glu Asp Ser Val Val Asp Arg Ile Val Gly Gly Thr
 15                  20                  25

Ser Val Lys Ile Glu Asn Phe Gly Trp Gln Val Ser Leu Phe
     30                  35                  40

Asp Arg Lys Gly His Phe Cys Gly Gly Ser Ile Ile Ser Asp
         45                  50                  55

Glu Trp Val Leu Thr Ala Ala His Cys Val Tyr Asp Tyr Phe
             60                  65                  70

Ser Pro Lys Gln Tyr Gly Val Arg Val Gly Ser Ser Leu Arg
                 75                  80

Asn Lys Gly Gly Val Leu His Arg Ile Ser Arg Val His Ile
 85                  90                  95

His Pro Asp Tyr Asp Thr Val Ser Tyr Asp Asn Asp Val Ala
        100                 105                 110

Leu Leu Lys Val Glu Thr Lys Phe Lys Leu Asn Gly Arg Ser
            115                 120                 125

Val Arg Lys Val Lys Leu Val Asp Glu Asp His Glu Val Asp
                130                 135                 140

Asp Gly Ala Arg Leu Thr Val Thr Gly Trp Gly Lys Leu Ser
                145                 150

Glu Ser Gly Pro Lys Pro Val Asn Leu Gln Gly Val Lys Val
155                 160                 165
```

```
Pro Tyr Val Asp Gln Asp Thr Cys Ser Asp Ser Tyr Val Phe
    170                 175                 180

Ala Gly Lys Asp Ile Thr Glu Asn Met Leu Cys Ala Gly Val
        185                 190                 195

Arg Arg Gly Gly Lys Asp Ser Cys Gln Gly Asp Ser Gly Gly
                200                 205                 210

Pro Leu Val Asp Glu Asn Lys Asn Leu Val Gly Val Val Ser
                215                 220

Trp Gly Asn Gly Cys Ala Arg Pro Asn Met Pro Gly Val Tyr
225             230                 235

Ala Lys Val Ala Ala Ser Ser Ile Arg Glu Phe Ile Arg Lys
    240                 245                 250

Lys Thr Gly Leu
        255
```

(2) INFORMATION FOR SEQ ID NO:28:

(i) SEQUENCE CHARACTERISTICS:
        (A) LENGTH: 945 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
TTTTTTTTTT TTTTTTTTGG CAACACTAAC ATTTTTATTG TTAATTCACT         50

TTATACATTC GTTTGAATAA AGTAAATAAA TAAATAAAAC AAAATATTTG        100

CATGAATCAC AAAGGATTTA TTATACTAAA ATCTAAACTA TATTTTTGGT        150

GGAACATTTG TTCATATAAG GAAATTAAAG ACCAGTTTTT TTGCGAATGA        200

ACTCTCTAAT GCTAGAAGCA GCAACTTTAG CGTATACTCC TGGCATGTTT        250

GGTCTGGCAC AACCATTTCC CCAAGAGACG ACTCCGACCA GATTTTTGTT        300

TTCGTCCACA GTGGACCAC CGCTGTCACC CTGGCAGGAG TCCTTGCCAC         350

CTCTTCTAAC TCCGGCACAC AACATGTTTT CGGTGATATC TTTTCCTGCA        400

AAGACGTAGC TGTCAGAGCA TGTATCTTGG TCCACATAAG GCACTTTTAC        450

TCCTTGTAGA TTTACTGGCT TGGGTCCTGA TTCACTTAAT TTGCCCCATC        500

CAGTGACGGT GAGCCGGGCA CCATCATCAA CCTCGTGATC TTCGTCAACC        550

AATTTAACTT TGCGAACGCT CCTGCCGTTT AGTTTAAATT TGGTTTCAAC        600

TTTCAGGAGC GCGACGTCAT TGTCGTAGCT GACCGTGTCG TAGTCTGGGT        650

GAATGTGTAC CCTGGAAATT CTGTGAAGGA CTCCACCTTT GTTGCGTAAA        700

CTGCTTCCGA CACGCACTCC ATATTGCTTT GGCGAGAAAT AATCGTATAC        750

GCAATGTGCA GCAGTCAAGA CCCATTCGTC GCTGATTATA GAACCACCGC        800

AAAAGTGACC CTTACGATCG AATAAGGACA CTTGCCATCC GAAGTTCTCA        850

ATTTTAACAC TGGTGCCGCC GACGATGCGG TCGACGACCC AATCTTCACC        900

CAAAGCTGCC GCCACAAGGA AACAACGAT GAATCCACAC TTCAG             945
```

(2) INFORMATION FOR SEQ ID NO:29:

(i) SEQUENCE CHARACTERISTICS:
        (A) LENGTH: 768 nucleotides
        (B) TYPE: nucleic acid (C) STRANDEDNESS: single
        (D) TOPOLOGY: linear (ii) MOLECULE TYPE: cDNA (ix) FEATURE:
        (A) NAME/KEY: CDS
        (B) LOCATION: 1..768

(xi) SEQUENCE DESCRIPTION: SEQ ID NO:29:

```
CTG AAG TGT GGA TTC ATC GTT GTT TTC CTT GTG GCG GCA GCT              42
Leu Lys Cys Gly Phe Ile Val Val Phe Leu Val Ala Ala Ala
 1               5                  10

TTG GGT GAA GAT TCG GTC GTC GAC CGC ATC GTC GGC GGC ACC              84
Leu Gly Glu Asp Ser Val Val Asp Arg Ile Val Gly Gly Thr
 15              20                  25

AGT GTT AAA ATT GAG AAC TTC GGA TGG CAA GTG TCC TTA TTC             126
Ser Val Lys Ile Glu Asn Phe Gly Trp Gln Val Ser Leu Phe
     30              35                  40

GAT CGT AAG GGT CAC TTT TGC GGT GGT TCT ATA ATC AGC GAC             168
Asp Arg Lys Gly His Phe Cys Gly Gly Ser Ile Ile Ser Asp
             45              50                  55

GAA TGG GTC TTG ACT GCT GCA CAT TGC GTA TAC GAT TAT TTC             210
Glu Trp Val Leu Thr Ala Ala His Cys Val Tyr Asp Tyr Phe
                 60              65                  70

TCG CCA AAG CAA TAT GGA GTG CGT GTC GGA AGC AGT TTA CGC             252
Ser Pro Lys Gln Tyr Gly Val Arg Val Gly Ser Ser Leu Ar
                     75              80

AAC AAA GGT GGA GTC CTT CAC AGA ATT TCC AGG GTA CAC ATT             294
Asn Lys Gly Gly Val Leu His Arg Ile Ser Arg Val His Ile
 85              90                  95

CAC CCA GAC TAC GAC ACG GTC AGC TAC GAC AAT GAC GTC GCG             336
His Pro Asp Tyr Asp Thr Val Ser Tyr Asp Asn Asp Val Ala
     100             105                 110

CTC CTG AAA GTT GAA ACC AAA TTT AAA CTA AAC GGC AGG AGC             378
Leu Leu Lys Val Glu Thr Lys Phe Lys Leu Asn Gly Arg Ser
         115             120                 125

GTT CGC AAA GTT AAA TTG GTT GAC GAA GAT CAC GAG GTT GAT             420
Val Arg Lys Val Lys Leu Val Asp Glu Asp His Glu Val Asp
             130             135                 140

GAT GGT GCC CGG CTC ACC GTC ACT GGA TGG GGC AAA TTA AGT             462
Asp Gly Ala Arg Leu Thr Val Thr Gly Trp Gly Lys Leu Ser
                 145             150

GAA TCA GGA CCC AAG CCA GTA AAT CTA CAA GGA GTA AAA GTG             504
Glu Ser Gly Pro Lys Pro Val Asn Leu Gln Gly Val Lys Val
155             160                 165

CCT TAT GTG GAC CAA GAT ACA TGC TCT GAC AGC TAC GTC TTT             546
Pro Tyr Val Asp Gln Asp Thr Cys Ser Asp Ser Tyr Val Phe
    170             175                 180

GCA GGA AAA GAT ATC ACC GAA AAC ATG TTG TGT GCC GGA GTT             588
Ala Gly Lys Asp Ile Thr Glu Asn Met Leu Cys Ala Gly Val
        185             190                 195

AGA AGA GGT GGC AAG GAC TCC TGC CAG GGT GAC AGC GGT GGT             630
Arg Arg Gly Gly Lys Asp Ser Cys Gln Gly Asp Ser Gly Gly
            200             205                 210

CCA CTT GTG GAC GAA AAC AAA AAT CTG GTC GGA GTC GTC TCT             672
Pro Leu Val Asp Glu Asn Lys Asn Leu Val Gly Val Val Ser
                215             220

TGG GGA AAT GGT TGT GCC AGA CCA AAC ATG CCA GGA GTA TAC             714
Trp Gly Asn Gly Cys Ala Arg Pro Asn Met Pro Gly Val Tyr
225             230                 235
```

| | | |
|---|---|---|
| GCT AAA GTT GCT GCT TCT AGC ATT AGA GAG TTC ATT CGC AAA<br>Ala Lys Val Ala Ala Ser Ser Ile Arg Glu Phe Ile Arg Lys<br>    240             245             250 | | 756 |
| AAA ACT GGT CTT<br>Lys Thr Gly Leu<br>        255 | | 768 |

(2) INFORMATION FOR SEQ ID NO:30:

(i) SEQUENCE CHARACTERISTICS:
        (A) LENGTH: 768 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

| | |
|---|---|
| AAGACCAGTT TTTTTGCGAA TGAACTCTCT AATGCTAGAA GCAGCAACTT | 50 |
| TAGCGTATAC TCCTGGCATG TTTGGTCTGG CACAACCATT TCCCCAAGAG | 100 |
| ACGACTCCGA CCAGATTTTT GTTTTCGTCC ACAAGTGGAC CACCGCTGTC | 150 |
| ACCCTGGCAG GAGTCCTTGC CACCTCTTCT AACTCCGGCA CACAACATGT | 200 |
| TTTCGGTGAT ATCTTTTCCT GCAAAGACGT AGCTGTCAGA GCATGTATCT | 250 |
| TGGTCCACAT AAGGCACTTT TACTCCTTGT AGATTTACTG GCTTGGGTCC | 300 |
| TGATTCACTT AATTTGCCCC ATCCAGTGAC GGTGAGCCGG GCACCATCAT | 350 |
| CAACCTCGTG ATCTTCGTCA ACCAATTTAA CTTTGCGAAC GCTCCTGCCG | 400 |
| TTTAGTTTAA ATTTGGTTTC AACTTTCAGG AGCGCGACGT CATTGTCGTA | 450 |
| GCTGACCGTG TCGTAGTCTG GGTGAATGTG TACCCTGGAA ATTCTGTGAA | 500 |
| GGACTCCACC TTTGTTGCGT AAACTGCTTC CGACACGCAC TCCATATTGC | 550 |
| TTTGGCGAGA ATAATCGTA TACGCAATGT GCAGCAGTCA AGACCCATTC | 600 |
| GTCGCTGATT ATAGAACCAC CGCAAAAGTG ACCCTTACGA TCGAATAAGG | 650 |
| ACACTTGCCA TCCGAAGTTC TCAATTTTAA CACTGGTGCC GCCGACGATG | 700 |
| CGGTCGACGA CCGAATCTTC ACCCAAAGCT GCCGCCACAA GGAAAACAAC | 750 |
| GATGAATCCA CACTTCAG | 768 |

(2) INFORMATION FOR SEQ ID NO:31:

(i) SEQUENCE CHARACTERISTICS:
        (A) LENGTH: 932 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..769

(ix) FEATURE:
        (A) NAME/KEY: K = G or T/U
        (B) LOCATION: 332

(ix) FEATURE:
        (A) NAME/KEY: Xaa = Unknown
        (B) LOCATION: 111

(xi) SEQUENCE DESCRIPTION: SEQ ID NO:31:

```
G TTC ATA TTT GTG CTC GTT TGC GTT GGA TTG AGC GCC GTC              40
  Phe Ile Phe Val Leu Val Cys Val Gly Leu Ser Ala Val
   1               5                  10

TCA TCT TAC AAG ATA AAG GAT GGA TTA GAT GGG CGC ATT GTT            82
Ser Ser Tyr Lys Ile Lys Asp Gly Leu Asp Gly Arg Ile Val
 15              20                  25

GGA GGA CAA GAT GCT GAT ATT GCC AAA TAT GGC TAT CAA GCT           124
Gly Gly Gln Asp Ala Asp Ile Ala Lys Tyr Gly Tyr Gln Ala
         30              35                  40

TCA CTC CAA GTA TTT AAC GAA CAT TTC TGT GGA GCT TCA ATA           166
Ser Leu Gln Val Phe Asn Glu His Phe Cys Gly Ala Ser Ile
             45                  50                  55

TTG AAT AAT TAT TGG ATT GTC ACA GCA GCT CAT TGC ATA TAT           208
Leu Asn Asn Tyr Trp Ile Val Thr Ala Ala His Cys Ile Tyr
                 60                  65

GAT GAA TTC ACG TAT TCA GTT CGA GTC GGC ACC AGT TTC CAA           250
Asp Glu Phe Thr Tyr Ser Val Arg Val Gly Thr Ser Phe Gln
 70              75                  80

GGA AGA CGT GGT TCC GTT CAT CCT GTG GCA CAA ATT ATC AAG           292
Gly Arg Arg Gly Ser Val His Pro Val Ala Gln Ile Ile Lys
         85                  90                  95

CAT CCT GCA TAC GGT AAT GTA ACT GAC ATC GAT ATG GAA KGC           334
His Pro Ala Tyr Gly Asn Val Thr Asp Ile Asp Met Glu Xaa
             100                 105                 110

GCC CTC ATC AAG GTT CGA AGA CCA TTC CGG TTG AAT AAC AGA           376
Ala Leu Ile Lys Val Arg Arg Pro Phe Arg Leu Asn Asn Arg
                 115                 120                 125

ACT GTT AGA ACA GTC AAA CTT ACT GAT GTT GGA AAA GAC ATG           418
Thr Val Arg Thr Val Lys Leu Thr Asp Val Gly Lys Asp Met
 130                 135

CCA TCA GGA GAA TTA GCC ACT GTT ACT GGC TGG GGA AAT TTA           460
Pro Ser Gly Glu Leu Ala Thr Val Thr Gly Trp Gly Asn Leu
140                 145                 150

GGG GAA GAT GAA GAC GAC CCC GAA CAA CTG CAA TAT GTA AAG           502
Gly Glu Asp Glu Asp Asp Pro Glu Gln Leu Gln Tyr Val Lys
    155                 160                 165

GTA CCT ATT GTT AAC TGG ACT CAG TGC AAA ACT ATA TAT GGA           544
Val Pro Ile Val Asn Trp Thr Gln Cys Lys Thr Ile Tyr Gly
        170                 175                 180

AAT GAA GGA CTA ATA ATT ACC CAA AAT ATG ATT TGT GCT GGT           586
Asn Glu Gly Leu Ile Ile Thr Gln Asn Met Ile Cys Ala Gly
            185                 190                 195

TAT CCT GAA GGC GGT AAG GAC TCT TGC CAA GGA GAT AGC GGT           628
Tyr Pro Glu Gly Gly Lys Asp Ser Cys Gln Gly Asp Ser Gly
                200                 205

GGC CCA CTC GTC AAC TCT AAG GGA GTT CTG CAT GGA ATA GTG           670
Gly Pro Leu Val Asn Ser Lys Gly Val Leu His Gly Ile Val
210                 215                 220

TCT TGG GGA ATA GGA TGT GCA CGA CCC GAA ATC CCA GGA GTA           712
Ser Trp Gly Ile Gly Cys Ala Arg Pro Glu Ile Pro Gly Val
        225                 230                 235

TAT ACC CGA GTG GCT TCA AAA CCA ATA AGA GAA TTT ATC AAA           754
Tyr Thr Arg Val Ala Ser Lys Pro Ile Arg Glu Phe Ile Lys
            240                 245                 250

ATG CAC ACT GGA ATA TAA GAGTTTTAAC TTATAATATT ACAAATATTT          802
Met His Thr Gly Ile
                255
```

-continued

```
TTTGATATTC CTTAATTTCA ATGATATACT AAGACGAGAT GTTTTACAAA                852

ATTTTGATAC TCAACTAACA AATTAAACCA TATTACTACT CAAATAAATA                902

TCACTAATAA TCAAAAAAAA AAAAAAAAAA                                      932
```

(2) INFORMATION FOR SEQ ID NO:32:

(i) SEQUENCE CHARACTERISTICS:
    (A) LENGTH: 256 amino acids
    (B) TYPE: amino acid
    (D) TOPOLOGY: linear (ii) MOLECULE TYPE: Protein (ix) FEATURE:
    (A) NAME/KEY: Xaa = any amino acid
    (B) LOCATION: 111

(xi) SEQUENCE DESCRIPTION: SEQ ID NO:32:

```
Phe Ile Phe Val Leu Val Cys Val Gly Leu Ser Ala Val
 1               5                  10

Ser Ser Tyr Lys Ile Lys Asp Gly Leu Asp Gly Arg Ile Val
         15                  20                  25

Gly Gly Gln Asp Ala Asp Ile Ala Lys Tyr Gly Tyr Gln Ala
         30                  35                  40

Ser Leu Gln Val Phe Asn Glu His Phe Cys Gly Ala Ser Ile
             45                  50                  55

Leu Asn Asn Tyr Trp Ile Val Thr Ala Ala His Cys Ile Tyr
                 60                  65

Asp Glu Phe Thr Tyr Ser Val Arg Val Gly Thr Ser Phe Gln
 70                  75                  80

Gly Arg Arg Gly Ser Val His Pro Val Ala Gln Ile Ile Lys
         85                  90                  95

His Pro Ala Tyr Gly Asn Val Thr Asp Ile Asp Met Glu Xaa
         100                 105                 110

Ala Leu Ile Lys Val Arg Arg Pro Phe Arg Leu Asn Asn Arg
             115                 120                 125

Thr Val Arg Thr Val Lys Leu Thr Asp Val Gly Lys Asp Met
                 130                 135

Pro Ser Gly Glu Leu Ala Thr Val Thr Gly Trp Gly Asn Leu
140                 145                 150

Gly Glu Asp Glu Asp Pro Glu Gln Leu Gln Tyr Val Lys
         155                 160                 165

Val Pro Ile Val Asn Trp Thr Gln Cys Lys Thr Ile Tyr Gly
             170                 175                 180

Asn Glu Gly Leu Ile Ile Thr Gln Asn Met Ile Cys Ala Gly
                 185                 190                 195

Tyr Pro Glu Gly Gly Lys Asp Ser Cys Gln Gly Asp Ser Gly
                 200                 205

Gly Pro Leu Val Asn Ser Lys Gly Val Leu His Gly Ile Val
210                 215                 220

Ser Trp Gly Ile Gly Cys Ala Arg Pro Glu Ile Pro Gly Val
    225                 230                 235

Tyr Thr Arg Val Ala Ser Lys Pro Ile Arg Glu Phe Ile Lys
        240                 245                 250

Met His Thr Gly Ile
            255
```

(2) INFORMATION FOR SEQ ID NO:33:

(i) SEQUENCE CHARACTERISTICS:
        (A) LENGTH: 932 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: M = A or C
        (B) LOCATION: 601, 657

(xi) SEQUENCE DESCRIPTION: SEQ ID NO:33:

| | | |
|---|---|---|
| TTTTTTTTTT TTTTTTTTGA TTATTAGTGA TATTTATTTG AGTAGTAATA | 50 |
| TGGTTTAATT TGTTAGTTGA GTATCAAAAT TTTGTAAAAC ATCTCGTCTT | 100 |
| AGTATATCAT TGAAATTAAG GAATATCAAA AATATTTGT AATATTATAA | 150 |
| GTTAAAACTC TTATATTCCA GTGTGCATTT TGATAAATTC TCTTATTGGT | 200 |
| TTTGAAGCCA CTCGGGTATA TACTCCTGGG ATTTCGGGTC GTGCACATCC | 250 |
| TATTCCCCAA GACACTATTC CATGCAGAAC TCCCTTAGAG TTGACGAGTG | 300 |
| GGCCACCGCT ATCTCCTTGG CAAGAGTCCT TACCGCCTTC AGGATAACCA | 350 |
| GCACAAATCA TATTTTGGGT AATTATTAGT CCTTCATTTC CATATATAGT | 400 |
| TTTGCACTGA GTCCAGTTAA CAATAGGTAC CTTTACATAT TGCAGTTGTT | 450 |
| CGGGGTCGTC TTCATCTTCC CCTAAATTTC CCCAGCCAGT AACAGTGGCT | 500 |
| AATTCTCCTG ATGGCATGTC TTTTCCAACA TCAGTAAGTT TGACTGTTCT | 550 |
| AACAGTTCTG TTATTCAACC GGAATGGTCT TCGAACCTTG ATGAGGGCGC | 600 |
| MTTCCATATC GATGTCAGTT ACATTACCGT ATGCAGGATG CTTGATAATT | 650 |
| TGTGCCMCAG GATGAACGGA ACCACGTCTT CCTTGGAAAC TGGTGCCGAC | 700 |
| TCGAACTGAA TACGTGAATT CATCATATAT GCAATGAGCT GCTGTGACAA | 750 |
| TCCAATAATT ATTCAATATT GAAGCTCCAC AGAAATGTTC GTTAAATACT | 800 |
| TGGAGTGAAG CTTGATAGCC ATATTTGGCA ATATCAGCAT CTTGTCCTCC | 850 |
| AACAATGCGC CCATCTAATC CATCCTTTAT CTTGTAAGAT GAGACGGCGC | 900 |
| TCAATCCAAC GCAAACGAGC ACAAATATGA AC | 932 |

(2) INFORMATION FOR SEQ ID NO:34:

(i) SEQUENCE CHARACTERISTICS:
        (A) LENGTH: 768 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..768

(ix) FEATURE:
        (A) NAME/KEY: K = G or T/U
        (B) LOCATION: 331

(ix) FEATURE:
        (A) NAME/KEY: Xaa = Unknown
        (B) LOCATION: 111

(xi) SEQUENCE DESCRIPTION: SEQ ID NO:34:

```
TTC ATA TTT GTG CTC GTT TGC GTT GGA TTG AGC GCC GTC           39
Phe Ile Phe Val Leu Val Cys Val Gly Leu Ser Ala Val
 1               5                  10

TCA TCT TAC AAG ATA AAG GAT GGA TTA GAT GGG CGC ATT GTT       81
Ser Ser Tyr Lys Ile Lys Asp Gly Leu Asp Gly Arg Ile Val
 15              20                  25

GGA GGA CAA GAT GCT GAT ATT GCC AAA TAT GGC TAT CAA GCT      123
Gly Gly Gln Asp Ala Asp Ile Ala Lys Tyr Gly Tyr Gln Ala
         30                  35                  40

TCA CTC CAA GTA TTT AAC GAA CAT TTC TGT GGA GCT TCA ATA      165
Ser Leu Gln Val Phe Asn Glu His Phe Cys Gly Ala Ser Ile
             45                  50                  55

TTG AAT AAT TAT TGG ATT GTC ACA GCA GCT CAT TGC ATA TAT      207
Leu Asn Asn Tyr Trp Ile Val Thr Ala Ala His Cys Ile Tyr
                 60                  65

GAT GAA TTC ACG TAT TCA GTT CGA GTC GGC ACC AGT TTC CAA      249
Asp Glu Phe Thr Tyr Ser Val Arg Val Gly Thr Ser Phe Gln
 70              75                  80

GGA AGA CGT GGT TCC GTT CAT CCT GTG GCA CAA ATT ATC AAG      291
Gly Arg Arg Gly Ser Val His Pro Val Ala Gln Ile Ile Lys
 85                  90                  95

CAT CCT GCA TAC GGT AAT GTA ACT GAC ATC GAT ATG GAA KGC      333
His Pro Ala Tyr Gly Asn Val Thr Asp Ile Asp Met Glu Xaa
             100                 105                 110

GCC CTC ATC AAG GTT CGA AGA CCA TTC CGG TTG AAT AAC AGA      375
Ala Leu Ile Lys Val Arg Arg Pro Phe Arg Leu Asn Asn Arg
                 115                 120                 125

ACT GTT AGA ACA GTC AAA CTT ACT GAT GTT GGA AAA GAC ATG      417
Thr Val Arg Thr Val Lys Leu Thr Asp Val Gly Lys Asp Met
                     130                 135

CCA TCA GGA GAA TTA GCC ACT GTT ACT GGC TGG GGA AAT TTA      459
Pro Ser Gly Glu Leu Ala Thr Val Thr Gly Trp Gly Asn Leu
140                 145                 150

GGG GAA GAT GAA GAC GAC CCC GAA CAA CTG CAA TAT GTA AAG      501
Gly Glu Asp Glu Asp Asp Pro Glu Gln Leu Gln Tyr Val Lys
         155                 160                 165

GTA CCT ATT GTT AAC TGG ACT CAG TGC AAA ACT ATA TAT GGA      543
Val Pro Ile Val Asn Trp Thr Gln Cys Lys Thr Ile Tyr Gly
             170                 175                 180

AAT GAA GGA CTA ATA ATT ACC CAA AAT ATG ATT TGT GCT GGT      585
Asn Glu Gly Leu Ile Ile Thr Gln Asn Met Ile Cys Ala Gly
                 185                 190                 195

TAT CCT GAA GGC GGT AAG GAC TCT TGC CAA GGA GAT AGC GGT      627
Tyr Pro Glu Gly Gly Lys Asp Ser Cys Gln Gly Asp Ser Gly
                     200                 205

GGC CCA CTC GTC AAC TCT AAG GGA GTT CTG CAT GGA ATA GTG      669
Gly Pro Leu Val Asn Ser Lys Gly Val Leu His Gly Ile Val
210                 215                 220

TCT TGG GGA ATA GGA TGT GCA CGA CCC GAA ATC CCA GGA GTA      711
Ser Trp Gly Ile Gly Cys Ala Arg Pro Glu Ile Pro Gly Val
225                 230                 235

TAT ACC CGA GTG GCT TCA AAA CCA ATA AGA GAA TTT ATC AAA      753
Tyr Thr Arg Val Ala Ser Lys Pro Ile Arg Glu Phe Ile Lys
         240                 245                 250

ATG CAC ACT GGA ATA                                          768
Met His Thr Gly Ile
             255
```

(2) INFORMATION FOR SEQ ID NO:35:

(i) SEQUENCE CHARACTERISTICS:
        (A) LENGTH: 768 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: M = A or C
        (B) LOCATION: 438, 494

(xi) SEQUENCE DESCRIPTION: SEQ ID NO:35:

```
TATTCCAGTG TGCATTTTGA TAAATTCTCT TATTGGTTTT GAAGCCACTC          50

GGGTATATAC TCCTGGGATT TCGGGTCGTG CACATCCTAT TCCCCAAGAC         100

ACTATTCCAT GCAGAACTCC CTTAGAGTTG ACGAGTGGGC CACCGCTATC         150

TCCTTGGCAA GAGTCCTTAC CGCCTTCAGG ATAACCAGCA CAAATCATAT         200

TTTGGGTAAT TATTAGTCCT TCATTTCCAT ATATAGTTTT GCACTGAGTC         250

CAGTTAACAA TAGGTACCTT TACATATTGC AGTTGTTCGG GGTCGTCTTC         300

ATCTTCCCCT AAATTTCCCC AGCCAGTAAC AGTGGCTAAT TCTCCTGATG         350

GCATGTCTTT TCCAACATCA GTAAGTTTGA CTGTTCTAAC AGTTCTGTTA         400

TTCAACCGGA ATGGTCTTCG AACCTTGATG AGGGCGCMTT CCATATCGAT         450

GTCAGTTACA TTACCGTATG CAGGATGCTT GATAATTTGT GCCMCAGGAT         500

GAACGGAACC ACGTCTTCCT TGGAAACTGG TGCCGACTCG AACTGAATAC         550

GTGAATTCAT CATATATGCA ATGAGCTGCT GTGACAATCC AATAATTATT         600

CAATATTGAA GCTCCACAGA AATGTTCGTT AAATACTTGG AGTGAAGCTT         650

GATAGCCATA TTTGGCAATA TCAGCATCTT GTCCTCCAAC AATGCGCCCA         700

TCTAATCCAT CCTTTATCTT GTAAGATGAG ACGGCGCTCA ATCCAACGCA         750

AACGAGCACA AATATGAA                                             768
```

(2) INFORMATION FOR SEQ ID NO:36:

(i) SEQUENCE CHARACTERISTICS:
        (A) LENGTH: 841 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..745

(xi) SEQUENCE DESCRIPTION: SEQ ID NO:36:

```
C TTA GCA ATT GTA TGT GCT CTC GCT GTC TGC ACA TTC GGT           40
  Leu Ala Ile Val Cys Ala Leu Ala Val Cys Thr Phe Gly
  1               5                   10

GCC AGT GTT CCA GAA TCA TGG AAA AGA TTA GAT AGT AGA ATC         82
Ala Ser Val Pro Glu Ser Trp Lys Arg Leu Asp Ser Arg Ile
    15                  20                  25

GTA GGA GGA CAC GAT ACC AGC ATC GAT AAA CAC CCT CAT CAA        124
Val Gly Gly His Asp Thr Ser Ile Asp Lys His Pro His Gln
        30                  35                  40
```

```
GTA TCT TTA TTG TAC TCC AGC CAC AAT TGT GGT GGT TCC TTG              166
Val Ser Leu Leu Tyr Ser Ser His Asn Cys Gly Gly Ser Leu
            45                  50                  55

ATT GCC AAA AAC TGG TGG GTT TTG ACT GCA GCT CAT TGC ATT              208
Ile Ala Lys Asn Trp Trp Val Leu Thr Ala Ala His Cys Ile
                60                  65

GGA GTT AAC AAA TAC AAT GTC CGT GTA GGA AGT TCC ATC GTA              250
Gly Val Asn Lys Tyr Asn Val Arg Val Gly Ser Ser Ile Val
70                  75                  80

AAC AGC GGT GGT ATC TTG CAT AAA GTT AAA AAC CAT TAC AGA              292
Asn Ser Gly Gly Ile Leu His Lys Val Lys Asn His Tyr Arg
    85                  90                  95

CAT CCA AAA TAC AAC GCA GCT GCT ATT GAC TTT GAT TAC GCA              334
His Pro Lys Tyr Asn Ala Ala Ala Ile Asp Phe Asp Tyr Ala
           100                 105                 110

CTC TTA GAA CTC GAA ACT CCT GTT CAA CTC ACA AAT GAT GTG              376
Leu Leu Glu Leu Glu Thr Pro Val Gln Leu Thr Asn Asp Val
               115                 120                 125

TCC ATC ATA AAA TTG GTC GAT GAA GGA GTA GAT CTT AAA CCT              418
Ser Ile Ile Lys Leu Val Asp Glu Gly Val Asp Leu Lys Pro
                   130                 135

GGT ACC TTG TTA ACT GTT ACT GGA TGG GGA TCA ACT GGA AAT              460
Gly Thr Leu Leu Thr Val Thr Gly Trp Gly Ser Thr Gly Asn
140                 145                 150

GGA CCT TCA ACC AAT GTT TTG CAA GAA GTT CAA GTA CCA CAT              502
Gly Pro Ser Thr Asn Val Leu Gln Glu Val Gln Val Pro His
    155                 160                 165

GTC GAC CAA ACC ACT TGC TCC AAA TCT TAC CCA GGA AGT TTG              544
Val Asp Gln Thr Thr Cys Ser Lys Ser Tyr Pro Gly Ser Leu
            170                 175                 180

ACT GAT CGT ATG TTC TGC GCT GGT TAT TTG GGA CAA GGA GGC              586
Thr Asp Arg Met Phe Cys Ala Gly Tyr Leu Gly Gln Gly Gly
                185                 190                 195

AAG GAC TCA TGC CAA GGT GAT TCT GGT GGC CCA GTT GTT GTC              628
Lys Asp Ser Cys Gln Gly Asp Ser Gly Gly Pro Val Val Val
                    200                 205

AAT GGT GTT CAA CAT GGA ATT GTC TCA TGG GGT CGT GGT TGT              670
Asn Gly Val Gln His Gly Ile Val Ser Trp Gly Arg Gly Cys
210                 215                 220

GCA CTT CCT GAT TAT CCT GGA GTT TAC TCT AAA ATC TCT ACC              712
Ala Leu Pro Asp Tyr Pro Gly Val Tyr Ser Lys Ile Ser Thr
    225                 230                 235

GCT CGC AGC TGG ATC AAG GAA GTG TCT GGT GTT TAA                      748
Ala Arg Ser Trp Ile Lys Glu Val Ser Gly Val
            240                 245

TTTATTCTTG AAATCTCTAT TTTGTATTAT TTATGTATAT AGTAAGAGTT              798

GTAAATATAA ATAGTTACAT CTAAAAAAAA AAAAAAAAA AAA                       841

(2) INFORMATION FOR SEQ ID NO:37:

(i) SEQUENCE CHARACTERISTICS:
        (A) LENGTH: 248 amino acids
        (B) TYPE: amino acid
        (D) TOPOLOGY: linear (ii) MOLECULE TYPE: Protein (xi) SEQUENCE DESCRIPTION: SEQ ID NO:37:

Leu Ala Ile Val Cys Ala Leu Ala Val Cys Thr Phe Gly
  1               5                  10
```

```
Ala Ser Val Pro Glu Ser Trp Lys Arg Leu Asp Ser Arg Ile
     15                  20                  25
Val Gly Gly His Asp Thr Ser Ile Asp Lys His Pro His Gln
             30                  35                  40
Val Ser Leu Leu Tyr Ser Ser His Asn Cys Gly Gly Ser Leu
                 45                  50                  55
Ile Ala Lys Asn Trp Trp Val Leu Thr Ala Ala His Cys Ile
                 60                      65
Gly Val Asn Lys Tyr Asn Val Arg Val Gly Ser Ser Ile Val
 70              75                      80
Asn Ser Gly Gly Ile Leu His Lys Val Lys Asn His Tyr Arg
 85                  90                      95
His Pro Lys Tyr Asn Ala Ala Ala Ile Asp Phe Asp Tyr Ala
            100                 105                 110
Leu Leu Glu Leu Glu Thr Pro Val Gln Leu Thr Asn Asp Val
                115                 120                 125
Ser Ile Ile Lys Leu Val Asp Glu Gly Val Asp Leu Lys Pro
                130                     135
Gly Thr Leu Leu Thr Val Thr Gly Trp Gly Ser Thr Gly Asn
140                 145                     150
Gly Pro Ser Thr Asn Val Leu Gln Glu Val Gln Val Pro His
    155                 160                     165
Val Asp Gln Thr Thr Cys Ser Lys Ser Tyr Pro Gly Ser Leu
        170                 175                     180
Thr Asp Arg Met Phe Cys Ala Gly Tyr Leu Gly Gln Gly Gly
            185                 190                     195
Lys Asp Ser Cys Gln Gly Asp Ser Gly Pro Val Val Val
                200                 205
Asn Gly Val Gln His Gly Ile Val Ser Trp Gly Arg Gly Cys
210                 215                     220
Ala Leu Pro Asp Tyr Pro Gly Val Tyr Ser Lys Ile Ser Thr
    225                 230                     235
Ala Arg Ser Trp Ile Lys Glu Val Ser Gly Val
        240                 245

(2) INFORMATION FOR SEQ ID NO:38:

(i) SEQUENCE CHARACTERISTICS:
        (A) LENGTH: 841 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

TTTTTTTTTT TTTTTTTTTT TAGATGTAAC TATTTATATT TACAACTCTT         50

ACTATATACA TAAATAATAC AAAATAGAGA TTTCAAGAAT AAATTAAACA        100

CCAGACACTT CCTTGATCCA GCTGCGAGCG GTAGAGATTT TAGAGTAAAC        150

TCCAGGATAA TCAGGAAGTG CACAACCACG ACCCCATGAG ACAATTCCAT        200

GTTGAACACC ATTGACAACA ACTGGGCCAC CAGAATCACC TTGGCATGAG        250

TCCTTGCCTC CTTGTCCCAA ATAACCAGCG CAGAACATAC GATCAGTCAA        300

ACTTCCTGGG TAAGATTTGG AGCAAGTGGT TTGGTCGACA TGTGGTACTT        350

GAACTTCTTG CAAAACATTG GTTGAAGGTC CATTTCCAGT TGATCCCCAT        400
```

```
CCAGTAACAG TTAACAAGGT ACCAGGTTTA AGATCTACTC CTTCATCGAC          450

CAATTTTATG ATGGACACAT CATTTGTGAG TTGAACAGGA GTTTCGAGTT          500

CTAAGAGTGC GTAATCAAAG TCAATAGCAG CTGCGTTGTA TTTTGGATGT          550

CTGTAATGGT TTTTAACTTT ATGCAAGATA CCACCGCTGT TTACGATGGA          600

ACTTCCTACA CGGACATTGT ATTTGTTAAC TCCAATGCAA TGAGCTGCAG          650

TCAAAACCCA CCAGTTTTTG GCAATCAAGG AACCACCACA ATTGTGGCTG          700

GAGTACAATA AAGATACTTG ATGAGGGTGT TTATCGATGC TGGTATCGTG          750

TCCTCCTACG ATTCTACTAT CTAATCTTTT CCATGATTCT GGAACACTGG          800

CACCGAATGT GCAGACAGCG AGAGCACATA CAATTGCTAA G                   841
```

(2) INFORMATION FOR SEQ ID NO:39:

(i) SEQUENCE CHARACTERISTICS:
        (A) LENGTH: 744 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..744

(xi) SEQUENCE DESCRIPTION: SEQ ID NO:39:

```
TTA GCA ATT GTA TGT GCT CTC GCT GTC TGC ACA TTC GGT              39
Leu Ala Ile Val Cys Ala Leu Ala Val Cys Thr Phe Gly
 1               5                  10

GCC AGT GTT CCA GAA TCA TGG AAA AGA TTA GAT AGT AGA ATC          81
Ala Ser Val Pro Glu Ser Trp Lys Arg Leu Asp Ser Arg Ile
         15                  20                  25

GTA GGA GGA CAC GAT ACC AGC ATC GAT AAA CAC CCT CAT CAA         123
Val Gly Gly His Asp Thr Ser Ile Asp Lys His Pro His Gln
             30                  35                  40

GTA TCT TTA TTG TAC TCC AGC CAC AAT TGT GGT GGT TCC TTG         165
Val Ser Leu Leu Tyr Ser Ser His Asn Cys Gly Gly Ser Leu
                 45                  50                  55

ATT GCC AAA AAC TGG TGG GTT TTG ACT GCA GCT CAT TGC ATT         207
Ile Ala Lys Asn Trp Trp Val Leu Thr Ala Ala His Cys Ile
                     60                  65

GGA GTT AAC AAA TAC AAT GTC CGT GTA GGA AGT TCC ATC GTA         249
Gly Val Asn Lys Tyr Asn Val Arg Val Gly Ser Ser Ile Val
 70                  75                  80

AAC AGC GGT GGT ATC TTG CAT AAA GTT AAA AAC CAT TAC AGA         291
Asn Ser Gly Gly Ile Leu His Lys Val Lys Asn His Tyr Arg
         85                  90                  95

CAT CCA AAA TAC AAC GCA GCT GCT ATT GAC TTT GAT TAC GCA         333
His Pro Lys Tyr Asn Ala Ala Ala Ile Asp Phe Asp Tyr Ala
            100                 105                 110

CTC TTA GAA CTC GAA ACT CCT GTT CAA CTC ACA AAT GAT GTG         375
Leu Leu Glu Leu Glu Thr Pro Val Gln Leu Thr Asn Asp Val
                115                 120                 125

TCC ATC ATA AAA TTG GTC GAT GAA GGA GTA GAT CTT AAA CCT         417
Ser Ile Ile Lys Leu Val Asp Glu Gly Val Asp Leu Lys Pro
                    130                 135

GGT ACC TTG TTA ACT GTT ACT GGA TGG GGA TCA ACT GGA AAT         459
Gly Thr Leu Leu Thr Val Thr Gly Trp Gly Ser Thr Gly Asn
140                 145                 150
```

```
GGA CCT TCA ACC AAT GTT TTG CAA GAA GTT CAA GTA CCA CAT         501
Gly Pro Ser Thr Asn Val Leu Gln Glu Val Gln Val Pro His
        155                 160                 165

GTC GAC CAA ACC ACT TGC TCC AAA TCT TAC CCA GGA AGT TTG         543
Val Asp Gln Thr Thr Cys Ser Lys Ser Tyr Pro Gly Ser Leu
        170                 175                 180

ACT GAT CGT ATG TTC TGC GCT GGT TAT TTG GGA CAA GGA GGC         585
Thr Asp Arg Met Phe Cys Ala Gly Tyr Leu Gly Gln Gly Gly
            185                 190                 195

AAG GAC TCA TGC CAA GGT GAT TCT GGT GGC CCA GTT GTT GTC         627
Lys Asp Ser Cys Gln Gly Asp Ser Gly Gly Pro Val Val Val
                200                 205

AAT GGT GTT CAA CAT GGA ATT GTC TCA TGG GGT CGT GGT TGT         669
Asn Gly Val Gln His Gly Ile Val Ser Trp Gly Arg Gly Cys
210                 215                 220

GCA CTT CCT GAT TAT CCT GGA GTT TAC TCT AAA ATC TCT ACC         711
Ala Leu Pro Asp Tyr Pro Gly Val Tyr Ser Lys Ile Ser Thr
        225                 230                 235

GCT CGC AGC TGG ATC AAG GAA GTG TCT GGT GTT                     744
Ala Arg Ser Trp Ile Lys Glu Val Ser Gly Val
        240                 245

(2) INFORMATION FOR SEQ ID NO:40:

(i) SEQUENCE CHARACTERISTICS:
        (A) LENGTH:  744 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:40:

AACACCAGAC ACTTCCTTGA TCCAGCTGCG AGCGGTAGAG ATTTTAGAGT           50

AAACTCCAGG ATAATCAGGA AGTGCACAAC CACGACCCCA TGAGACAATT          100

CCATGTTGAA CACCATTGAC AACAACTGGG CCACCAGAAT CACCTTGGCA          150

TGAGTCCTTG CCTCCTTGTC CCAAATAACC AGCGCAGAAC ATACGATCAG          200

TCAAACTTCC TGGGTAAGAT TTGGAGCAAG TGGTTTGGTC GACATGTGGT          250

ACTTGAACTT CTTGCAAAAC ATTGGTTGAA GGTCCATTTC CAGTTGATCC          300

CCATCCAGTA ACAGTTAACA AGGTACCAGG TTTAAGATCT ACTCCTTCAT          350

CGACCAATTT TATGATGGAC ACATCATTTG TGAGTTGAAC AGGAGTTTCG          400

AGTTCTAAGA GTGCGTAATC AAAGTCAATA GCAGCTGCGT TGTATTTTGG          450

ATGTCTGTAA TGGTTTTTAA CTTTATGCAA GATACCACCG CTGTTTACGA          500

TGGAACTTCC TACACGGACA TTGTATTTGT TAACTCCAAT GCAATGAGCT          550

GCAGTCAAAA CCCACCAGTT TTTGGCAATC AAGGAACCAC CACAATTGTG          600

GCTGGAGTAC AATAAAGATA CTTGATGAGG GTGTTTATCG ATGCTGGTAT          650

CGTGTCCTCC TACGATTCTA CTATCTAATC TTTTCCATGA TTCTGGAACA          700

CTGGCACCGA ATGTGCAGAC AGCGAGAGCA CATACAATTG CTAA               744

(2) INFORMATION FOR SEQ ID NO:41:

(i) SEQUENCE CHARACTERISTICS:
        (A) LENGTH:  933 nucleotides
        (B) TYPE:  nucleic acid
```

(C) STRANDEDNESS: single
            (D) TOPOLOGY:    linear (ii) MOLECULE TYPE: cDNA (ix) FEATURE:
            (A) NAME/KEY: CDS
            (B) LOCATION: 6..809

(ix) FEATURE:
            (A) NAME/KEY: N = Unknown nucleotide
            (B) LOCATION: 863, 908

(xi) SEQUENCE DESCRIPTION: SEQ ID NO:41:

```
GCAAC ATG AAA ATT TTA TTA CTG GTA TTA TTG GCA GTA TGC TTT              44
      Met Lys Ile Leu Leu Leu Val Leu Leu Ala Val Cys Phe
        1               5                  10

GCT TCA GCT AAA CGA GGT CCA CGA AAA CAT GTT CGC GAA ACA                86
Ala Ser Ala Lys Arg Gly Pro Arg Lys His Val Arg Glu Thr
 15                  20                  25

CAA AAA AGT CTT GCC TCT GGG CGT ATT GTG GGT GGT GAA GCA               128
Gln Lys Ser Leu Ala Ser Gly Arg Ile Val Gly Gly Glu Ala
         30                  35                  40

GTG AGC ATT GAA GAC TAT GGA TGG CAA GTT TCT CTA CAA CGT               170
Val Ser Ile Glu Asp Tyr Gly Trp Gln Val Ser Leu Gln Arg
                 45                  50                  55

TTT GGC AGT CAT TTC TGT GGA GGA TCT ATA ATA TCC AGT AGA               212
Phe Gly Ser His Phe Cys Gly Gly Ser Ile Ile Ser Ser Arg
             60                  65

TGG ATT CTT TCA GCT GCT CAT TGC TTT TAT GGA ACG TTA TTT               254
Trp Ile Leu Ser Ala Ala His Cys Phe Tyr Gly Thr Leu Phe
 70                  75                  80

CCG ATT GGA TTC TCT GCG AGA GCC GGC AGC AGT ACT GTG AAT               296
Pro Ile Gly Phe Ser Ala Arg Ala Gly Ser Ser Thr Val Asn
         85                  90                  95

TCA GGA GGA ACT GTG CAT ACA ATT TTG TAT TGG TAT ATT CAT               338
Ser Gly Gly Thr Val His Thr Ile Leu Tyr Trp Tyr Ile His
                100                 105                 110

CCA AAT TAT GAT TCA CAA AGT ACA GAC TTT GAT GTT TCT GTA               380
Pro Asn Tyr Asp Ser Gln Ser Thr Asp Phe Asp Val Ser Val
             115                 120                 125

GTT CGA CTA TTA TCT TCT TTA AAT TTG AAT GGA GGT TCT ATT               422
Val Arg Leu Leu Ser Ser Leu Asn Leu Asn Gly Gly Ser Ile
                 130                 135

CGA CCG GCT AGG TTA GTG GAT TCT GGA ACT GAT TTG CCA GCC               464
Arg Pro Ala Arg Leu Val Asp Ser Gly Thr Asp Leu Pro Ala
140                 145                 150

GGT GAG ATG GTT ACA GTA ACT GGA TGG GGA CGA CTT TCG GAA               506
Gly Glu Met Val Thr Val Thr Gly Trp Gly Arg Leu Ser Glu
        155                 160                 165

AAT ACT TCT GTT CCC TCG CCA TCA ACT CTT CAA GGA GTT ACA               548
Asn Thr Ser Val Pro Ser Pro Ser Thr Leu Gln Gly Val Thr
            170                 175                 180

GTA CCA GTT GTA AGT AAT TCG GAA TGT CAA CAA CAA TTG CAA               590
Val Pro Val Val Ser Asn Ser Glu Cys Gln Gln Gln Leu Gln
                185                 190                 195

AAT CAG ACA ATC ACT GAC AAT ATG TTT TGT GCT GGT GAA TTA               632
Asn Gln Thr Ile Thr Asp Asn Met Phe Cys Ala Gly Glu Leu
            200                 205

GAA GGA GGA AAG GAC TCT TGT CAA GGA GAC AGT GGT GGT CCC               674
Glu Gly Gly Lys Asp Ser Cys Gln Gly Asp Ser Gly Gly Pro
210                 215                 220
```

```
ATG GTT GAC AGC GAG GAT ACT CAA GTA GGA ATT GTA TCC TGG        716
Met Val Asp Ser Glu Asp Thr Gln Val Gly Ile Val Ser Trp
225                 230                 235

GGA ATA GGA TGT GCT AGA CCC AAT TTA CCA GGA GTT TAT ACG        758
Gly Ile Gly Cys Ala Arg Pro Asn Leu Pro Gly Val Tyr Thr
240                 245                 250

CGA ATT GCT TCA TCG CCA ATT AGA GAT TTC ATA AGA CGA ATA        800
Arg Ile Ala Ser Ser Pro Ile Arg Asp Phe Ile Arg Arg Ile
        255                 260                 265

ACC GGA GTT TAA TATTATTTTA TACATTTTTG ACAAATATGA               842
Thr Gly Val

GAACTAATGA GAACTGTTGT NTTGCTATAA TTCTTTGCAA CATTGTGCAT         892

GAATAAATTA TGAATNTAAT TGTTAAAAAA AAAAAAAAA A                   933

(2) INFORMATION FOR SEQ ID NO:42:

(i) SEQUENCE CHARACTERISTICS:
        (A) LENGTH:  268 amino acids
        (B) TYPE:  amino acid
        (D) TOPOLOGY:  linear (ii) MOLECULE TYPE:  Protein (xi) SEQUENCE DESCRIPTION: SEQ ID NO:42:

Met Lys Ile Leu Leu Leu Val Leu Leu Ala Val Cys Phe
1               5                   10

Ala Ser Ala Lys Arg Gly Pro Arg Lys His Val Arg Glu Thr
        15                  20                  25

Gln Lys Ser Leu Ala Ser Gly Arg Ile Val Gly Gly Glu Ala
            30                  35                  40

Val Ser Ile Glu Asp Tyr Gly Trp Gln Val Ser Leu Gln Arg
                45                  50                  55

Phe Gly Ser His Phe Cys Gly Gly Ser Ile Ile Ser Ser Arg
                    60                  65

Trp Ile Leu Ser Ala Ala His Cys Phe Tyr Gly Thr Leu Phe
70                  75                  80

Pro Ile Gly Phe Ser Ala Arg Ala Gly Ser Ser Thr Val Asn
    85                  90                  95

Ser Gly Gly Thr Val His Thr Ile Leu Tyr Trp Tyr Ile His
        100                 105                 110

Pro Asn Tyr Asp Ser Gln Ser Thr Asp Phe Asp Val Ser Val
            115                 120                 125

Val Arg Leu Leu Ser Ser Leu Asn Leu Asn Gly Gly Ser Ile
                130                 135

Arg Pro Ala Arg Leu Val Asp Ser Gly Thr Asp Leu Pro Ala
140                 145                 150

Gly Glu Met Val Thr Val Thr Gly Trp Gly Arg Leu Ser Glu
    155                 160                 165

Asn Thr Ser Val Pro Ser Pro Ser Thr Leu Gln Gly Val Thr
        170                 175                 180

Val Pro Val Val Ser Asn Ser Glu Cys Gln Gln Gln Leu Gln
            185                 190                 195

Asn Gln Thr Ile Thr Asp Asn Met Phe Cys Ala Gly Glu Leu
                200                 205

Glu Gly Gly Lys Asp Ser Cys Gln Gly Asp Ser Gly Gly Pro
210                 215                 220
```

```
Met Val Asp Ser Glu Asp Thr Gln Val Gly Ile Val Ser Trp
    225                 230                 235

Gly Ile Gly Cys Ala Arg Pro Asn Leu Pro Gly Val Tyr Thr
            240                 245                 250

Arg Ile Ala Ser Ser Pro Ile Arg Asp Phe Ile Arg Arg Ile
                255                 260                 265

Thr Gly Val
```

(2) INFORMATION FOR SEQ ID NO:43:

(i) SEQUENCE CHARACTERISTICS:
        (A) LENGTH: 933 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: N = Unknown nucleotide
        (B) LOCATION: 26, 71

(xi) SEQUENCE DESCRIPTION: SEQ ID NO:43:

```
TTTTTTTTTT TTTTTTTAAC AATTANATTC ATAATTTATT CATGCACAAT        50
GTTGCAAAGA ATTATAGCAA NACAACAGTT CTCATTAGTT CTCATATTTG       100
TCAAAAATGT ATAAAATAAT ATTAAACTCC GGTTATTCGT CTTATGAAAT       150
CTCTAATTGG CGATGAAGCA ATTCGCGTAT AAACTCCTGG TAAATTGGGT       200
CTAGCACATC CTATTCCCCA GGATACAATT CCTACTTGAG TATCCTCGCT       250
GTCAACCATG GGACCACCAC TGTCTCCTTG ACAAGAGTCC TTTCCTCCTT       300
CTAATTCACC AGCACAAAAC ATATTGTCAG TGATTGTCTG ATTTTGCAAT       350
TGTTGTTGAC ATTCCGAATT ACTTACAACT GGTACTGTAA CTCCTTGAAG       400
AGTTGATGGC GAGGGAACAG AAGTATTTTC CGAAAGTCGT CCCCATCCAG       450
TTACTGTAAC CATCTCACCG GCTGGCAAAT CAGTTCCAGA ATCCACTAAC       500
CTAGCCGGTC GAATAGAACC TCCATTCAAA TTTAAAGAAG ATAATAGTCG       550
AACTACAGAA ACATCAAAGT CTGTACTTTG TGAATCATAA TTTGGATGAA       600
TATACCAATA CAAAATTGTA TGCACAGTTC CTCCTGAATT CACAGTACTG       650
CTGCCGGCTC TCGCAGAGAA TCCAATCGGA ATAACGTTC CATAAAAGCA        700
ATGAGCAGCT GAAAGAATCC ATCTACTGGA TATTATAGAT CCTCCACAGA       750
AATGACTGCC AAAACGTTGT AGAGAAACTT GCCATCCATA GTCTTCAATG       800
CTCACTGCTT CACCACCCAC AATACGCCCA GAGGCAAGAC TTTTTTGTGT       850
TTCGCGAACA TGTTTTCGTG GACCTCGTTT AGCTGAAGCA AAGCATACTG       900
CCAATAATAC CAGTAATAAA ATTTTCATGT TGC                         933
```

(2) INFORMATION FOR SEQ ID NO:44:

(i) SEQUENCE CHARACTERISTICS:
        (A) LENGTH: 804 nucleotides
        (B) TYPE: nucleic acid
        (C) STRANDEDNESS: single
        (D) TOPOLOGY: linear (ii) MOLECULE TYPE: cDNA -continued (ix) FEATURE:
      (A) NAME/KEY: CDS
      (B) LOCATION: 1..804

(xi) SEQUENCE DESCRIPTION: SEQ ID NO:44:

| | | | | | | | | | | | | | |
|---|---|---|---|---|---|---|---|---|---|---|---|---|---|
| ATG | AAA | ATT | TTA | TTA | CTG | GTA | TTA | TTG | GCA | GTA | TGC | TTT | 39 |
| Met | Lys | Ile | Leu | Leu | Leu | Val | Leu | Leu | Ala | Val | Cys | Phe | |
| 1 | | | | 5 | | | | | 10 | | | | |
| GCT | TCA | GCT | AAA | CGA | GGT | CCA | CGA | AAA | CAT | GTT | CGC | GAA | ACA | 81 |
| Ala | Ser | Ala | Lys | Arg | Gly | Pro | Arg | Lys | His | Val | Arg | Glu | Thr |
| | 15 | | | | | 20 | | | | | 25 | | |
| CAA | AAA | AGT | CTT | GCC | TCT | GGG | CGT | ATT | GTG | GGT | GGT | GAA | GCA | 123 |
| Gln | Lys | Ser | Leu | Ala | Ser | Gly | Arg | Ile | Val | Gly | Gly | Glu | Ala |
| | 30 | | | | | 35 | | | | | 40 | | |
| GTG | AGC | ATT | GAA | GAC | TAT | GGA | TGG | CAA | GTT | TCT | CTA | CAA | CGT | 165 |
| Val | Ser | Ile | Glu | Asp | Tyr | Gly | Trp | Gln | Val | Ser | Leu | Gln | Arg |
| | | 45 | | | | | 50 | | | | | 55 | |
| TTT | GGC | AGT | CAT | TTC | TGT | GGA | GGA | TCT | ATA | ATA | TCC | AGT | AGA | 207 |
| Phe | Gly | Ser | His | Phe | Cys | Gly | Gly | Ser | Ile | Ile | Ser | Ser | Arg |
| | | 60 | | | | | 65 | | | | | | |
| TGG | ATT | CTT | TCA | GCT | GCT | CAT | TGC | TTT | TAT | GGA | ACG | TTA | TTT | 249 |
| Trp | Ile | Leu | Ser | Ala | Ala | His | Cys | Phe | Tyr | Gly | Thr | Leu | Phe |
| 70 | | | | 75 | | | | | 80 | | | | |
| CCG | ATT | GGA | TTC | TCT | GCG | AGA | GCC | GGC | AGC | AGT | ACT | GTG | AAT | 291 |
| Pro | Ile | Gly | Phe | Ser | Ala | Arg | Ala | Gly | Ser | Ser | Thr | Val | Asn |
| | 85 | | | | | 90 | | | | | 95 | | |
| TCA | GGA | GGA | ACT | GTG | CAT | ACA | ATT | TTG | TAT | TGG | TAT | ATT | CAT | 333 |
| Ser | Gly | Gly | Thr | Val | His | Thr | Ile | Leu | Tyr | Trp | Tyr | Ile | His |
| | | 100 | | | | | 105 | | | | | 110 | |
| CCA | AAT | TAT | GAT | TCA | CAA | AGT | ACA | GAC | TTT | GAT | GTT | TCT | GTA | 375 |
| Pro | Asn | Tyr | Asp | Ser | Gln | Ser | Thr | Asp | Phe | Asp | Val | Ser | Val |
| | | | 115 | | | | | 120 | | | | | 125 |
| GTT | CGA | CTA | TTA | TCT | TCT | TTA | AAT | TTG | AAT | GGA | GGT | TCT | ATT | 417 |
| Val | Arg | Leu | Leu | Ser | Ser | Leu | Asn | Leu | Asn | Gly | Gly | Ser | Ile |
| | | | | 130 | | | | | 135 | | | | |
| CGA | CCG | GCT | AGG | TTA | GTG | GAT | TCT | GGA | ACT | GAT | TTG | CCA | GCC | 459 |
| Arg | Pro | Ala | Arg | Leu | Val | Asp | Ser | Gly | Thr | Asp | Leu | Pro | Ala |
| 140 | | | | 145 | | | | | 150 | | | | |
| GGT | GAG | ATG | GTT | ACA | GTA | ACT | GGA | TGG | GGA | CGA | CTT | TCG | GAA | 501 |
| Gly | Glu | Met | Val | Thr | Val | Thr | Gly | Trp | Gly | Arg | Leu | Ser | Glu |
| | 155 | | | | | 160 | | | | | 165 | | |
| AAT | ACT | TCT | GTT | CCC | TCG | CCA | TCA | ACT | CTT | CAA | GGA | GTT | ACA | 543 |
| Asn | Thr | Ser | Val | Pro | Ser | Pro | Ser | Thr | Leu | Gln | Gly | Val | Thr |
| | | 170 | | | | | 175 | | | | | 180 | |
| GTA | CCA | GTT | GTA | AGT | AAT | TCG | GAA | TGT | CAA | CAA | CAA | TTG | CAA | 585 |
| Val | Pro | Val | Val | Ser | Asn | Ser | Glu | Cys | Gln | Gln | Gln | Leu | Gln |
| | | | 185 | | | | | 190 | | | | | 195 |
| AAT | CAG | ACA | ATC | ACT | GAC | AAT | ATG | TTT | TGT | GCT | GGT | GAA | TTA | 627 |
| Asn | Gln | Thr | Ile | Thr | Asp | Asn | Met | Phe | Cys | Ala | Gly | Glu | Leu |
| | | | | 200 | | | | | 205 | | | | |
| GAA | GGA | GGA | AAG | GAC | TCT | TGT | CAA | GGA | GAC | AGT | GGT | GGT | CCC | 669 |
| Glu | Gly | Gly | Lys | Asp | Ser | Cys | Gln | Gly | Asp | Ser | Gly | Gly | Pro |
| 210 | | | | 215 | | | | | 220 | | | | |
| ATG | GTT | GAC | AGC | GAG | GAT | ACT | CAA | GTA | GGA | ATT | GTA | TCC | TGG | 711 |
| Met | Val | Asp | Ser | Glu | Asp | Thr | Gln | Val | Gly | Ile | Val | Ser | Trp |
| | 225 | | | | | 230 | | | | | 235 | | |
| GGA | ATA | GGA | TGT | GCT | AGA | CCC | AAT | TTA | CCA | GGA | GTT | TAT | ACG | 753 |
| Gly | Ile | Gly | Cys | Ala | Arg | Pro | Asn | Leu | Pro | Gly | Val | Tyr | Thr |
| | | 240 | | | | | 245 | | | | | 250 | |

| | | |
|---|---|---|
| CGA ATT GCT TCA TCG CCA ATT AGA GAT TTC ATA AGA CGA ATA | | 795 |
| Arg Ile Ala Ser Ser Pro Ile Arg Asp Phe Ile Arg Arg Ile | | |
| 255 260 265 | | |
| | | |
| ACC GGA GTT | | 804 |
| Thr Gly Val | | |

(2) INFORMATION FOR SEQ ID NO:45:

(i) SEQUENCE CHARACTERISTICS:
        (A) LENGTH: 804 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

| | |
|---|---|
| AACTCCGGTT ATTCGTCTTA TGAAATCTCT AATTGGCGAT GAAGCAATTC | 50 |
| GCGTATAAAC TCCTGGTAAA TTGGGTCTAG CACATCCTAT TCCCCAGGAT | 100 |
| ACAATTCCTA CTTGAGTATC CTCGCTGTCA ACCATGGGAC CACCACTGTC | 150 |
| TCCTTGACAA GAGTCCTTTC CTCCTTCTAA TTCACCAGCA CAAAACATAT | 200 |
| TGTCAGTGAT TGTCTGATTT TGCAATTGTT GTTGACATTC CGAATTACTT | 250 |
| ACAACTGGTA CTGTAACTCC TTGAAGAGTT GATGGCGAGG GAACAGAAGT | 300 |
| ATTTTCCGAA AGTCGTCCCC ATCCAGTTAC TGTAACCATC TCACCGGCTG | 350 |
| GCAAATCAGT TCCAGAATCC ACTAACCTAG CCGGTCGAAT AGAACCTCCA | 400 |
| TTCAAATTTA AAGAAGATAA TAGTCGAACT ACAGAAACAT CAAAGTCTGT | 450 |
| ACTTTGTGAA TCATAATTTG GATGAATATA CCAATACAAA ATTGTATGCA | 500 |
| CAGTTCCTCC TGAATTCACA GTACTGCTGC CGGCTCTCGC AGAGAATCCA | 550 |
| ATCGGAAATA ACGTTCCATA AAAGCAATGA GCAGCTGAAA GAATCCATCT | 600 |
| ACTGGATATT ATAGATCCTC CACAGAAATG ACTGCCAAAA CGTTGTAGAG | 650 |
| AAACTTGCCA TCCATAGTCT TCAATGCTCA CTGCTTCACC ACCCACAATA | 700 |
| CGCCCAGAGG CAAGACTTTT TTGTGTTTCG CGAACATGTT TTCGTGGACC | 750 |
| TCGTTTAGCT GAAGCAAAGC ATACTGCCAA TAATACCAGT AATAAAATTT | 800 |
| TCAT | 804 |

(2) INFORMATION FOR SEQ ID NO:46:

(i) SEQUENCE CHARACTERISTICS:
        (A) LENGTH: 841 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..727

(ix) FEATURE:
        (A) NAME/KEY: N = Unknown nucleotide
        (B) LOCATION: 627, 768, 809

(ix) FEATURE:
        (A) NAME/KEY: Xaa = Unknown amino acid
        (B) LOCATION: 209

(xi) SEQUENCE DESCRIPTION: SEQ ID NO:46:

-continued

```
A GAT CAT CGA ATA GTA GGA GGT GAA GAT GTA GAT ATT TCA          40
  Asp His Arg Ile Val Gly Gly Glu Asp Val Asp Ile Ser
   1               5                  10

ACT TGT GGA TGG CAA GTT TCG TTT CAC AAT AGG AAA GGA CAT         82
Thr Cys Gly Trp Gln Val Ser Phe His Asn Arg Lys Gly His
     15                  20                  25

TTT TGT GGA GGG TCC ATC ATT GGC AAA GAA TGG ATT CTA ACT        124
Phe Cys Gly Gly Ser Ile Ile Gly Lys Glu Trp Ile Leu Thr
             30                  35                  40

GCT GCG CAT TGT GTA ACC AAA TAT GAA AAC GAT ATC GAA GGT        166
Ala Ala His Cys Val Thr Lys Tyr Glu Asn Asp Ile Glu Gly
                 45                  50                  55

TTA AAA GTT AGG GTT GGA AGC AAT GAG CAT AAC AAA GGT GGG        208
Leu Lys Val Arg Val Gly Ser Asn Glu His Asn Lys Gly Gly
                     60                  65

CGT TTA TAC GAC ATT AAA GAA ATT AAA AAA CAT CCA AGA TAT        250
Arg Leu Tyr Asp Ile Lys Glu Ile Lys Lys His Pro Arg Tyr
 70              75                  80

AAC GAT CGA ACC AGA TAC GAT TTT GAT GTC GCT TTA TTA CGC        292
Asn Asp Arg Thr Arg Tyr Asp Phe Asp Val Ala Leu Leu Arg
     85                  90                  95

ATT GCA AAG CCA ATT GCA TAC ACT GCT TGC ACT GTT GTT CCT        334
Ile Ala Lys Pro Ile Ala Tyr Thr Ala Cys Thr Val Val Pro
         100                 105                 110

GTA GCA TTG GCA GAA ACT GGA AAA GAA GTT CCA GAA GGC GCA        376
Val Ala Leu Ala Glu Thr Gly Lys Glu Val Pro Glu Gly Ala
             115                 120                 125

CTC GTT AGT GTC ACA GGA TGG GGG GCT ACT ATG GTG GGC GGC        418
Leu Val Ser Val Thr Gly Trp Gly Ala Thr Met Val Gly Gly
                 130                 135

CCA GCA TCA ACG CAT CTA AAA GGT GTT AAG GTT CCA ATC GTG        460
Pro Ala Ser Thr His Leu Lys Gly Val Lys Val Pro Ile Val
140                 145                 150

TCA AAT GAA GAA TGC AAC AAA AAT TAT ACC ATT CCT GGA GGT        502
Ser Asn Glu Glu Cys Asn Lys Asn Tyr Thr Ile Pro Gly Gly
    155                 160                 165

CTG GAT GAC AAA ATT TCA GAC AGC ATG TTT TGC GCT GGT TTC        544
Leu Asp Asp Lys Ile Ser Asp Ser Met Phe Cys Ala Gly Phe
        170                 175                 180

CCT GAA GGC GGA AAG GAC TCG TGT CAA GGA GAT AGC GGT GGG        586
Pro Glu Gly Gly Lys Asp Ser Cys Gln Gly Asp Ser Gly Gly
            185                 190                 195

CCT GTA GTG GAT GAA AAT AGG GTT CAG GTC GGA ATT GTG TNT        628
Pro Val Val Asp Glu Asn Arg Val Gln Val Gly Ile Val Xaa
                200                 205

TGG GGC GAA GGC TGT GCT TTA GCA GGA AAA CCA GGC GTT TAT        670
Trp Gly Glu Gly Cys Ala Leu Ala Gly Lys Pro Gly Val Tyr
210                 215                 220

GCA AAA GTT TCA CAT CCT GAC GTA AAA AGG TTT ATT GAA ACC        712
Ala Lys Val Ser His Pro Asp Val Lys Arg Phe Ile Glu Thr
    225                 230                 235

GTA GCA GGA ATC AAA TAA AATTTGTTAG AAAAAATGTA GACAAGTTGT       760
Val Ala Gly Ile Lys
        240

ATAAACTNTC AATGAAATTG TTTTATTTTT GGAAATAAAA TATAATTTNT         810

GAAAAAAAAA AAAAAAAAAA AAAAAAAAAA A                             841
```

(2) INFORMATION FOR SEQ ID NO:47:

(i) SEQUENCE CHARACTERISTICS:
        (A) LENGTH: 242 amino acids
        (B) TYPE: amino acid
        (D) TOPOLOGY: linear (ii) MOLECULE TYPE: Protein (ix) FEATURE:
        (A) NAME/KEY: Xaa = Unknown amino acid
        (B) LOCATION: 209

(xi) SEQUENCE DESCRIPTION: SEQ ID NO:47:

```
Asp His Arg Ile Val Gly Gly Glu Asp Val Asp Ile Ser
 1               5                  10
Thr Cys Gly Trp Gln Val Ser Phe His Asn Arg Lys Gly His
        15                  20                  25
Phe Cys Gly Gly Ser Ile Ile Gly Lys Glu Trp Ile Leu Thr
            30                  35                  40
Ala Ala His Cys Val Thr Lys Tyr Glu Asn Asp Ile Glu Gly
                45                  50                  55
Leu Lys Val Arg Val Gly Ser Asn Glu His Asn Lys Gly Gly
                    60                  65
Arg Leu Tyr Asp Ile Lys Glu Ile Lys Lys His Pro Arg Tyr
 70                  75                  80
Asn Asp Arg Thr Arg Tyr Asp Phe Asp Val Ala Leu Leu Arg
        85                  90                  95
Ile Ala Lys Pro Ile Ala Tyr Thr Ala Cys Thr Val Val Pro
            100                 105                 110
Val Ala Leu Ala Glu Thr Gly Lys Glu Val Pro Glu Gly Ala
                115                 120                 125
Leu Val Ser Val Thr Gly Trp Gly Ala Thr Met Val Gly Gly
                    130                 135
Pro Ala Ser Thr His Leu Lys Gly Val Lys Val Pro Ile Val
140                 145                 150
Ser Asn Glu Glu Cys Asn Lys Asn Tyr Thr Ile Pro Gly Gly
        155                 160                 165
Leu Asp Asp Lys Ile Ser Asp Ser Met Phe Cys Ala Gly Phe
            170                 175                 180
Pro Glu Gly Gly Lys Asp Ser Cys Gln Gly Asp Ser Gly Gly
                185                 190                 195
Pro Val Val Asp Glu Asn Arg Val Gln Val Gly Ile Val Xaa
                    200                 205
Trp Gly Glu Gly Cys Ala Leu Ala Gly Lys Pro Gly Val Tyr
210                 215                 220
Ala Lys Val Ser His Pro Asp Val Lys Arg Phe Ile Glu Thr
        225                 230                 235
Val Ala Gly Ile Lys
        240
```

(2) INFORMATION FOR SEQ ID NO:48:

(i) SEQUENCE CHARACTERISTICS:
        (A) LENGTH: 841 nucleotides
        (B) TYPE: nucleic acid
        (C) STRANDEDNESS: single
        (D) TOPOLOGY: linear (ii) MOLECULE TYPE:  cDNA (ix) FEATURE:
             (A) NAME/KEY:  N = Unknown nucleotide
             (B) LOCATION:  33, 74, 215

(xi) SEQUENCE DESCRIPTION:  SEQ ID NO:48:

TTTTTTTTTT TTTTTTTTTT TTTTTTTTTT CANAAATTAT ATTTTATTTC        50

CAAAAATAAA ACAATTTCAT TGANAGTTTA TACAACTTGT CTACATTTTT       100

TCTAACAAAT TTTATTTGAT TCCTGCTACG GTTTCAATAA ACCTTTTTAC       150

GTCAGGATGT GAAACTTTTG CATAAACGCC TGGTTTTCCT GCTAAAGCAC       200

AGCCTTCGCC CCAANACACA ATTCCGACCT GAACCCTATT TTCATCCACT       250

ACAGGCCCAC CGCTATCTCC TTGACACGAG TCCTTTCCGC CTTCAGGGAA       300

ACCAGCGCAA AACATGCTGT CTGAAATTTT GTCATCCAGA CCTCCAGGAA       350

TGGTATAATT TTTGTTGCAT TCTTCATTTG ACACGATTGG AACCTTAACA       400

CCTTTTAGAT GCGTTGATGC TGGGCCGCCC ACCATAGTAG CCCCCCATCC       450

TGTGACACTA ACGAGTGCGC CTTCTGGAAC TTCTTTTCCA GTTTCTGCCA       500

ATGCTACAGG AACAACAGTG CAAGCAGTGT ATGCAATTGG CTTTGCAATG       550

CGTAATAAAG CGACATCAAA ATCGTATCTG GTTCGATCGT TATATCTTGG       600

ATGTTTTTTA ATTTCTTTAA TGTCGTATAA ACGCCCACCT TTGTTATGCT       650

CATTGCTTCC AACCCTAACT TTTAAACCTT CGATATCGTT TTCATATTTG       700

GTTACACAAT GCGCAGCAGT TAGAATCCAT TCTTTGCCAA TGATGGACCC       750

TCCACAAAAA TGTCCTTTCC TATTGTGAAA CGAAACTTGC CATCCACAAG       800

TTGAAATATC TACATCTTCA CCTCCTACTA TTCGATGATC T                841

(2) INFORMATION FOR SEQ ID NO:49:

(i) SEQUENCE CHARACTERISTICS:
             (A) LENGTH:  726 nucleotides
             (B) TYPE:  nucleic acid
             (C) STRANDEDNESS:  single
             (D) TOPOLOGY:  linear (ii) MOLECULE TYPE:  cDNA (ix) FEATURE:
             (A) NAME/KEY:  CDS
             (B) LOCATION:  1..726

(ix) FEATURE:
             (A) NAME/KEY:  N = Unknown nucleotide
             (B) LOCATION:  626

(ix) FEATURE:
             (A) NAME/KEY:  Xaa = Unknown amino acid
             (B) LOCATION:  209

(xi) SEQUENCE DESCRIPTION:  SEQ ID NO:49:

GAT CAT CGA ATA GTA GGA GGT GAA GAT GTA GAT ATT TCA            39
Asp His Arg Ile Val Gly Gly Glu Asp Val Asp Ile Ser
 1               5                  10

ACT TGT GGA TGG CAA GTT TCG TTT CAC AAT AGG AAA GGA CAT        81
Thr Cys Gly Trp Gln Val Ser Phe His Asn Arg Lys Gly His
        15                  20                  25

TTT TGT GGA GGG TCC ATC ATT GGC AAA GAA TGG ATT CTA ACT       123
Phe Cys Gly Gly Ser Ile Ile Gly Lys Glu Trp Ile Leu Thr
                30                  35                  40

```
GCT GCG CAT TGT GTA ACC AAA TAT GAA AAC GAT ATC GAA GGT              165
Ala Ala His Cys Val Thr Lys Tyr Glu Asn Asp Ile Glu Gly
            45                  50                  55

TTA AAA GTT AGG GTT GGA AGC AAT GAG CAT AAC AAA GGT GGG              207
Leu Lys Val Arg Val Gly Ser Asn Glu His Asn Lys Gly Gly
                60                  65

CGT TTA TAC GAC ATT AAA GAA ATT AAA AAA CAT CCA AGA TAT              249
Arg Leu Tyr Asp Ile Lys Glu Ile Lys Lys His Pro Arg Tyr
 70                  75                  80

AAC GAT CGA ACC AGA TAC GAT TTT GAT GTC GCT TTA TTA CGC              291
Asn Asp Arg Thr Arg Tyr Asp Phe Asp Val Ala Leu Leu Arg
        85                  90                  95

ATT GCA AAG CCA ATT GCA TAC ACT GCT TGC ACT GTT GTT CCT              333
Ile Ala Lys Pro Ile Ala Tyr Thr Ala Cys Thr Val Val Pro
            100                 105                 110

GTA GCA TTG GCA GAA ACT GGA AAA GAA GTT CCA GAA GGC GCA              375
Val Ala Leu Ala Glu Thr Gly Lys Glu Val Pro Glu Gly Ala
                115                 120                 125

CTC GTT AGT GTC ACA GGA TGG GGG GCT ACT ATG GTG GGC GGC              417
Leu Val Ser Val Thr Gly Trp Gly Ala Thr Met Val Gly Gly
                    130                 135

CCA GCA TCA ACG CAT CTA AAA GGT GTT AAG GTT CCA ATC GTG              459
Pro Ala Ser Thr His Leu Lys Gly Val Lys Val Pro Ile Val
140                 145                 150

TCA AAT GAA GAA TGC AAC AAA AAT TAT ACC ATT CCT GGA GGT              501
Ser Asn Glu Glu Cys Asn Lys Asn Tyr Thr Ile Pro Gly Gly
        155                 160                 165

CTG GAT GAC AAA ATT TCA GAC AGC ATG TTT TGC GCT GGT TTC              543
Leu Asp Asp Lys Ile Ser Asp Ser Met Phe Cys Ala Gly Phe
            170                 175                 180

CCT GAA GGC GGA AAG GAC TCG TGT CAA GGA GAT AGC GGT GGG              585
Pro Glu Gly Gly Lys Asp Ser Cys Gln Gly Asp Ser Gly Gly
                185                 190                 195

CCT GTA GTG GAT GAA AAT AGG GTT CAG GTC GGA ATT GTG TNT              627
Pro Val Val Asp Glu Asn Arg Val Gln Val Gly Ile Val Xaa
                    200                 205

TGG GGC GAA GGC TGT GCT TTA GCA GGA AAA CCA GGC GTT TAT              669
Trp Gly Glu Gly Cys Ala Leu Ala Gly Lys Pro Gly Val Tyr
210                 215                 220

GCA AAA GTT TCA CAT CCT GAC GTA AAA AGG TTT ATT GAA ACC              711
Ala Lys Val Ser His Pro Asp Val Lys Arg Phe Ile Glu Thr
        225                 230                 235

GTA GCA GGA ATC AAA                                                  726
Val Ala Gly Ile Lys
        240
```

(2) INFORMATION FOR SEQ ID NO:50:

(i) SEQUENCE CHARACTERISTICS:
        (A) LENGTH: 726 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: N = Unknown nucleotide
        (B) LOCATION: 101

(xi) SEQUENCE DESCRIPTION: SEQ ID NO:50:

-continued

| | | | | |
|---|---|---|---|---|
| TTTGATTCCT | GCTACGGTTT | CAATAAACCT | TTTTACGTCA | GGATGTGAAA | 50 |
| CTTTTGCATA | AACGCCTGGT | TTTCCTGCTA | AAGCACAGCC | TTCGCCCCAA | 100 |
| NACACAATTC | CGACCTGAAC | CCTATTTTCA | TCCACTACAG | GCCCACCGCT | 150 |
| ATCTCCTTGA | CACGAGTCCT | TTCCGCCTTC | AGGGAAACCA | GCGCAAAACA | 200 |
| TGCTGTCTGA | AATTTTGTCA | TCCAGACCTC | CAGGAATGGT | ATAATTTTTG | 250 |
| TTGCATTCTT | CATTTGACAC | GATTGGAACC | TTAACACCTT | TTAGATGCGT | 300 |
| TGATGCTGGG | CCGCCCACCA | TAGTAGCCCC | CCATCCTGTG | ACACTAACGA | 350 |
| GTGCGCCTTC | TGGAACTTCT | TTTCCAGTTT | CTGCCAATGC | TACAGGAACA | 400 |
| ACAGTGCAAG | CAGTGTATGC | AATTGGCTTT | GCAATGCGTA | ATAAAGCGAC | 450 |
| ATCAAAATCG | TATCTGGTTC | GATCGTTATA | TCTTGGATGT | TTTTTAATTT | 500 |
| CTTTAATGTC | GTATAAACGC | CCACCTTTGT | TATGCTCATT | GCTTCCAACC | 550 |
| CTAACTTTTA | AACCTTCGAT | ATCGTTTTCA | TATTTGGTTA | CACAATGCGC | 600 |
| AGCAGTTAGA | ATCCATTCTT | TGCCAATGAT | GGACCCTCCA | CAAAAATGTC | 650 |
| CTTTCCTATT | GTGAAACGAA | ACTTGCCATC | CACAAGTTGA | AATATCTACA | 700 |
| TCTTCACCTC | CTACTATTCG | ATGATC | | | 726 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule selected from the group consisting of:
   (a) a nucleic acid molecule comprising a nucleic acid sequence that encodes an amino acid sequence selected from the group consisting of SEQ ID NO:8, SEQ ID NO:22, SEQ ID NO:27, SEQ ID NO:32, SEQ ID NO:37, SEQ ID NO:42 and SEQ ID NO:47; and,
   (b) a nucleic acid molecule that is fully complementary to any of said nucleic acid molecules of (a).

2. The nucleic acid molecule of claim 1, wherein said nucleic acid molecule comprises a nucleic acid sequence that encodes an amino acid sequence selected from the group consisting SEQ ID NO:8, SEQ ID NO:22, SEQ ID NO:27, SEQ ID NO:32, SEQ ID NO:37, SEQ ID NO:42 and SEQ ID NO:47.

3. The nucleic acid molecule of claim 2, wherein said nucleic acid molecule encodes a protein that, when administered to an animal, elicits an immune response against a flea serine protease protein.

4. The nucleic acid molecule of claim 1, wherein said nucleic acid molecule is selected from the group consisting of Ctenocephalides, Ceratophyllus, Diamanus, Echidnophaga, Nosopsyllus, Pulex, Tunga, Oropsylla, Orchopeus and Xenopsylla nucleic acid molecules.

5. The nucleic acid molecule of claim 1, wherein said nucleic acid molecule is selected from the group consisting of Ctenocephalides felis, Ctenocephalides canis, Ceratophyllus pulicidae, Pulex irritans, Oropsylla (Thrassis) bacchi, Oropsylla (Diamanus) montana, Orchopeus howardi, Xenopsylla cheopis and Pulex simulans nucleic acid molecules.

6. The nucleic acid molecule of claim 1, wherein said nucleic acid molecule comprises a Ctenocephalides felis nucleic acid molecule.

7. The nucleic acid molecule of claim 1, wherein said nucleic acid molecule comprises a nucleic acid molecule selected from the group consisting of $nfSP33_{1373}$, $nfSP33_{1161}$, $nfSP8_{1303}$, $nfSP8_{1152}$, $nfSP2_{945}$, $nfSP2_{768}$, $nfSP6_{932}$, $nfSP6_{768}$, $nfSP20_{841}$, $nfSP20_{744}$, $nfSP32_{933}$, $nfSP32_{804}$, $nfSP40_{841}$ and $nfSP40_{726}$.

8. The nucleic acid molecule of claim 1, wherein said nucleic acid molecule comprises a nucleic acid sequence selected from the group consisting of SEQ ID NO:6, SEQ ID NO:7, SEQ ID NO:9, SEQ ID NO: 10, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:48, SEQ ID NO:49 and SEQ ID NO:50.

9. A recombinant molecule comprising a nucleic acid molecule as set forth in claim 1 operatively linked to a transcription control sequence.

10. A recombinant virus comprising a nucleic acid molecule as set forth in claim 1.

11. An isolated recombinant cell comprising a nucleic acid molecule as set forth in claim 1, said cell being capable of expressing said nucleic acid molecule.

12. The nucleic acid molecule of claim 1, wherein said nucleic acid molecule comprises a nucleic acid sequence selected from the group consisting of: SEQ ID NO:6, SEQ ID NO:9, SEQ ID NO:21, SEQ ID NO:24, SEQ ID NO:26, SEQ ID NO:29, SEQ ID NO:31, SEQ ID NO:34, SEQ ID NO:36, SEQ ID NO:39, SEQ ID NO:41, SEQ ID NO:44, SEQ ID NO:46, and SEQ ID NO:49.

13. A method to produce a protein, said method comprising culturing an isolated cell capable of expressing said protein under conditions whereby said protein is produced, said protein being encoded by a nucleic acid molecule selected from the group consisting of a nucleic acid molecule comprising a nucleic acid sequence that encodes an amino acid sequence selected from the group consisting of SEQ ID NO:8, SEQ ID NO:22, SEQ ID NO:27, SEQ ID NO:32, SEQ ID NO:37, SEQ ID NO:42 and SEQ ID NO:47.

14. The method of claim 13, wherein said protein is encoded by a nucleic acid molecule comprising a nucleic acid sequence selected from the group consisting of: SEQ ID NO:6, SEQ ID NO:9, SEQ ID NO:21, SEQ ID NO:24, SEQ ID NO:26, SEQ ID NO:29, SEQ ID NO:31, SEQ ID NO:34, SEQ ID NO:36, SEQ ID NO:39, SEQ ID NO:41, SEQ ID NO:44, SEQ ID NO:46, and SEQ ID NO:49.

* * * * *